US009026369B2

(12) United States Patent
Hyde et al.

(10) Patent No.: US 9,026,369 B2
(45) Date of Patent: May 5, 2015

(54) METHODS AND SYSTEMS FOR PRESENTING A COMBINATION TREATMENT

(75) Inventors: Roderick A. Hyde, Redmond, WA (US); Muriel Y. Ishikawa, Livermore, CA (US); Eric C. Leuthardt, St. Louis, MO (US); Royce A. Levien, Lexington, MA (US); Robert W. Lord, Seattle, WA (US); Mark A. Malamud, Seattle, WA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 895 days.

(21) Appl. No.: 12/290,456

(22) Filed: Oct. 29, 2008

(65) Prior Publication Data
US 2009/0271219 A1    Oct. 29, 2009

Related U.S. Application Data

(63) Continuation-in-part of application No. 12/150,122, filed on Apr. 24, 2008, and a continuation-in-part of application No. 12/152,266, filed on May 13, 2008, now abandoned, and a continuation-in-part of
(Continued)

(51) Int. Cl.
G06F 19/00    (2011.01)
G06Q 50/22   (2012.01)
G06Q 50/24   (2012.01)

(52) U.S. Cl.
CPC .............. *G06Q 50/22* (2013.01); *G06F 19/345* (2013.01); *G06F 19/3456* (2013.01); *G06Q 50/24* (2013.01)

(58) Field of Classification Search
USPC ........................................... 702/19, 182–185
See application file for complete search history.

(56) References Cited

U.S. PATENT DOCUMENTS

| 3,036,568 | A | 5/1962 | Stark |
| 4,570,640 | A | 2/1986 | Barsa |
| 4,734,585 | A | 3/1988 | Owers |
| 4,755,043 | A | 7/1988 | Carter |
| 4,962,491 | A | 10/1990 | Schaeffer |
| 4,973,149 | A | 11/1990 | Hutchinson |
| 4,974,729 | A | 12/1990 | Steinnagel |
| 5,099,463 | A | 3/1992 | Lloyd et al. |
| 5,135,752 | A | 8/1992 | Snipes |
| 5,200,891 | A | 4/1993 | Kehr et al. |

(Continued)

FOREIGN PATENT DOCUMENTS

| WO | WO 03/048789 A2 | 6/2003 |
| WO | WO03/048789 | 12/2003 |

(Continued)

OTHER PUBLICATIONS

U.S. Appl. No. 12/315,366, Hyde et al.
(Continued)

*Primary Examiner* — Edward Raymond

(57) ABSTRACT

Methods, computer program products, and systems are described that include accepting an indication of an individual's compliance with an artificial sensory experience and presenting an indication of a bioactive agent at least partly based on the indication of the individual's compliance with the artificial sensory experience.

34 Claims, 48 Drawing Sheets

Related U.S. Application Data application No. 12/154,275, filed on May 21, 2008, now Pat. No. 7,974,787, and a continuation-in-part of application No. 12/156,440, filed on May 30, 2008, and a continuation-in-part of application No. 12/156,949, filed on Jun. 5, 2008, and a continuation-in-part of application No. 12/157,160, filed on Jun. 6, 2008, now Pat. No. 8,876,688, and a continuation-in-part of application No. 12/157,922, filed on Jun. 13, 2008, and a continuation-in-part of application No. 12/157,989, filed on Jun. 13, 2008, and a continuation-in-part of application No. 12/214,547, filed on Jun. 19, 2008, now Pat. No. 7,801,686, and a continuation-in-part of application No. 12/217,509, filed on Jul. 3, 2008, and a continuation-in-part of application No. 12/217,620, filed on Jul. 7, 2008, now Pat. No. 8,606,592, and a continuation-in-part of application No. 12/218,503, filed on Jul. 15, 2008, and a continuation-in-part of application No. 12/218,627, filed on Jul. 16, 2008, and a continuation-in-part of application No. 12/220,706, filed on Jul. 25, 2008, and a continuation-in-part of application No. 12/229,531, filed on Aug. 22, 2008, and a continuation-in-part of application No. 12/229,612, filed on Aug. 25, 2008, now abandoned, and a continuation-in-part of application No. 12/283,619, filed on Sep. 12, 2008, now Pat. No. 8,930,208, and a continuation-in-part of application No. 12/283,742, filed on Sep. 15, 2008, now Pat. No. 8,615,407, and a continuation-in-part of application No. 12/286,751, filed on Sep. 30, 2008, and a continuation-in-part of application No. 12/286,730, filed on Sep. 30, 2008, and a continuation-in-part of application No. 12/287,686, filed on Oct. 10, 2008, and a continuation-in-part of application No. 12/287,886, filed on Oct. 14, 2008, and a continuation-in-part of application No. 12/290,227, filed on Oct. 28, 2008.

(56) References Cited

U.S. PATENT DOCUMENTS

| | | | |
|---|---|---|---|
| 5,277,188 A | 1/1994 | Selker | |
| 5,348,268 A | 9/1994 | Klein | |
| 5,408,443 A | 4/1995 | Weinberger | |
| 5,463,564 A | 10/1995 | Agrafiotis et al. | |
| 5,508,042 A | 4/1996 | Oshlack et al. | |
| 5,577,981 A | 11/1996 | Jarvik | |
| 5,610,674 A | 3/1997 | Martin | |
| 5,645,072 A | 7/1997 | Thrall et al. | |
| 5,671,752 A | 9/1997 | Sinderby et al. | |
| 5,722,754 A | 3/1998 | Langner | |
| 5,724,983 A | 3/1998 | Selker et al. | |
| 5,725,472 A | 3/1998 | Weathers | |
| 5,822,726 A | 10/1998 | Taylor et al. | |
| 5,845,255 A | 12/1998 | Mayaud | |
| 5,846,086 A | 12/1998 | Bizzi et al. | |
| 5,891,049 A | 4/1999 | Cyrus et al. | |
| 5,919,141 A | 7/1999 | Money et al. | |
| 6,053,866 A | 4/2000 | McLeod | |
| 6,067,523 A | 5/2000 | Bair et al. | |
| 6,102,846 A | 8/2000 | Patton et al. | |
| 6,149,586 A | 11/2000 | Elkind | |
| 6,152,563 A | 11/2000 | Hutchinson et al. | |
| 6,168,562 B1 | 1/2001 | Miller et al. | |
| 6,186,145 B1 | 2/2001 | Brown | |
| 6,198,953 B1 | 3/2001 | Webster et al. | |
| 6,244,987 B1 | 6/2001 | Ohsuga et al. | |
| 6,282,458 B1 | 8/2001 | Murayama et al. | |
| 6,314,384 B1 | 11/2001 | Goetz | |
| 6,315,719 B1 | 11/2001 | Rode et al. | |
| 6,334,778 B1 | 1/2002 | Brown | |
| 6,368,111 B2 | 4/2002 | Legarda | |
| 6,383,135 B1 | 5/2002 | Chikovani et al. | |
| 6,390,453 B1 | 5/2002 | Frederickson et al. | |
| 6,397,080 B1 | 5/2002 | Viktorsson et al. | |
| 6,421,650 B1 | 7/2002 | Goetz et al. | |
| 6,425,764 B1 | 7/2002 | Lamson | |
| 6,448,030 B1 | 9/2002 | Rust et al. | |
| 6,487,520 B1 | 11/2002 | Kurtzberg et al. | |
| 6,542,858 B1 | 4/2003 | Grass et al. | |
| 6,561,811 B2 | 5/2003 | Rapoza et al. | |
| 6,565,359 B2 | 5/2003 | Calhoun et al. | |
| 6,631,291 B2 | 10/2003 | Viertïo-Oja et al. | |
| 6,647,358 B2 | 11/2003 | Grass et al. | |
| 6,702,767 B1 | 3/2004 | Douglas et al. | |
| 6,723,527 B2 | 4/2004 | Pettit et al. | |
| 6,807,492 B2 | 10/2004 | Oren et al. | |
| 6,826,498 B2 | 11/2004 | Birkner et al. | |
| 6,832,178 B1 | 12/2004 | Fernandez et al. | |
| 6,852,069 B2 | 2/2005 | Park | |
| 6,886,653 B1 | 5/2005 | Bellehumeur | |
| 6,909,359 B1 | 6/2005 | McGovern | |
| 6,947,790 B2 | 9/2005 | Gevins et al. | |
| 6,952,695 B1 | 10/2005 | Trinks et al. | |
| 6,968,375 B1 | 11/2005 | Brown | |
| 6,997,880 B2 | 2/2006 | Carlebach et al. | |
| 7,002,476 B2 * | 2/2006 | Rapchak | 340/573.1 |
| 7,033,025 B2 | 4/2006 | Winterbotham | |
| 7,039,878 B2 | 5/2006 | Auer et al. | |
| 7,044,911 B2 | 5/2006 | Drinan et al. | |
| 7,049,103 B2 | 5/2006 | Ishiguro et al. | |
| 7,076,437 B1 | 7/2006 | Levy | |
| 7,084,874 B2 | 8/2006 | Kurzweil | |
| 7,144,680 B2 | 12/2006 | Park et al. | |
| 7,148,208 B2 | 12/2006 | Barkan et al. | |
| 7,161,579 B2 | 1/2007 | Daniel | |
| 7,177,675 B2 | 2/2007 | Suffin et al. | |
| 7,197,492 B2 | 3/2007 | Sullivan | |
| 7,198,044 B2 | 4/2007 | Trueba | |
| 7,226,164 B2 | 6/2007 | Abourizk et al. | |
| 7,229,288 B2 | 6/2007 | Stuart et al. | |
| 7,245,956 B2 | 7/2007 | Matthews et al. | |
| 7,272,431 B2 | 9/2007 | McGrath | |
| 7,294,107 B2 | 11/2007 | Simon et al. | |
| 7,353,065 B2 | 4/2008 | Morrell | |
| 7,461,651 B2 | 12/2008 | Brown | |
| 7,513,622 B2 | 4/2009 | Khaderi | |
| 7,575,865 B2 | 8/2009 | Leamon et al. | |
| 7,623,927 B2 | 11/2009 | Rezai | |
| 7,890,340 B2 | 2/2011 | Abraham-Fuchs et al. | |
| 8,150,629 B2 | 4/2012 | Geerts et al. | |
| 2001/0001144 A1 | 5/2001 | Kapp | |
| 2001/0010541 A1 * | 8/2001 | Fernandez et al. | 348/143 |
| 2002/0091546 A1 | 7/2002 | Christakis et al. | |
| 2002/0103428 A1 | 8/2002 | deCharms | |
| 2002/0103429 A1 | 8/2002 | deCharms | |
| 2002/0128061 A1 | 9/2002 | Blanco | |
| 2003/0036683 A1 | 2/2003 | Kehr et al. | |
| 2003/0077300 A1 | 4/2003 | Wermeling | |
| 2003/0144884 A1 | 7/2003 | Mayaud | |
| 2003/0214630 A1 | 11/2003 | Winterbotham | |
| 2003/0225362 A1 | 12/2003 | Currie et al. | |
| 2004/0024287 A1 | 2/2004 | Patton et al. | |
| 2004/0024616 A1 | 2/2004 | Spector et al. | |
| 2004/0078027 A1 | 4/2004 | Shachar | |
| 2004/0078239 A1 | 4/2004 | Dacosta | |
| 2004/0087576 A1 | 5/2004 | Haracz | |
| 2004/0092809 A1 | 5/2004 | DeCharms | |
| 2004/0123667 A1 | 7/2004 | McGrath | |
| 2004/0127778 A1 | 7/2004 | Lambert et al. | |
| 2004/0172285 A1 | 9/2004 | Gibson | |
| 2004/0196184 A1 | 10/2004 | Hollander et al. | |
| 2004/0208923 A1 | 10/2004 | Davis et al. | |
| 2005/0021372 A1 | 1/2005 | Mikkelsen et al. | |
| 2005/0054942 A1 | 3/2005 | Melker et al. | |
| 2005/0065813 A1 | 3/2005 | Mishelevich et al. | |
| 2005/0086077 A1 | 4/2005 | Forman | |
| 2005/0124851 A1 | 6/2005 | Patton et al. | |
| 2005/0124878 A1 | 6/2005 | Sharony | |
| 2005/0165115 A1 | 7/2005 | Murphy et al. | |

(56) References Cited

U.S. PATENT DOCUMENTS

| | | |
|---|---|---|
| 2005/0197654 A1 | 9/2005 | Edman et al. |
| 2005/0240084 A1 | 10/2005 | Morice et al. |
| 2005/0277911 A1 | 12/2005 | Stewart et al. |
| 2006/0031099 A1 | 2/2006 | Vitello et al. |
| 2006/0058694 A1 | 3/2006 | Clark et al. |
| 2006/0059145 A1 | 3/2006 | Henschke et al. |
| 2006/0062852 A1* | 3/2006 | Holmes .................... 424/484 |
| 2006/0084877 A1 | 4/2006 | Ujhazy et al. |
| 2006/0111644 A1 | 5/2006 | Guttag et al. |
| 2006/0161408 A1 | 7/2006 | Bachman et al. |
| 2006/0161456 A1 | 7/2006 | Baker et al. |
| 2006/0183980 A1 | 8/2006 | Yang |
| 2006/0235724 A1 | 10/2006 | Rosenthal |
| 2006/0241718 A1 | 10/2006 | Tyler et al. |
| 2006/0247489 A1 | 11/2006 | Carbis et al. |
| 2006/0252761 A1 | 11/2006 | Davis et al. |
| 2006/0265253 A1 | 11/2006 | Rao et al. |
| 2007/0016265 A1 | 1/2007 | Davoodi et al. |
| 2007/0067186 A1 | 3/2007 | Brenner et al. |
| 2007/0072821 A1 | 3/2007 | Iakoubova et al. |
| 2007/0088404 A1 | 4/2007 | Wyler et al. |
| 2007/0098778 A1 | 5/2007 | Borsadia |
| 2007/0112277 A1 | 5/2007 | Fischer et al. |
| 2007/0112624 A1 | 5/2007 | Jung et al. |
| 2007/0123783 A1 | 5/2007 | Chang |
| 2007/0136093 A1 | 6/2007 | Rankin et al. |
| 2007/0167853 A1 | 7/2007 | Melker et al. |
| 2007/0172814 A1 | 7/2007 | Li |
| 2007/0179534 A1 | 8/2007 | Firlik et al. |
| 2007/0191704 A1 | 8/2007 | DeCharms |
| 2008/0045832 A1 | 2/2008 | McGrath |
| 2008/0046286 A1 | 2/2008 | Halsted |
| 2008/0097167 A1 | 4/2008 | Yudkovitch et al. |
| 2008/0125978 A1 | 5/2008 | Robson et al. |
| 2008/0132383 A1* | 6/2008 | Einav et al. .................... 482/8 |
| 2008/0139870 A1 | 6/2008 | Gliner et al. |
| 2008/0139902 A1 | 6/2008 | Kotulla et al. |
| 2008/0146334 A1 | 6/2008 | Kil |
| 2008/0167571 A1 | 7/2008 | Gevins |
| 2008/0172044 A1 | 7/2008 | Shelton |
| 2008/0177197 A1 | 7/2008 | Lee et al. |
| 2008/0212847 A1 | 9/2008 | Davies et al. |
| 2008/0221847 A1 | 9/2008 | Fenetteau |
| 2008/0226730 A1 | 9/2008 | Schmitke et al. |
| 2008/0242947 A1 | 10/2008 | Jung et al. |
| 2008/0243544 A1 | 10/2008 | Cafer |
| 2008/0267447 A1 | 10/2008 | Kelusky et al. |
| 2008/0275731 A1 | 11/2008 | Rao et al. |
| 2008/0278682 A1 | 11/2008 | Huxlin et al. |
| 2008/0305518 A1 | 12/2008 | Klausen et al. |
| 2009/0171697 A1 | 7/2009 | Glauser et al. |
| 2009/0306741 A1 | 12/2009 | Hogle et al. |
| 2009/0312817 A1 | 12/2009 | Hogle et al. |
| 2010/0015184 A1 | 1/2010 | Tuel |
| 2010/0094202 A1 | 4/2010 | Edginton et al. |
| 2010/0163027 A1 | 7/2010 | Hyde et al. |
| 2010/0168525 A1 | 7/2010 | Hyde et al. |
| 2010/0168602 A1 | 7/2010 | Hyde et al. |
| 2010/0324874 A9 | 12/2010 | Bangs et al. |

FOREIGN PATENT DOCUMENTS

| | | |
|---|---|---|
| WO | WO2006/048417 | 5/2006 |
| WO | WO2007/016241 | 2/2007 |
| WO | WO 2007/141373 A2 | 12/2007 |

OTHER PUBLICATIONS

U.S. Appl. No. 12/315,072, Hyde et al.
Harland, C.J. et al.; "Electric potential probes—new directions in the remote sensing of the human body"; Measurement Science and Technology; bearing a date of 2002; pp. 163-169; vol. 13; Institute of Physics Publishing.
Barrientos, Ruth M. et al.; "Memory for context is impaired by injecting anisomycin into dorsal hippocampus following context exploration"; Behavioural Brain Research; bearing a date of Aug. 21, 2002; pp. 299-306; vol. 134, Issues 1-2; Elsevier Science B.V. (abstract only).
Grollman, Arthur P. ; "Inhibitors of Protein Biosynthesis"; The Journal of Biological Chemistry; bearing a date of Jul. 10, 1967; pp. 3266-3233; vol. 242, No. 13.
Kris Bosworth, et al., A computer-Based Violence Prevention Intervention for Young Adolescents: A Pilot Study, Adolescence, Winter 1998, pp. 785-796, vol. 33, No. 132, Publisher: Libra Publishers, Inc., Published in: US.
R.J. Prance, et al., Adaptive Elecric Potential Sensors for Smart Signal Acquisition and Processing, Journal of Physics: Conference Series 76, 2007, Publisher: IOP Publishing Ltd.
M.R. Smith, et al., A Data Extrapolation Algorithm Using a Complex Domain Neuralnetwork, Circuits and Systems II: Analog and Digital Signal Processing, IEEE Transactions on, Feb. 1997, pp. 143-147, vol. 44, No. 2.
Max Bayard, et al., Alcohol Withdrawal Syndrome, American Family Physician, Mar. 15, 2004, pp. 1443-1450, vol. 69, Published in: US.
Hunter G. Hoffman, et al., Analgesic Effects of Opioids and Immersive Virtual Reality Distraction: Evidence from Subjective and Functional Brain Image Assessments, Anesthesia & Analgesia, 2007, pp. 1776-1783, vol. 105, Published in: US.
Kohzoh Yoshino, et al., An algorithm for Detecting Startle State Based on Physiological Signals, Aug. 2006, Publisher: Elsevier Ltd.
D. Shaw, et al., Anxiolytic Effects of Lavender Oil Inhalation on Open-Field Behaviour in Rats, Phytomedicine, Mar. 19, 2007, pp. 613-620, vol. 14.
Laurent Jeanpierre, et al., Automated Medical Diagnosis with Fuzzy Stochastic Models: Monitoring Chronic Diseases, Acta Biotheoretica, 2004, pp. 291-311, vol. 52, No. 4, Publisher: Springer.
Xueliang Huo, et al., A Wireless Pharmaceutical Compliance Monitoring System Based on Magneto-Inductive Sensors, Sensors Journal, IEEE, Dec. 2007, pp. 1171-1719, vol. 7, No. 12, Published in: US.
Barbara Ortutay, Brain-Reading Headset to Sell for $299, Feb. 20, 2008, Publisher: Associated Press, Published in: US.
E. Grossman, et al., Breathing-Control lowers Blood Pressure, Journal of Human Hypertension, Apr. 2001, pp. 263-269, vol. 15, No. 4, Publisher: Nature Publishing Group.
Jennifer Vasterling, et al., Cognitive Distraction and Relaxation Training for the Control of Side Effects Due to Cancer Chemotherapy, Journal of Behavioral Medicine, Feb. 1993, pp. 65-80, vol. 16, No. 1, Publisher.
Robert E.L. Faris, Cultural Isolation and the Schizophrenic Personality, The American Journal of Sociology, Sep. 1934, pp. 155-164, vol. 40, No. 2, Publisher: University of Chicago Press, Published in: US.
Sandra L. Siedliecki, et al., Effect of Music on Power, Pain, Depression, and Disability, Journal of Advanced Nursing, Jan. 13, 2006, pp. 553-562, vol. 54, Publisher: Blackwell Publishing, Published in: US.
Maura Paul-Labrador, et al., Effects of a Randomized Controlled Trail of Transcendental Meditation on Components of the Metabolic Syndrome in Subjects With Coronary Artery Disease, Arch Intern Med, Jun. 12, 2006, pp. 1218-1224, vol. 166, Publisher: American Medical Society, Published in: US.
Igor Knez, Effects of Colour of Light on Nonvisual Psychological Processes, 6/01, pp. 201-208, vol. 21, No. 2, Publisher: Journal of Environmental Psychology, Published in: US.
C.J. Harland, et al., Elecrtric Potential Probes—New Directions in the Remote Sensing of the Human Body, Measurement Science and Technology, Dec. 21, 2001, Publisher: IOP Publishing Ltd., Published in: UK.
E. Glenn Schellenberg, et al., Exposure to Music and Cognitive Performance: Tests of Children and Adults, Psychology of Music, 2007, pp. 5-19, vol. 35, Published in: Canada.
C.J. Harland, et al., High Resolution Ambulatory Electrocardiographic Monitoring Using Wrist-Mounted Electric Potential Sensors, Measuring Science and Technology, May 23, 2003, Publisher: IOP Publishing Ltd., Published in: UK.
Leonid Skorin, Jr., How to Diagnose and Manage Headaches, Review of Optometry, Nov. 1999, pp. 73-76, vol. 136, Published in: US.

(56) References Cited

OTHER PUBLICATIONS

Sulaiman, et al., Human Motion Analysis Using Virtual Reality, Research and Development, 2007, SCOReD 2007, 5th Student Conference, Dec. 11-12, 2007, pp. 14, Published in: Selangor, Malayasia.

Dale A. Lawrence, et al., Human Perception of Friction in Haptic Interfaces, Proc. ASME Dynamic Systems and Control Division, Nov. 1998, pp. 287-294, vol. 64, Published in: US.

Peter Clarke, IBEC Has a Brain Wave: Feed EEG Emotion Back Into Games, EE Times online, Nov. 1, 2007, Publisher: http://www.eetimes.eu/design/202801063.

F.J. Canadas-Quesada, et al., Improvement of Perceived Stiffness Using Auditory Stimuli in Haptic Virtual Reality, IEEE Melecon, May 16-19, 2006, Published in: Benalmadena, Spain.

Morishita et al., Induction of Mania in Depression by Paroxetine, Human Psychopharmacol, Oct. 2003, pp. 565-568, vol. 18, No. 7.

J.N. Cohn, Introduction to Surrogate Markers, Circulation, 2004, pp. IV20-IV21, vol. 109, Publisher: American Heart Association, Published in: US.

Kuan Zhang, et al., Measurement of Human Daily Physical Activity, Obesity Research, Jan. 1, 2003, pp. 33-40, vol. 11, No. 1, Published in: US.

Sander Greenland, et al., Methods for Trend Estimation from Summarized Dose-Response Data, with Applications to Meta-Analysis, American Journal of Epidemiology, 1992, pp. 1301-1309, vol. 135, No. 11, Published in: US.

Russell N. Carney, et al., Mnemonic Instruction, With a Focus on Transfer, Dec. 2000, pp. 783-790, vol. 92, Publisher: Journal of Educational Psychology, Published in: US.

Fernando Patolsky, et al., Nanowire Sensors for Medicine and the Life Sciences, Future Medicine, Jun. 2006, pp. 51-65, vol. 1, No. 1, Published in: US.

M.R. Basso, Jr., Neurobiological Relationships Between Ambient Lighting and the Startle Response to Acoustic Stress in Humans, Sep. 2001, pp. 147-157, vol. 110, No. 3-4, Publisher: International Journal of Neuroscience, Published in: US.

New Horizons of Nerve Repair: Biomedical Engineer Trips Up Proteins in Nerve Regeneration System, Science Daily, Jul. 26, 2002, Publisher: http:www.sciencedaily.com/releases/2002/07/020725082253.htm, Published in: US.

New Mini-Sensor May Have Biomedical and Security Applications, Physorg.com, Nov. 1, 2007, Publisher: http://www.physorg.com/news113151078.html, Published in: US.

Luc Marlier, et al., Olfactory Stimulation Prevents Apnea in Premature Newborns, Pediatrics, Jan. 3, 2005, pp. 83-88, vol. 115, No. 1, Published in: US.

T. Green, et al., PC-Based Medical Data Acquisition and Analysis, 1995, p. 159 Publisher: 8th IEEE Symposium on Computer-Based Medical Systems (CBMS '95), Published in: US.

Neda Gould, et al., Performance on a Virtual Reality Spatial Memory Navigation Task in Depressed Patients, American Journal of Psychiatry, Mar. 10, 2007, pp. 516-519, vol. 165, Published in: US.

Phosphodiesterase Isoenzymes as Pharmacological Targets in the Treatment of Male Erectile Dysfunction, World Journal of Urology, Feb. 2001, pp. 14-22, vol. 19, No. 1, Publisher: Springer Berlin/Heidelberg.

JM Jokiniitty, et al., Prediction of Blood Pressure Level and Need for Antihypertensive Medication: 10 Years of Follow-up, J. Hypertension, Jul. 2001, pp. 1193-1201, vol. 19, No. 7.

K. Yamada, et al., Prediction of Medication Noncompliance in Outpatients with Schizophrenia: 2-year follow-up study, Psychiatry Research, 2004, pp. 61-69, vol. 141, No. 1.

G. Parker, et al., Prediction of Response to Antidepressant Medication by a Sign-Based Index of Melancholia, Australian and New Zealand Journal of Psychiatry, 1993, pp. 56-61, vol. 27, No. 1.

Kozarek, et al., Prospective Trial using Virtual Vision as Distraction Technique in Patients Undergoing Gastric Laboratory Procedures, Gastroenterology Nursing, Jan. 1997, pp. 12-14, vol. 20, No. 1, Published in: US.

Jan A. Staessen, et al., Randomised Double-Blind Comparison of Placebo and Active Treatment for Older Patients With Isolated Systolic Hypertensio, The Lancet, Sep. 13, 1997, pp. 757-764, vol. 350, No. 9080.

C.J. Harland, et al., Remote Detection of Human Electroencephalograms Using Ultrahigh Input Impedance Electric Potential Sensors, Applied Physics Letters, Oct. 21, 2002, pp. 3284-3286, vol. 81, No. 17, Publisher: American Institute of Physics.

Axelrod, et al., Smoke and Mirrors: Gathering User Requirements for Emerging Affective Systems, Jun. 10, 2004, pp. 323-328, vol. 1, Publisher: 26th International Conference on Information Technology Interfaces, 2004.

Alan G. Sanfey, Social Decision-Making: Insights from Game Theory and Neuroscience, Science Magazine, Oct. 26, 2007, pp. 598-602, vol. 318, No. 5850, Published in: US.

Something in the Way He Moves, The Economist, Sep. 27, 2007, Publisher: http://www.economist.com/science/PrinterFriendly.cfm?story_id=9861412, Published in: US.

Raymond W. Lam, et al., The Can-SAD Study: A Randomized Controlled Trial of the Effectiveness of Light Therapy and Fluoxetine in Patients With Winter Season Affected Disorder, May 2006, pp. 805-812, vol. 163, Publisher: American Journal of Psychiatry, Published in: US.

F. Joseph McClernon, et al., The Effects of Controlled Deep Breathing on Smoking Withdrawal Symptoms in Dependent Smokers, ScienceDirect, Jun. 2004, pp. 765-772, vol. 29, No. 4, Publisher: Elsevier Ltd., Published in: US.

Jin-Lain Ming, et al., The Efficacy of Acupressure to Prevent Nausea and Vomiting in Post-Operative Patients, Journal of Advanced Nursing, Aug. 2002, pp. 343-351, vol. 39, No. 4, Published in: US.

Elizabeth Von Muggenthaler, The Felid Purr: A Bio-Mechanical Healing Mechanism, Sep. 18, 2006, Publisher: 12th International Conference on Low Frequency Noise and Vibration and its Control, Published in: Bristol, UK.

De Matthews, et al., Using and Understanding Medical Statistics, S. Karger Basel AG, 2007, pp. 111-127, Published in: US.

Shelley Wiechman Askay, Using Hypnosis for Spinal Cord Injury Pain Management, SCI Forum Report, Sep. 11, 2007, Publisher: http://sci.washington.edu/info/forums/reports/hypnosis_for_sci_pain.asp, Published in: US.

Video Game May Help Detect Depression, New Scientist, Mar. 10, 2007, p. 18 No. 2594, Published in: US.

Matthew M. Kurtz, et al., A Virtual Reality Apartment as a Measure of Medication Management Skills in Patients with Schizophrenia: A Pilot Study, Schizophrenia Bulletin, 2007, pp. 1162-1170, vol. 33, No. 5, Publisher: Oxford University Press, Published in: US.

Virtual Reality Games Used to Distract Young Burn Victims From Pain and Anxiety, Medical News Today, Sep. 29, 2007, Publisher: http://www.medicalnewstoday.com/articles/84055.php, Published in: US.

Roland Piquepaille, Virtual Reality Helps Diagnose Heart Defects, Dec. 28, 2005, Published in: US.

Virtual Reality Medical Center, Publisher: http://www.vrphobia.com/, Published in: US, printed Mar. 4, 2008.

Virtual Reality Pain Reduction, Human Interface Technology Lab (HTIL), Apr. 18, 2008, pp. 1-3, Publisher: http://httl.washington.edu/projects/vrpain/, Published in: US.

Hunter G. Hoffman, Virtual-Reality Therapy, Scientific American, Jul. 26, 2004, pp. 60-65, Published in: US.

Virtual-Reality Video Game Help Link Depression to Specific Brain Area, SciencyDaily, Mar. 2, 2007, Publisher: http://www.sciencedaily.com/releases/2007/03/070301100807.htm, Published in: US.

Albert Rizzo, et al., Virtual Therapeutic Environments with Haptics: An Interdisciplinary Approach for Developing Post-Stroke Rehabilitation S, CPSN 2005, Jun. 20-23, 2005, pp. 70-76, Publisher: Proceedings of the 2005 International Conference on Computers for People with Special needs, Published in: Las Vegas, Nevada.

Alessandra Gorini, et al., Virtual Worlds, Real Healing, Science, Dec. 7, 2007, p. 1549 vol. 318, No. 5856, Publisher: AAAS, Published in: US.

(56) References Cited

OTHER PUBLICATIONS

J.A. Spencer, et al., White Noise and Sleep Induction, Archives of Disease in Childhood, 1990, pp. 135-137, vol. 65, Publisher: BMJ Publishing Group, Published in: London.
U.S. Appl. No. 12/584,200, Leuthardt et al.
U.S. Appl. No. 12/584,129, Leuthardt et al.
U.S. Appl. No. 12/462,404, Leuthardt et al.
U.S. Appl. No. 12/462,344, Leuthardt et al.
U.S. Appl. No. 12/462,197, Leuthardt et al.
U.S. Appl. No. 12/462,129, Leuthardt et al.
U.S. Appl. No. 12/460,327, Leuthardt et al.
U.S. Appl. No. 12/460,252, Leuthardt et al.
U.S. Appl. No. 12/459,623, Leuthardt et al.
U.S. Appl. No. 12/459,493, Leuthardt et al.
U.S. Appl. No. 12/459,386, Leuthardt et al.
U.S. Appl. No. 12/459,287, Leuthardt et al.
U.S. Appl. No. 12/459,195, Leuthardt et al.
U.S. Appl. No. 12/459,029, Leuthardt et al.
U.S. Appl. No. 12/455,308, Leuthardt et al.
U.S. Appl. No. 12/455,148, Leuthardt et al.
U.S. Appl. No. 12/387,961, Leuthardt et al.
Difede, Joann, Ph.D. et al.; "Virtual Reality Exposure Therapy for World Trade Center Post-traumatic Stress Disorder: A Case Report"; CyberPsychology & Behavior; 2002; pp. 529-535; vol. 5, No. 6; CyberPsychology & Behavior.
Hollifield, Michael, MD et al.; "Integrating Therapies for Anxiety Disorders"; Psychiatric Annals; May 2006; pp. 329-338; vol. 36, No. 5.
Kuzma, John M., MD et al.: "Integrating Pharmacotherapy and Psychotherapy in the Management of Anxiety Disorders"; Current Psychiatry Reports; 2004; pp. 268-273; vol. 6; Current Science Inc.
Vaiva, Guillaume et al.; "Immediate Treatment with Propranolol Decreases Posttraumatic Stress Disorder Two Months after Trauma"; Biological Psychiatry; 2003; pp. 947-949; vol. 54; Society of Biological Psychiatry.
Bonson, Katherine R.; "Hallucinogenic Drugs"; Encyclopedia of Life Sciences; bearing a date of 2001; pp. 1-7; Nature Publishing Group.
McKendree-Smith et al.; "Self-Administered Treatments for Depression: A Review"; Journal of Clinical Psychology; bearing a date of Mar. 2003; pp. 275-288; vol. 59, No. 3; Wiley Periodicals, Inc.
Pampallona et al; "Combined Pharmacotherapy and Psychological Treatment for Depression: A Systematic Review"; Arch Gen Psychiatry; bearing a date of Jul. 2004; pp. 714-719; vol. 61; American Medical Association.
"Seromycin-cycloserine capsule"; Physician's Desk Reference Digital Drug Database; bearing a revision date of Jun. 2007; pp. 1-5; PDR Network, LLC.
Davis, Michael et al.; "Combining Pharmacotherapy With Cognitive Behavioral Therapy: Traditional and New Approaches"; Journal of Traumatic Stress; bearing a date of Oct. 2006; pp. 571-581; vol. 19, No. 5; InterScience.
IEEE 100: The Authoritative Dictionary of IEEE Standards Terms, Seventh Edition; The Institute of Electrical and Electronics Engineering Press.
Munjack, Dennis J. et al.; "Alprazolam, Propranolol, and Placebo in the Treatment of Panic Disorder and Agoraphobia with Panic Attacks"; Journal of Clinical Psychopharmacology; bearing a date of 1989; pp. 22-27; vol. 9, No. 1; Williams and Wilkins Co.
Ressler, Kerry J. et al.; "Cognitive Enhancers as Adjuncts to Psychotherapy Use of D-Cycloserine in Phobic Individuals to Facilitate Extinction of Fear"; bearing a date of Nov. 2004; pp. 1136-1144; vol. 61; Arch Gen Psychiatry.
Rothbaum, Barbara O. et al.; "Applying Learning Principles to the Treatment of Post-Trauma Reactions"; Annals New York Academy of Sciences; bearing a date of 2003; pp. 112-121; vol. 1008; New York Academy of Sciences.
Wiederhold, Brenda K.; "The Use of Virtual Reality Technology in the Treatment of Anxiety Disorders"; Information Technologies in Medicine; bearing a date of 2001; pp. 19-37; vol. II; John Wiley & Sons, Inc.
Silva, Alcino J. et al.; "CREB and Memory"; Annu. Rev. Neurosci.; 1998; pp. 127-137; vol. 21; Annual Reviews Inc.
Baños et al.; "Virtual Reality Treatment of Flying Phobia"; IEEE Transactions on Information Technology in Biomedicine; Sep. 2002; pp. 206-212; vol. 6, No. 3; IEEE.
Coelho et al.; "*Research Article* Deconstructing Acrophobia: Physiological and Psychological Precursors to Developing a Fear of Heights"; Depression and Anxiety; bearing a date of Apr. 8, 2010; pp. 864-870; vol. 27; Wiley-Liss, Inc.
Mueller et al.; "Noradrenergic modulation of extinction learning and exposure therapy"; Behavioural Brain Research; bearing a date of Dec. 1, 2009; pp. 1-11; vol. 208; Elsevier B.V.
Rothbaum et al.; "A Controlled Study of Virtual Reality Exposure Therapy for the Fear of Flying"; Journal of Consulting and Clinical Psychology; bearing a date of May 4, 2000; pp. 1020-1026; vol. 68, No. 6; American Psychological Association, Inc.
Van Gerwen et al.; "People Who Seek Help for Fear of Flying: Typology of Flying Phobics"; Behavior Therapy; bearing a date of Mar. 11, 1997; pp. 237-251; vol. 28; Association for Advancement of Behavior Therapy.
Foa et al.; "Guidelines for Treatment of PTSD"; Journal of Traumatic Stress; 2000; pp. 539-588; vol. 13, No. 4; Reprinted with permission from "*Effective Treatments for PTSD*"; Foa et al.; Guilford Press.
Wiederhold et al.; "Fear of Flying: A Case Report Using Virtual Reality Therapy with Physiological Monitoring"; Cyber Psychology and Behavior; 1998; pp. 97-103; vol. 1, No. 2; Mary Ann Liebert, Inc.
"Alter" Excerpt from the Merriam-Webster English Dictionary; Printed on Jul. 8, 2013; total of 4 pages; Merriam-Webster Incorporated.
IEEE 100: The Authoritative Dictionary of IEEE Standards Terms, Seventh Edition; The Institute of Electrical and Electronics Engineering Press; Dec. 2000; 10 pages, ISBN 0-7381-2601-2; The Institute of Electrical and Electronics Engineers, Inc.; New York, NY.
Lehrner et al.; "Ambient odors of orange and lavender reduce anxiety and improve mood in a dental office"; Physiology & Behavior; Apr. 27, 2005; pp. 92-95; vol. 86; Elsevier Inc.
Beck et al.; "Virtual Reality Exposure Therapy for PTSD Symptoms After a Road Accident: An Uncontrolled Case Series"; Behavior Therapy; bearing a date of Sep. 22, 2006; pp. 39-48; vol. 38; Elsevier Ltd.
Garcia-Palacios et al.; "Virtual reality in the treatment of spider phobia: a controlled study"; Behaviour Research and Therapy; bearing a date of Jul. 1, 2001; pp. 983-993; vol. 40; Elsevier Science Ltd.
Vaiva et al.; "Fright (Effroi) and Other Peritraumatic Responses After a Serious Motor Vehicle Accident: Prospective Influence on Acute PTSD Development"; The Canadian Journal of Psychiatry-Original Research; bearing a date of Jul. 2003; pp. 395-401; vol. 48, No. 6.
Walshe et al.; "Exploring the Use of Computer Games and Virtual Reality in Exposure Therapy for Fear of Driving Following a Motor Vehicle Accident"; CyberPsychology & Behavior; bearing a date of 2003; pp. 329-334; vol. 6, No. 3; Mary Ann Liebert, Inc.
Wiederhold et al.; "Physiological Monitoring as an Objective Tool in Virtual Reality Therapy"; CyberPsychology & Behavior; bearing a date of 2002; pp. 77-82; vol. 5, No. 1; Mary Ann Liebert, Inc.
Moss et al.; "Aromas of Rosemary and Lavender Essential Oils Differentially Affect Cognition and Mood in Healthy Adults"; Intern. J. Neuroscience; bearing a date of Jul. 24, 2002; pp. 15-38; vol. 113; Taylor & Francis.
Chu et al.; "Proust nose best: Odors are better cues of autobiographical memory"; Memory & Cognition; bearing a date of Jan. 23, 2002; pp. 511-518; vol. 30, No. 4; Psychonomic Society, Inc.
Gerardi et al.; "Virtual Reality Exposure Therapy Using a Virtual Iraq: Case Report"; Journal of Traumatic Stress; Apr. 2008; pp. 209-213; vol. 21, No. 2; 2008 International Society for Traumatic Stress Studies.

\* cited by examiner

METHODS AND SYSTEMS FOR PRESENTING A COMBINATION TREATMENT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application entitled COMBINATION TREATMENT SELECTION METHODS AND SYSTEMS, naming Roderick A. Hyde; Muriel Y. Ishikawa; Eric C. Leuthardt; Royce A. Levien; Robert W. Lord; Mark A. Malamud; Elizabeth A. Sweeney; Lowell L. Wood, Jr.; and Victoria Y. H. Wood as inventors, filed Apr. 24, 2008, application Ser. No. 12/150,122, which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 13, 2008, application Ser. No. 12/152,266, now abandoned which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 21, 2008, application Ser. No. 12/154,275, now U.S. Pat. No. 7,974,787 which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 30, 2008, application Ser. No. 12/156,440, which is currently co-pending, or is an application of which a currently co-pending application is entitled to the benefit of the filing date.

For purposes of the USPTO extra-statutory requirements, the present application constitutes a continuation-in-part of U.S. patent application entitled SIDE EFFECT AMELIORATING COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 5, 2008, application Ser. No. 12/156,949, which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 6, 2008, application Ser. No. 12/157,160, which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT SELECTION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,922, which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,989, which is currently co-pending, or is an application of which a currently co-pending application is entitled to the benefit of the filing date.

For purposes of the USPTO extra-statutory requirements, the present application constitutes a continuation-in-part of U.S. patent application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 19, 2008, application Ser. No. 12/214,547, now U.S. Pat. No. 7,801,686 which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W.

LORD; MARK A. MALAMUD; ELIZABETH A. SWEENEY; LOWELL L. WOOD, JR.; AND VICTORIA Y. H. WOOD as inventors, filed Jul. 3, 2008, application Ser. No. 12/217,509, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 7, 2008, application Ser. No. 12/217,620, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 15, 2008, application Ser. No. 12/218,503, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 16, 2008, application Ser. No. 12/218,627, which is currently co-pending, or is an application of which a currently co-pending application is entitled to the benefit of the filing date.

For purposes of the USPTO extra-statutory requirements, the present application constitutes a continuation-in-part of U.S. patent application entitled SYSTEMS AND APPARATUS FOR MEASURING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 25, 2008, application Ser. No. 12/220,706, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MODIFYING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Aug. 22, 2008, application Ser. No. 12/229,531, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MODIFYING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Aug. 25, 2008, application Ser. No. 12/229,612, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR DETECTING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 12, 2008, application Ser. No. 12/283,619, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR DETECTING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 15, 2008, application Ser. No. 12/283,742, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 30, 2008, application Ser. No. 12/286,730, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 30, 2008, application Ser. No. 12/286,751, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD;

ELIZABETH A. SWEENEY; LOWELL L. WOOD, JR.; AND VICTORIA Y. H. WOOD as inventors, filed Oct. 10, 2008, application Ser. No. 12/287,686, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 14, 2008, application Ser. No. 12/287,886, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 28, 2008, application Ser. No. 12/290,227, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for combining a bioactive agent with an artificial sensory experience.

SUMMARY

In one aspect, a method includes but is not limited to accepting an indication of an individual's compliance with an artificial sensory experience and presenting an indication of a bioactive agent at least partly based on the indication of the individual's compliance with the artificial sensory experience. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting an indication of an individual's compliance with an artificial sensory experience and means for presenting an indication of a bioactive agent at least partly based on the indication of the individual's compliance with the artificial sensory experience. In addition to the foregoing, other method aspects are described in the claims, drawings, and text forming a part of the present disclosure.

In one aspect, a system includes but is not limited to circuitry for accepting an indication of an individual's compliance with an artificial sensory experience and circuitry for presenting an indication of a bioactive agent at least partly based on the indication of the individual's compliance with the artificial sensory experience. In addition to the foregoing, other method aspects are described in the claims, drawings, and text forming a part of the present disclosure.

In one aspect, a computer program product includes but is not limited to a signal-bearing medium bearing one or more instructions for accepting an indication of an individual's compliance with an artificial sensory experience, and one or more instructions for presenting an indication of a bioactive agent at least partly based on the indication of the individual's compliance with the artificial sensory experience. In addition to the foregoing, other method aspects are described in the claims, drawings, and text forming a part of the present disclosure.

In one aspect, a system includes but is not limited to a computing device and instructions that when executed on the computing device cause the computing device to accept an indication of an individual's compliance with an artificial sensory experience and present an indication of a bioactive agent at least partly based on the indication of the individual's compliance with the artificial sensory experience. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

DETAILED DESCRIPTION

Figure 1:
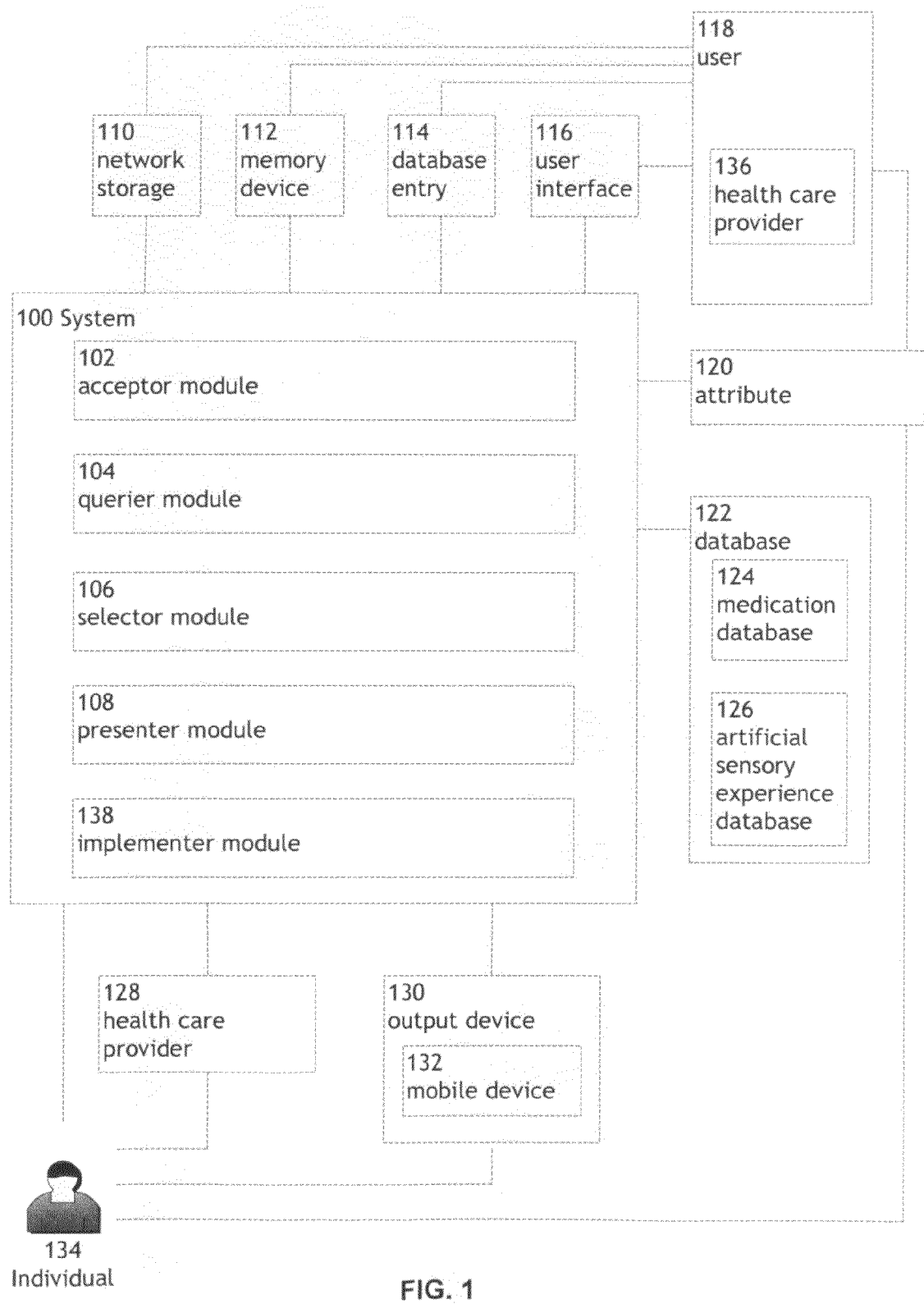
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The system 100 may include acceptor module 102, querier module 104, selector module 106, presenter module 108, implementer module 138, and/or modifier module 140. Acceptor module 102 may receive attribute 120 from network storage 110, memory device 112, database entry 114, and/or user interface 116. User interface 116 may receive information from user 118. User 118 may include health care provider 136. Querier module 104 may search database 122. Database 122 may include medication database 124 and/or artificial sensory experience database 126. Presenter module 108 may present to health care provider 128, output device 130, and/or individual 134. Output device 130 may include mobile device 132. Modifier module 140 may include restrictor module 142, granter module 144, alterer module 146, adder module 148, deleter module 150, and/or acceptor module 152. System 100 generally represents instrumentality for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The operations of accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual may be accomplished electronically, such as with a set of interconnected electrical components, an integrated circuit, and/or a computer processor.

Figure 2:
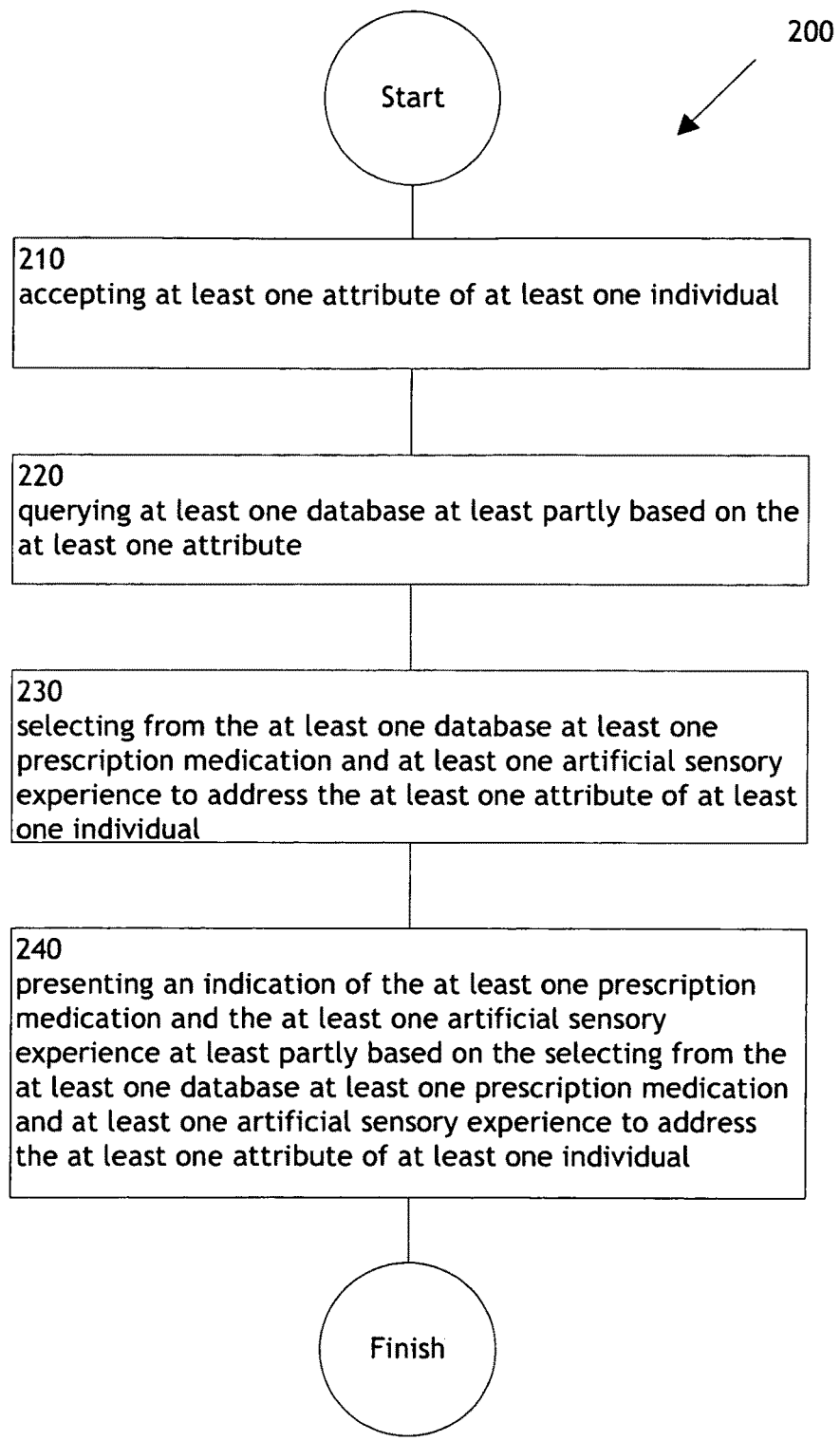
FIG. 2 illustrates an operational flow representing example operations related to selecting a combination of at least one prescription medication and at least one artificial sensory experience.

FIG. 2 illustrates an operational flow 200 representing example operations related to accepting at least one attribute of at least one individual, querying at least one database at least partly based on the at least one attribute, selecting from the at least one database at least one prescription medication and at least one artificial sensory experience to address the at least one attribute of at least one individual, and/or presenting an indication of the at least one prescription medication and the at least one artificial sensory experience at least partly based on the selecting from the at least one database at least one prescription medication and at least one artificial sensory experience to address the at least one attribute of at least one individual. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts accepting at least one attribute of at least one individual. For example, as shown in FIG. 1, acceptor module 102 may accept at least one attribute of at least one individual. In one instance, acceptor module 102 can accept from a user 118 and a user interface 116 an attribute 120 including an attribute of a personal health history associated with an individual named John Smith. In some instances, acceptor module 102 may include a computer processor.

Then, operation 220 depicts querying at least one database at least partly based on the at least one attribute. For example, as shown in FIG. 1, querier module 104 may search at least one database at least partly based on the at least one attribute. In one example and continuing with the previous example, querier module 104 can search a database 122 including a medication database 124 and artificial sensory experience database 126 at least partly based on the attribute including an attribute of a personal health history associated with an individual named John Smith. In some instances, querier module 104 may include a computer processor.

Then, operation 230 depicts selecting from the at least one database at least one prescription medication and at least one artificial sensory experience to address the at least one attribute of at least one individual. For example, as shown in FIG. 1, selector module 106 may select from the at least one database at least one prescription medication and at least one artificial sensory experience to address the at least one attribute of at least one individual. In one instance and continuing with the previous example, selector module 106 can select from a medication database 124 and artificial sensory experience database 126 a prescription medication and an artificial sensory experience for addressing the attribute 120 including an attribute of a personal health history associated with an individual named John Smith. In some instances, selector module 106 may include a computer processor.

Then, operation 240 depicts presenting an indication of the at least one prescription medication and the at least one artificial sensory experience at least partly based on the selecting from the at least one database at least one prescription medication and at least one artificial sensory experience to address the at least one attribute of at least one individual. For example, as shown in FIG. 1, presenter module 108 may present the at least one prescription medication and the at least one artificial sensory experience at least partly based on the searching at least one database at least partly based on the at least one attribute. In one instance and continuing with the previous example, presenter module 108 can present to a medical professional the prescription medication and the artificial sensory experience based on searching the medication database 124 and artificial sensory experience database 126 based on the at least one attribute 120 including an attribute of a personal health history associated with an individual named John Smith. In some instances, presenter module 108 may include a computer processor.

Figure 3:
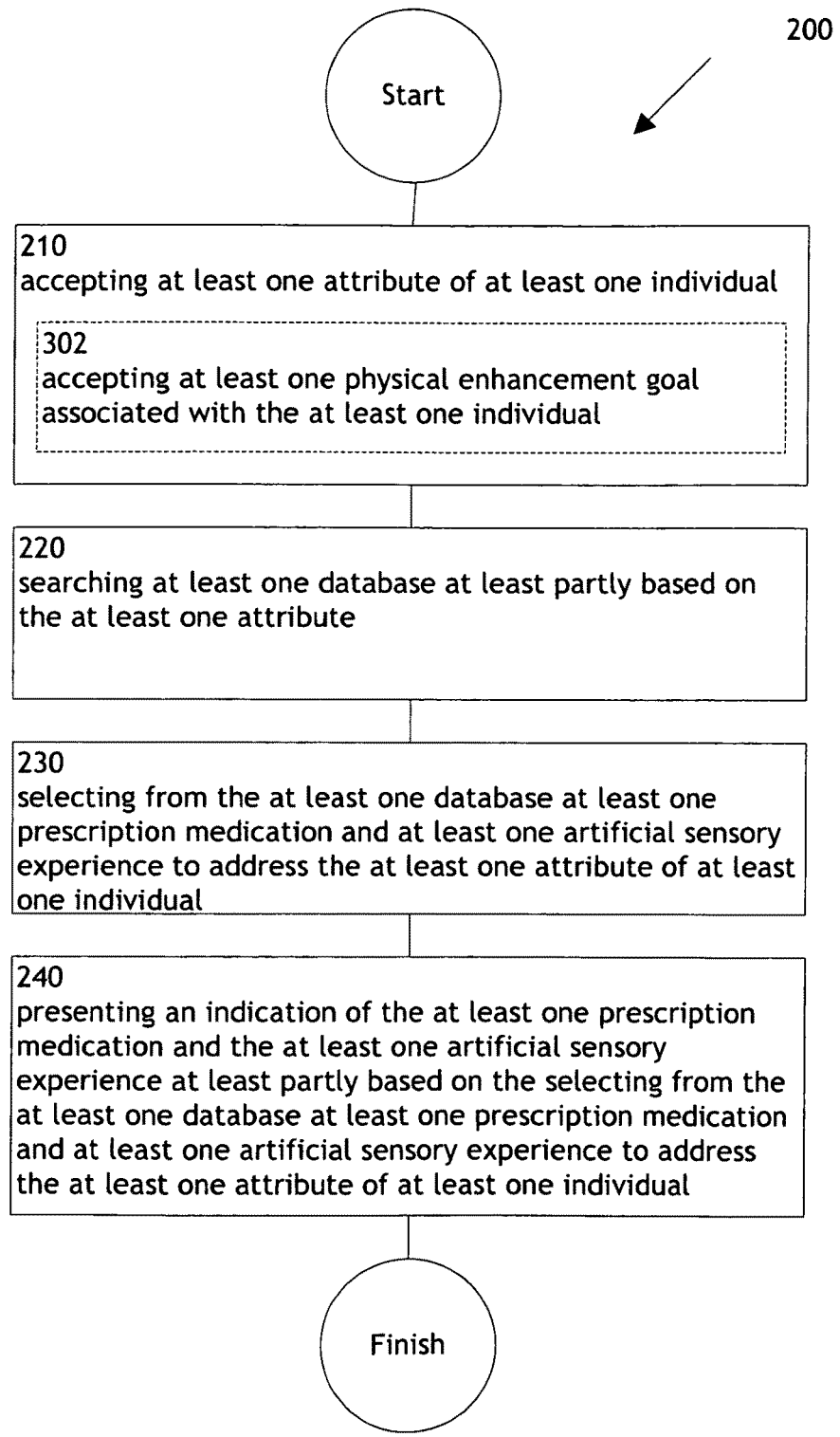
FIG. 3 illustrates an alternative embodiment of the operational flow of FIG. 2.

FIG. 3 illustrates alternative embodiments of the example operational flow 200 of FIG. 2. FIG. 3 illustrates example embodiments where the operation 210 may include at least one additional operation. Additional operations may include an operation 302.

Operation 302 illustrates accepting at least one physical enhancement goal associated with the at least one individual. For example, as shown in FIG. 1, acceptor module 102 may accept from a database entry 114 at least one physical enhancement goal associated with the at least one individual. In one instance and continuing with the above example, acceptor module 102 accepts from memory device 112 at least one physical enhancement goal associated with an individual named John Smith. A physical enhancement goal may include a physical state and/or situation an individual may plan to achieve. Some examples of a physical enhancement goal may include achieving a certain state of relaxation, reaching a certain body mass, maintaining a specific cholesterol level, achieving an athletic performance goal, and/or lowering a blood pressure level. In some instances, acceptor module 102 may include a computer processor.

Figure 4:
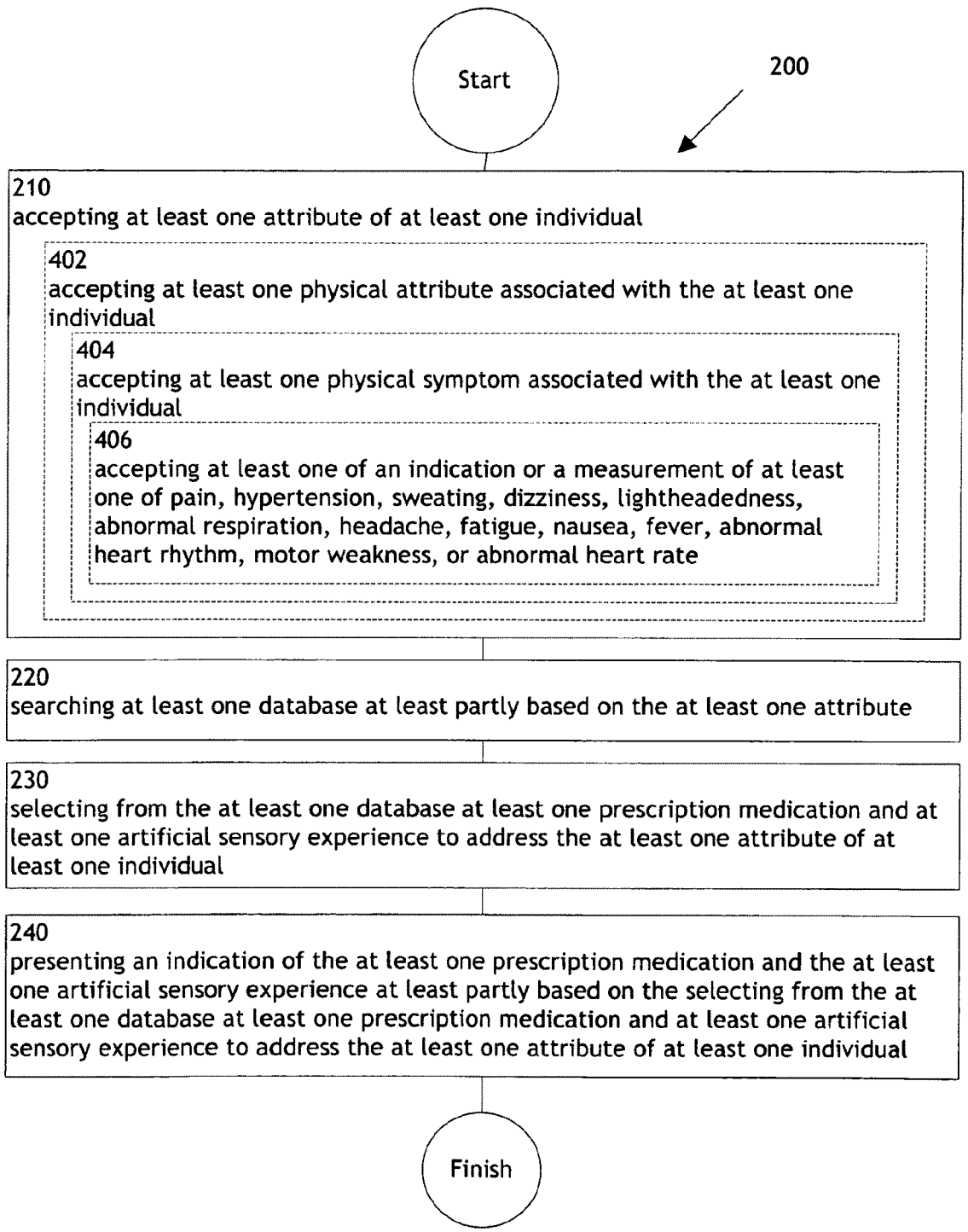
FIG. 4 illustrates an alternative embodiment of the operational flow of FIG. 2.

FIG. 4 illustrates alternative embodiments of the example operational flow 200 of FIG. 2. FIG. 4 illustrates example embodiments where the operation 210 may include at least one additional operation. Additional operations may include an operation 402, an operation 404, and/or an operation 406.

Operation 402 illustrates accepting at least one physical attribute associated with the at least one individual. For example, as shown in FIG. 1, acceptor module 102 may accept from network storage 110 at least one physical attribute associated with the at least one individual. In one instance, acceptor module 102 can accept a physical attribute 120 associated with a group of twenty individuals including an individual weight for each individual. A physical attribute may include an attribute that may be described and/or detected using senses, that has substance and/or a material existence, and/or that may be acted upon by physical force. Some examples of a physical attribute may include a biochemical measurement such as blood sugar level, a smell, an appearance, a physiological measurement such as blood pressure, and/or skin conductivity. In some instances, acceptor module 102 may include a computer processor.

Operation 404 illustrates accepting at least one physical symptom associated with the at least one individual. For example, as shown in FIG. 1, acceptor module 102 may accept at least one physical symptom associated with the at least one individual. In one example, acceptor module 102 can accept from a user 118 and/or user interface 116 a physical symptom including an indication of influenza such as a fever associated with an individual named Mark White. A physical symptom may include a manifestation, sign, and/or an indication of the presence of a disease and/or some other bodily disorder and/or abnormality. Some examples of a physical symptom may include pain, swelling, fever, rash, and/or discoloration. In some instances, acceptor module 102 may include a computer processor.

Operation 406 illustrates accepting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIG. 1, acceptor module 102 may accept from at least one of an indication or a measurement of at least one of pain, high blood pressure, sweating, dizziness, lightheadedness, abnormal respiration, headache, fatigue, nausea, fever, abnormal heart rhythm, motor weakness, or abnormal heart rate. In one example, acceptor module 102 can accept an indication of pain and a measurement of high blood pressure from network storage 110. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, acceptor module 102 may include a computer processor.

Figure 5:
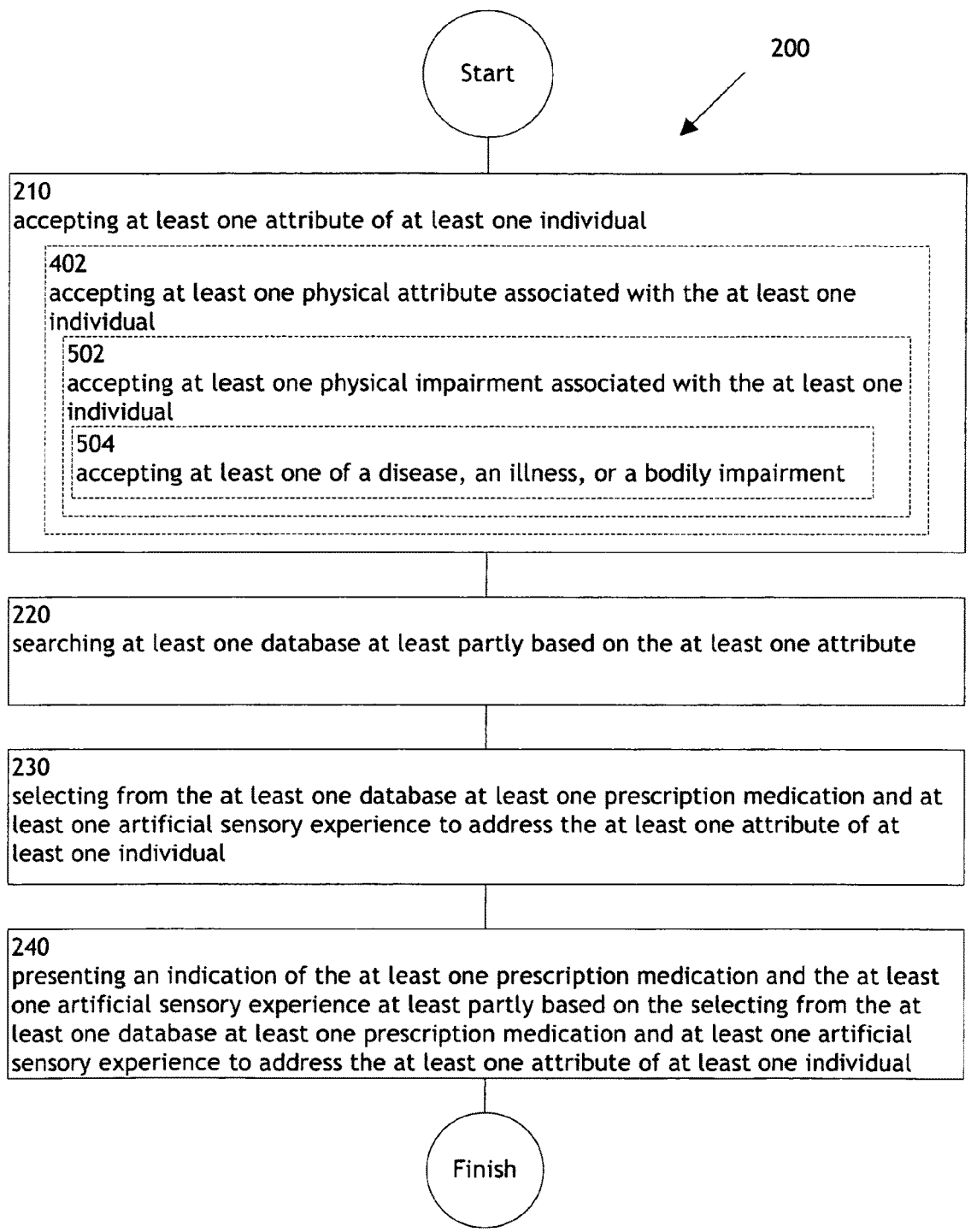
FIG. 5 illustrates an alternative embodiment of the operational flow of FIG. 2.

FIG. 5 illustrates alternative embodiments of the example operational flow 200 of FIG. 2. FIG. 5 illustrates example embodiments where the operation 210 may include at least one additional operation. Additional operations may include an operation 502, and/or an operation 504. Further, operation 502 illustrates accepting at least one physical impairment associated with the at least one individual. For example, as shown in FIG. 1, acceptor module 102 may accept at least one physical impairment associated with the at least one individual from a user 118 and a user interface 116. In one instance, acceptor module 102 accepts a physical impairment including a bodily impairment associated with an individual named Fred Johnson from a user 118 and/or a user interface 116. A physical impairment may include a condition or function judged to be significantly impaired relative to the usual standard of an individual of their group and may include physical impairment, sensory impairment, and/or disease. In some instances, acceptor module 102 may include a computer processor.

Operation 504 illustrates accepting at least one of a disease, an illness, or a bodily impairment. For example, as shown in FIG. 1, acceptor module 102 may accept at least one of a disease, an illness, or a bodily impairment. In one example, acceptor module 102 accepts an indication of a disease and a bodily impairment from database entry 114. A disease may include an abnormal condition of an organism that impairs bodily functions associated with one or more specific symptoms and signs and may include discomfort, distress, dysfunction, injury, a disorder, a syndrome, infection, and/or other atypical variation associated with structure and/or function of the body. An illness may include any state of poor health. Some examples of an illness may include cancer, the common cold, influenza, pneumonia, and/or high cholesterol. A bodily impairment may include a diminished ability in body function and/or structure. In some instances, acceptor module 102 may include a computer processor.

Figure 6:
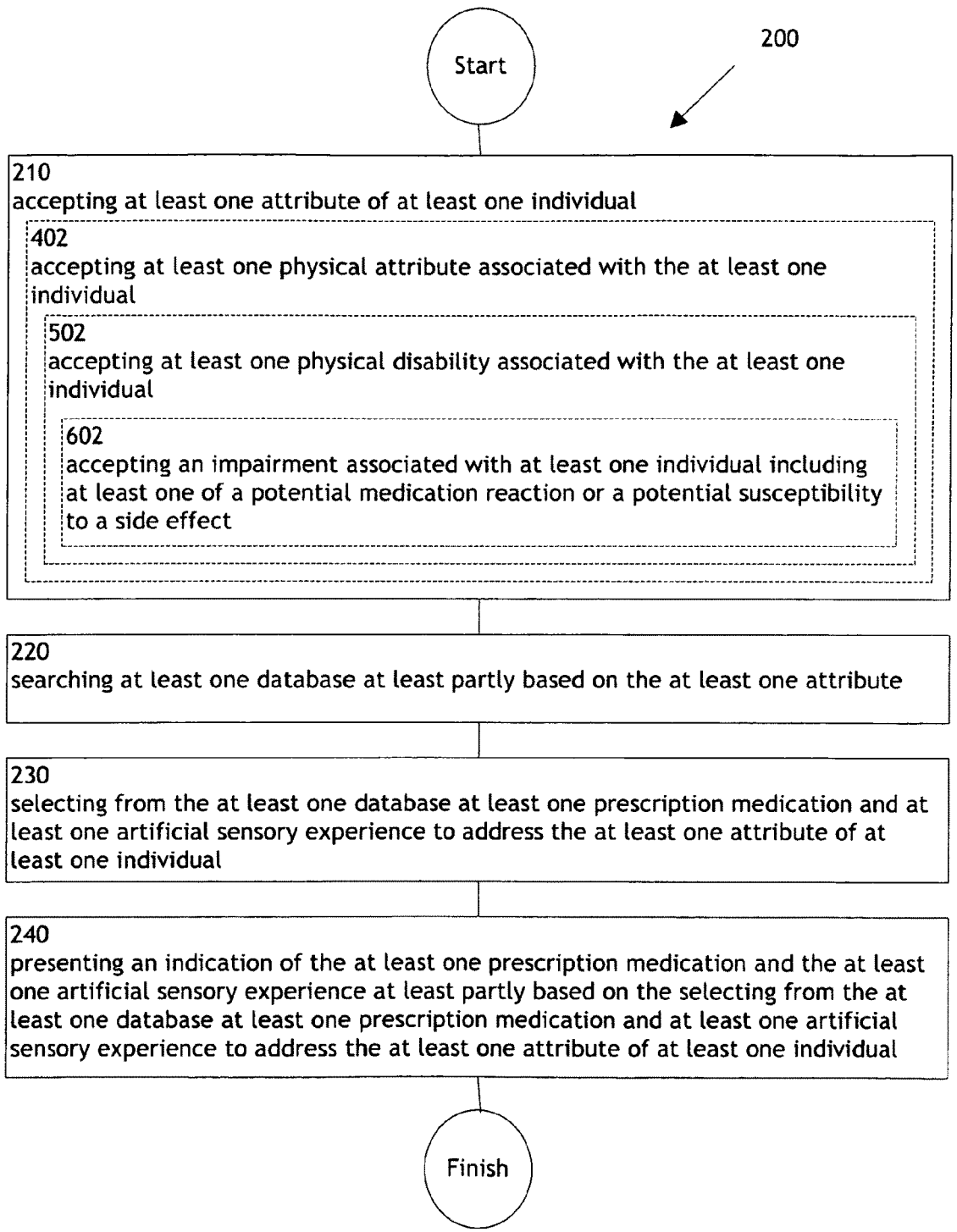
FIG. 6 illustrates an alternative embodiment of the operational flow of FIG. 2.

FIG. 6 illustrates alternative embodiments of the example operational flow 200 of FIG. 2. FIG. 6 illustrates example embodiments where operation 210 may include at least one additional operation. Additional operations may include an operation 602. Operation 602 illustrates accepting an impairment associated with at least one individual including at least one of a potential medication reaction or a potential susceptibility to a side effect. For example, as shown in FIG. 1, acceptor module 102 may accept an impairment associated with at least one individual including at least one of a potential medication reaction or a potential susceptibility to a side effect. In one example, acceptor module 102 can accept from network storage 110 an impairment associated with at least one individual including at least one of a potential medication reaction or a potential susceptibility to a side effect. A potential medication reaction may include a possible response a person may exhibit resulting from at least one drug and/or medication administered to the person. A potential medication reaction may include an allergy and/or a drug and/or medication interaction with a separate drug and/or medication. A potential susceptibility to a side effect may include the probability a certain person may be vulnerable to a side effect coupled with a specific drug and/or medication. In some instances, acceptor module 102 may include a computer processor.

Figure 7:
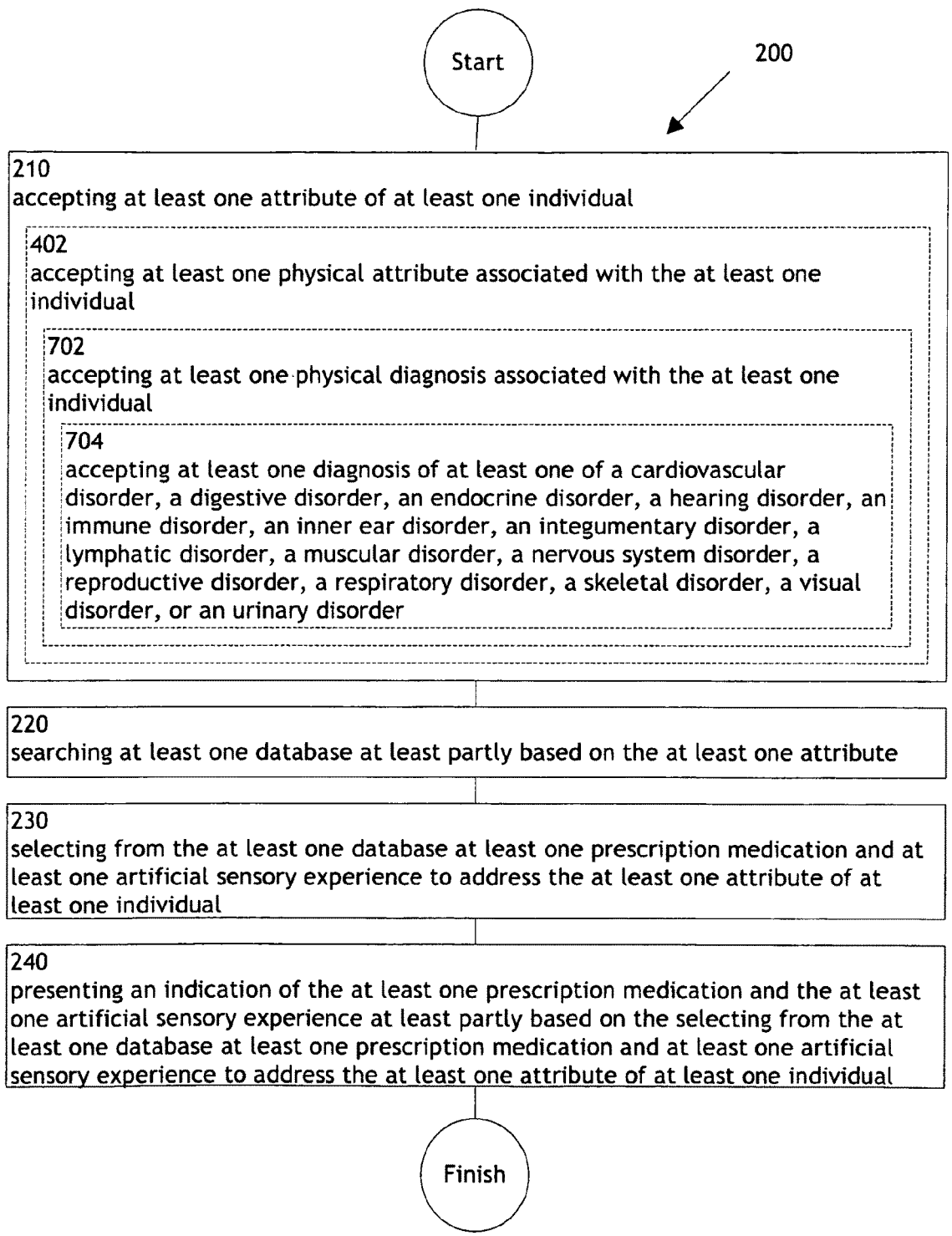
FIG. 7 illustrates an alternative embodiment of the operational flow of FIG. 2.

FIG. 7 illustrates alternative embodiments of the example operational flow 200 of FIG. 2. FIG. 7 illustrates example embodiments where the operation 210 may include at least one additional operation. Additional operations may include an operation 702, and/or an operation 704. Further, operation 702 illustrates accepting at least one physical diagnosis associated with the at least one individual. For example, as shown in FIG. 1, acceptor module 102 may accept at least one physical diagnosis associated with the at least one individual. In a specific example, acceptor module 102 accepts from memory device 112 a physical diagnosis associated with a group of ten individuals. A physical diagnosis may include identifying a disease and/or condition by its outward signs and/or symptoms. Some examples of a physical diagnosis may include identifying influenza and/or identifying Alzheimer's disease. In some instances, acceptor module 102 may include a computer processor.

Operation 704 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIG. 1, acceptor module 102 may accept at least one diagnosis of at least one of a cardiovascular disorder, a digestive disorder, an endocrine disorder, an integumentary disorder, a lymphatic disorder, a muscular disorder, a nervous system disorder, a reproductive disorder, a respiratory disorder, a skeletal disorder, or a urinary disorder. In a specific instance, acceptor module 102 can accept from user interface 116 and/or user 118 a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, stomach ulcers including those associated with *H. pylori* infection, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, loss due to death of auditory hair cells, for example that caused by trauma, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, acceptor module 102 may include a computer processor.

Figure 8:
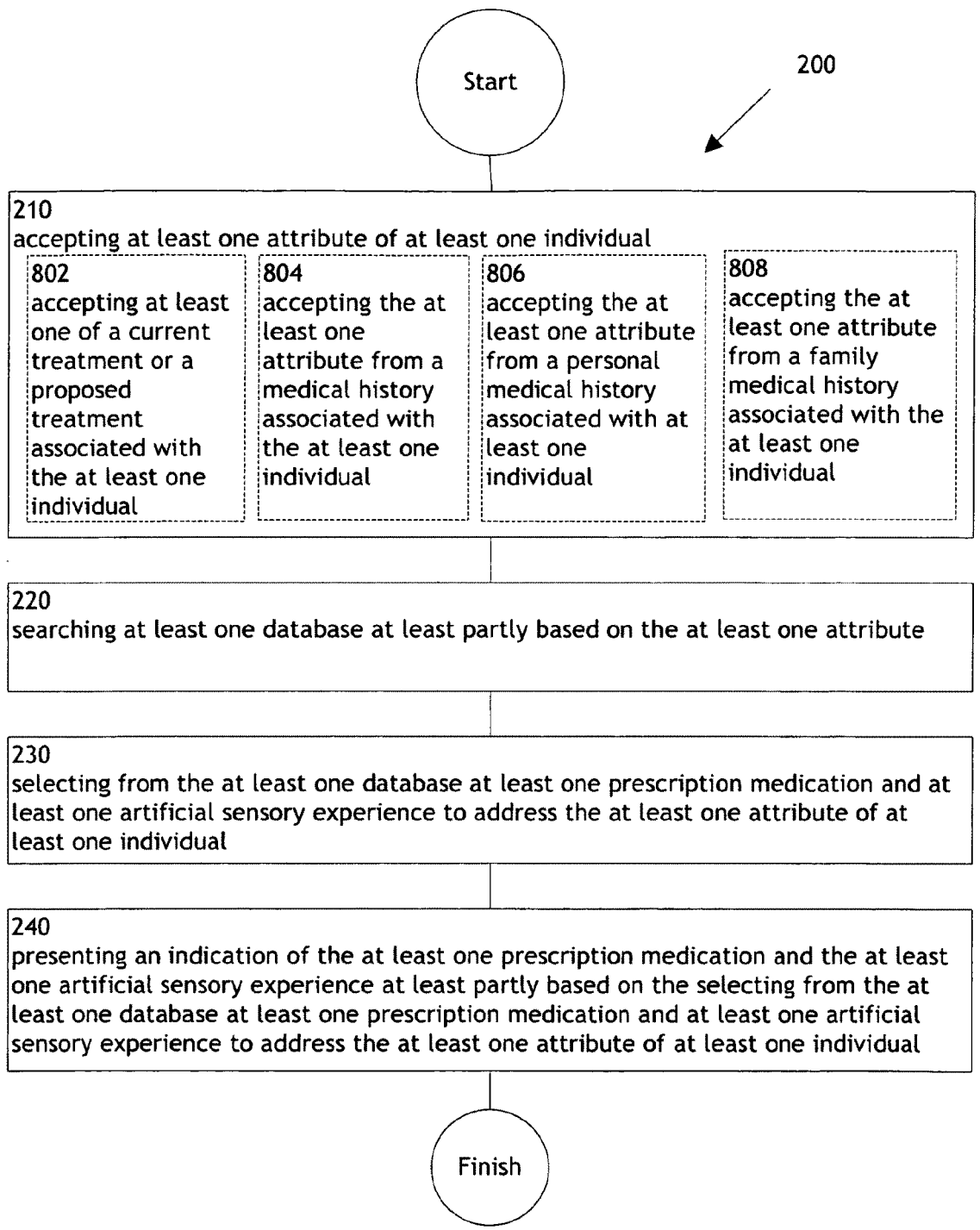
FIG. 8 illustrates an alternative embodiment of the operational flow of FIG. 2.

FIG. 8 illustrates alternative embodiments of the example operational flow 200 of FIG. 2. FIG. 8 illustrates example embodiments where the operation 210 may include at least one additional operation. Additional operations may include an operation 802, an operation 804, an operation 806, and/or operation 808.

Operation 802 illustrates accepting at least one of a current treatment or a proposed treatment associated with the at least one individual. For example, as shown in FIG. 1, acceptor module 102 may accept at least one of a current treatment or a proposed treatment associated with the at least one individual. In one instance, acceptor module 102 accepts a current treatment regime associated with an individual named Cathy Hansen. A current treatment may include one or a series of treatments recommended, administered, and/or prescribed for a certain individual. A proposed treatment may include one or a series of treatments recommended, prescribed, and/or not currently administered to a certain individual. In some instances, acceptor module 102 may include a computer processor.

Operation 804 illustrates accepting the at least one attribute from a medical history associated with the at least one individual. For example, as shown in FIG. 1, acceptor module 102 may accept the at least one attribute from a medical history associated with the at least one individual. In one example, acceptor module 102 may accept from database entry 114 an attribute 120 from a medical history including the number of blood relatives with diabetes associated with an individual named Emily Smith. A medical history may include a list of previous illnesses, symptoms, medicines, treatments, health risk factors, operations, and/or doctor visits for an individual and/or a relation of an individual. In some instances, acceptor module 102 may include a computer processor.

Operation 806 illustrates accepting the at least one attribute from a personal medical history associated with at least one individual. For example, as shown in FIG. 1, acceptor module 102 may accept the at least one attribute from a personal medical history associated with at least one individual. In a specific instance, acceptor module 102 can accept from database entry 114 an attribute 120 including, for example, a list of operations from a personal medical history associated with an individual named Robert Murphy. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, acceptor module 102 may include a computer processor.

Operation 808 illustrates accepting the at least one attribute from a family medical history associated with the at least one individual. For example, as shown in FIG. 1, acceptor module 102 may accept the at least one attribute from a family medical history associated with the at least one individual. In one example, acceptor module 102 can accept from network storage 110 an attribute 120 including a list of family members that have had ovarian cancer from a family medical history associated with an anonymous individual or an individual named Elizabeth Green. A family medical history may include a list of previous illnesses, symptoms, medicines, treatments, health risk factors, operations, and/or doctor visits associated with family members related to the at least one individual. In some instances, acceptor module 102 may include a computer processor.

Figure 9:
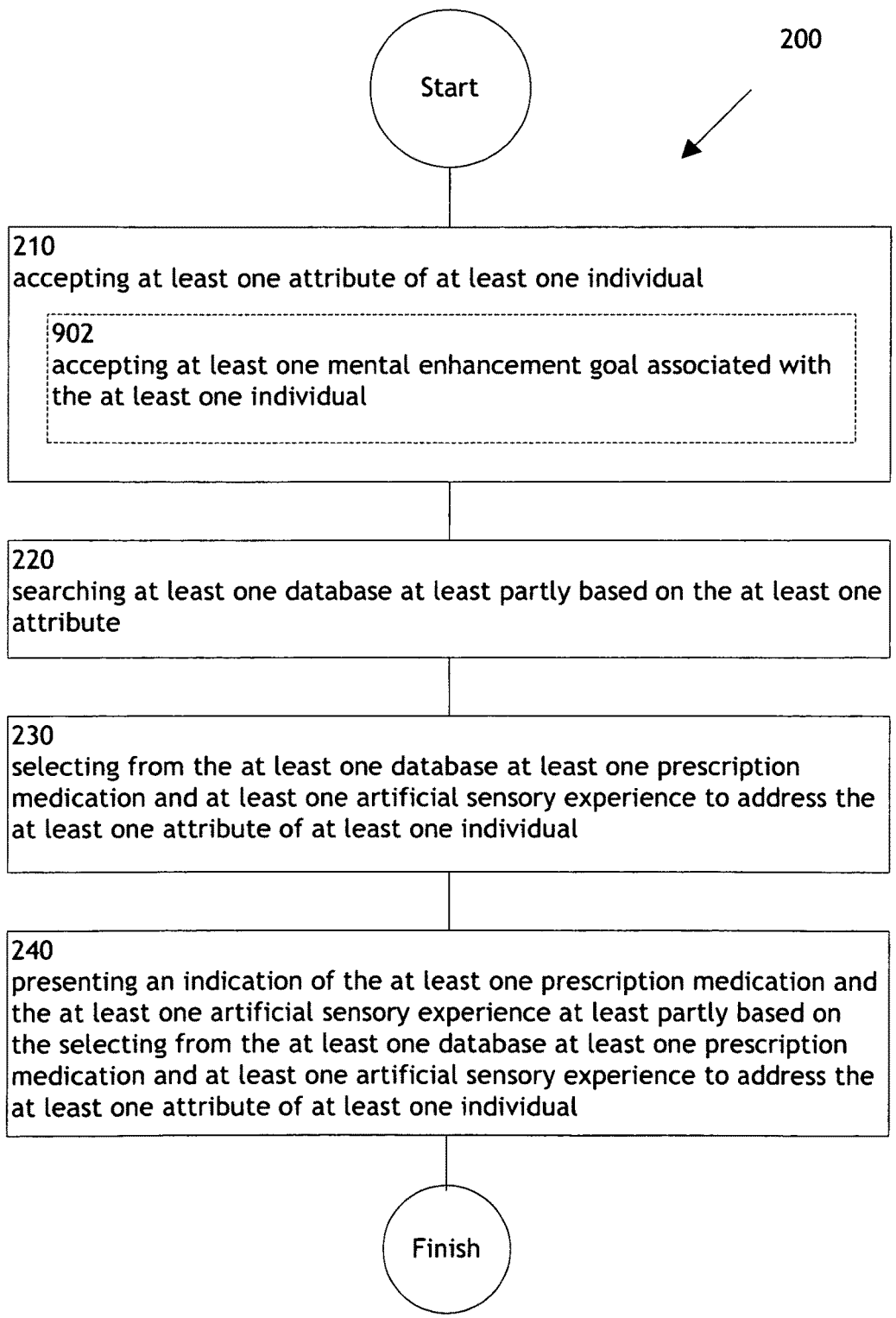
FIG. 9 illustrates an alternative embodiment of the operational flow of FIG. 2.

FIG. 9 illustrates alternative embodiments of the example operational flow 200 of FIG. 2. FIG. 9 illustrates example embodiments where operation 210 may include at least one additional operation. Additional operations may include an operation 902.

Operation 902 illustrates accepting at least one mental enhancement goal associated with the at least one individual. For example, as shown in FIG. 1, acceptor module 102 may accept at least one mental enhancement goal associated with the at least one individual. In one instance, acceptor module 102 can accept a mental enhancement goal associated with, for example, an individual named Dorothy Anderson. A mental enhancement goal may include a mental state and/or situation an individual may plan to achieve. Some examples of a mental enhancement goal may include achieving a certain state of mental awareness such as increased alertness or visual perception, reaching a certain cognitive capability such as enhanced memory or pattern recognition, maintaining a specific attention level, and/or reducing or eliminating a phobia. In some instances, acceptor module 102 may include a computer processor.

Figure 10:
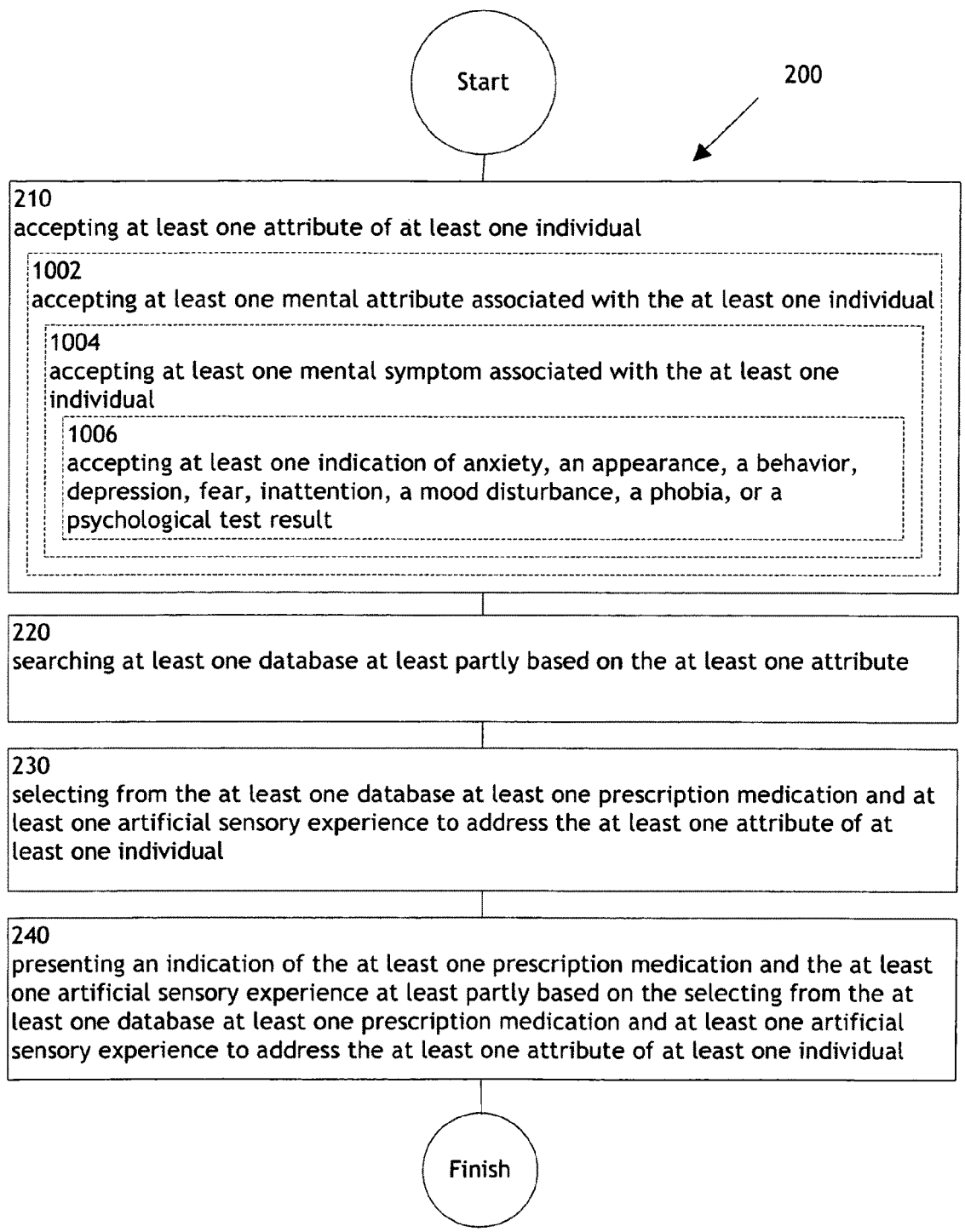
FIG. 10 illustrates an alternative embodiment of the operational flow of FIG. 2.

FIG. 10 illustrates alternative embodiments of the example operational flow 200 of FIG. 2. FIG. 10 illustrates example embodiments where operation 210 may include at least one additional operation. Additional operations may include an operation 1002, an operation 1004, and/or an operation 1006.

Operation 1002 illustrates accepting at least one mental attribute associated with the at least one individual. For example, as shown in FIG. 1, acceptor module 102 may accept at least one mental attribute associated with the at least one individual. In one example, acceptor module 102 can accept a mental attribute 120 including, for example, an intelligence quotient associated with an individual named Judy Peterson. A mental attribute may include an attribute that may be related to and/or associated with basic mental function and/or high-level brain function. Some examples of a mental attribute may include an intelligence quotient (IQ), measurements of brain activity for example using functional MRI or near infra-red technology, and/or measurements of mental development. In some instances, acceptor module 102 may include a computer processor.

Operation 1004 illustrates accepting at least one mental symptom associated with the at least one individual. For example, as shown in FIG. 1, acceptor module 102 may accept at least one mental symptom associated with the at least one individual. In one example, acceptor module 102 can accept from network storage 110 a mental symptom including a stress level measurement associated with an individual named Heather Swanson. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, acceptor module 102 may include a computer processor.

Operation 1006 illustrates accepting at least one indication of anxiety, an appearance, a behavior, depression, fear, inattention, a mood disturbance, a phobia, or a psychological test result. For example, as shown in FIG. 1, acceptor module 102 may accept at least one indication of anxiety, appearance, behavior, depression, fear, inattention, mood disturbance, phobia, or psychological test result. In one example, acceptor module 102 can accept from user interface 116 and user 118 an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, acceptor module 102 may include a computer processor.

Figure 11:
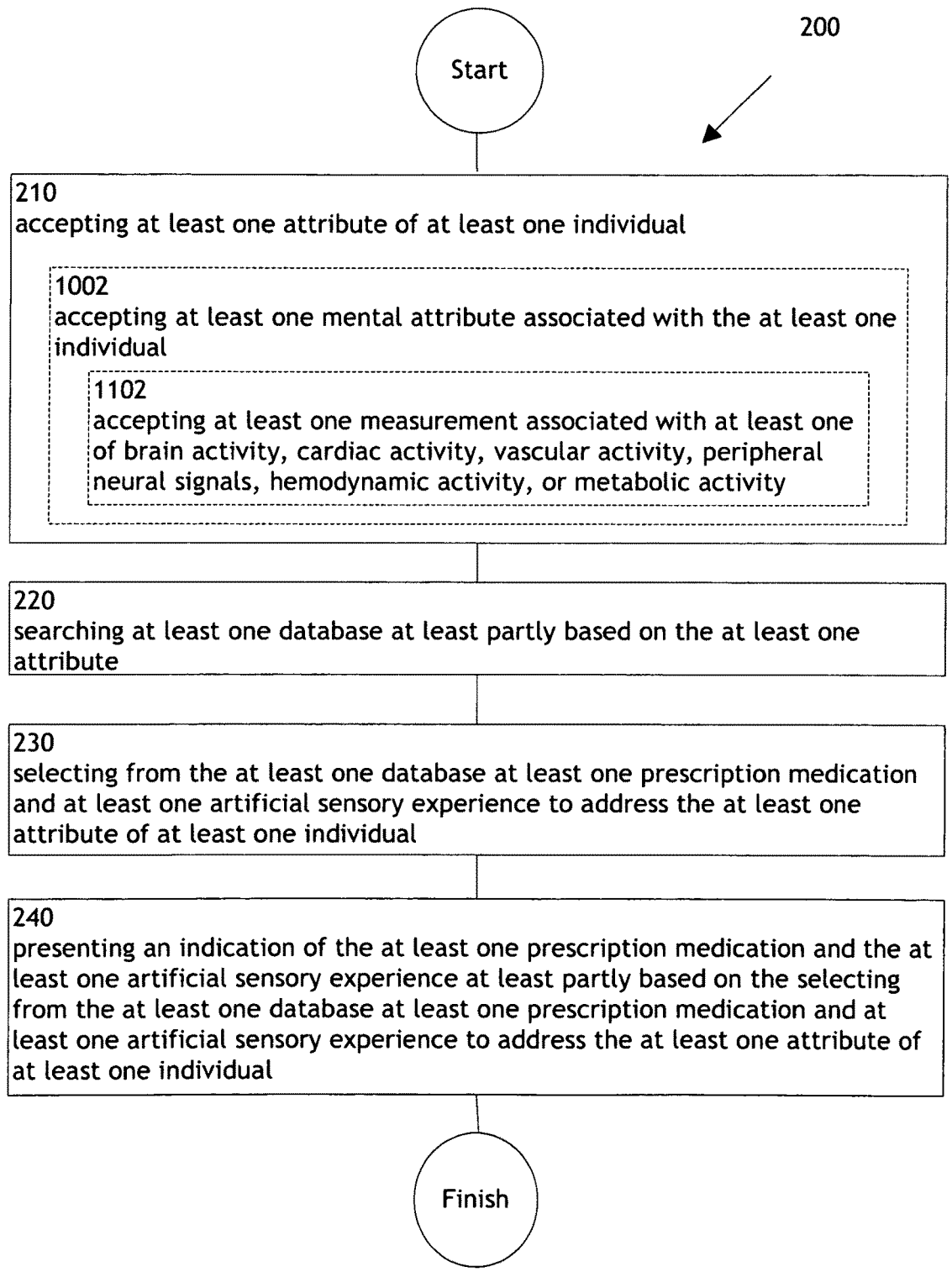
FIG. 11 illustrates an alternative embodiment of the operational flow of FIG. 2.

FIG. 11 illustrates alternative embodiments of the example operational flow 200 of FIG. 2. FIG. 11 illustrates example embodiments where operation 210 may include at least one additional operation. Additional operations may include an operation 1102.

Operation 1102 illustrates accepting at least one measurement associated with at least one of brain activity, cardiac activity, vascular activity, peripheral neural signals, hemodynamic activity, or metabolic activity. For example, as shown in FIG. 1, acceptor module 102 may accept at least one measurement associated with at least one of brain activity, cardiac activity, vascular activity, peripheral neural signals, hemodynamic activity, or metabolic activity. In one instance, acceptor module 102 can accept from database entry 114 a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, acceptor module 102 may include a computer processor.

Figure 12:
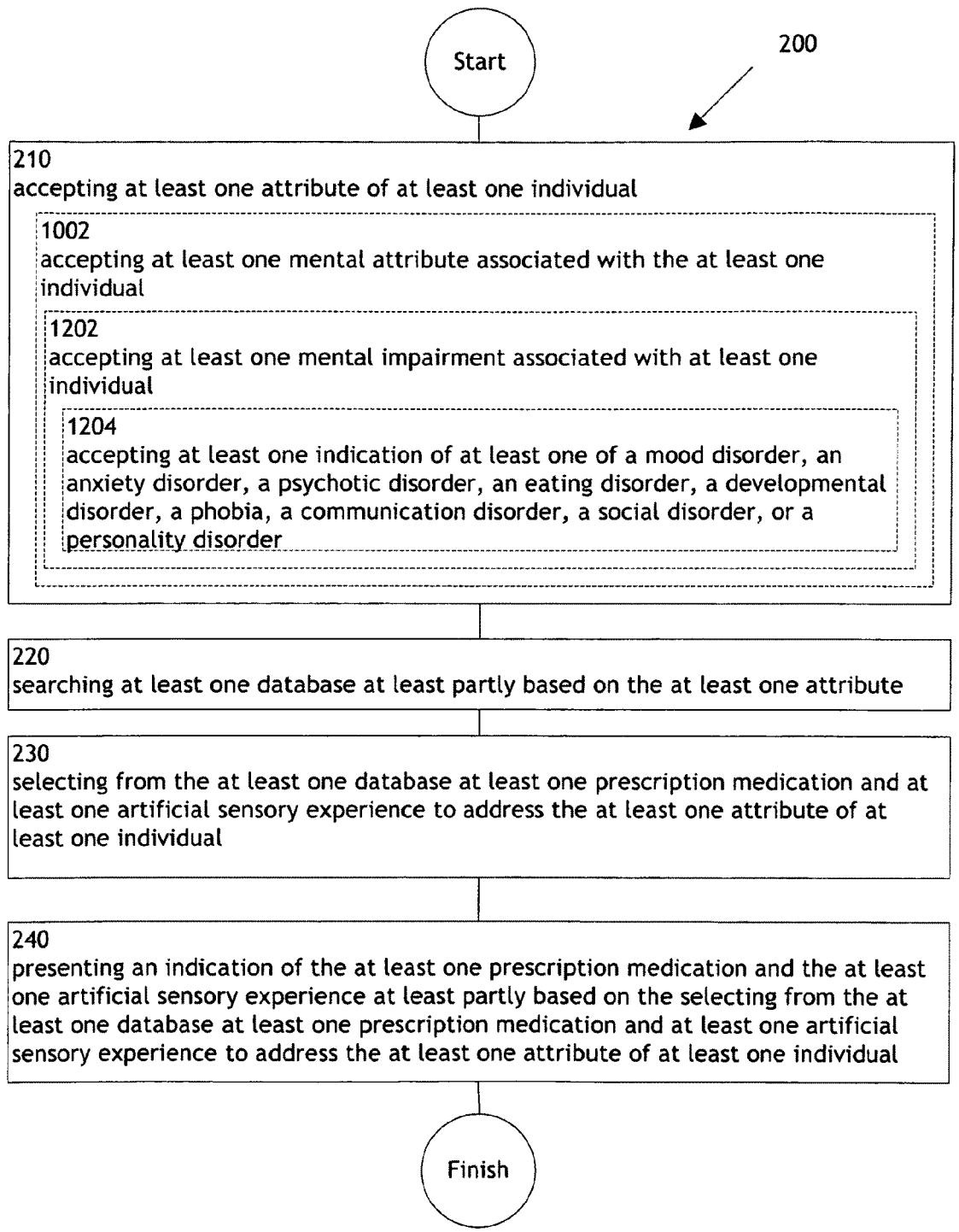
FIG. 12 illustrates an alternative embodiment of the operational flow of FIG. 2.

FIG. 12 illustrates alternative embodiments of the example operational flow 200 of FIG. 2. FIG. 12 illustrates example embodiments where operation 210 may include at least one additional operation. Additional operations may include an operation 1202, and/or an operation 1204.

Operation 1202 illustrates accepting at least one mental impairment associated with at least one individual. For example, as shown in FIG. 1, acceptor module 102 may accept at least one mental impairment associated with at least one individual. In one example, acceptor module 102 can accept from memory device 112 a mental impairment associated with an individual named Richard Lewis. A mental impairment may include a condition or function judged by a health care provider to be significantly impaired relative to the usual standard of an individual of their group, and may include mental impairment, sensory impairment, and/or mental disease. In some instances, acceptor module 102 may include a computer processor.

Operation 1204 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIG. 1, acceptor module 102 may accept at least one indication of at least one of a mood disorder, an anxiety disorder, a psychotic disorder, an eating disorder, a developmental disorder, a phobia, or a personality disorder. In one instance, acceptor module 102 can accept from user interface 116 and/or user 118 an indication of a mood disorder including a mood change and the onset of depression in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, acceptor module 102 may include a computer processor.

Figure 13:
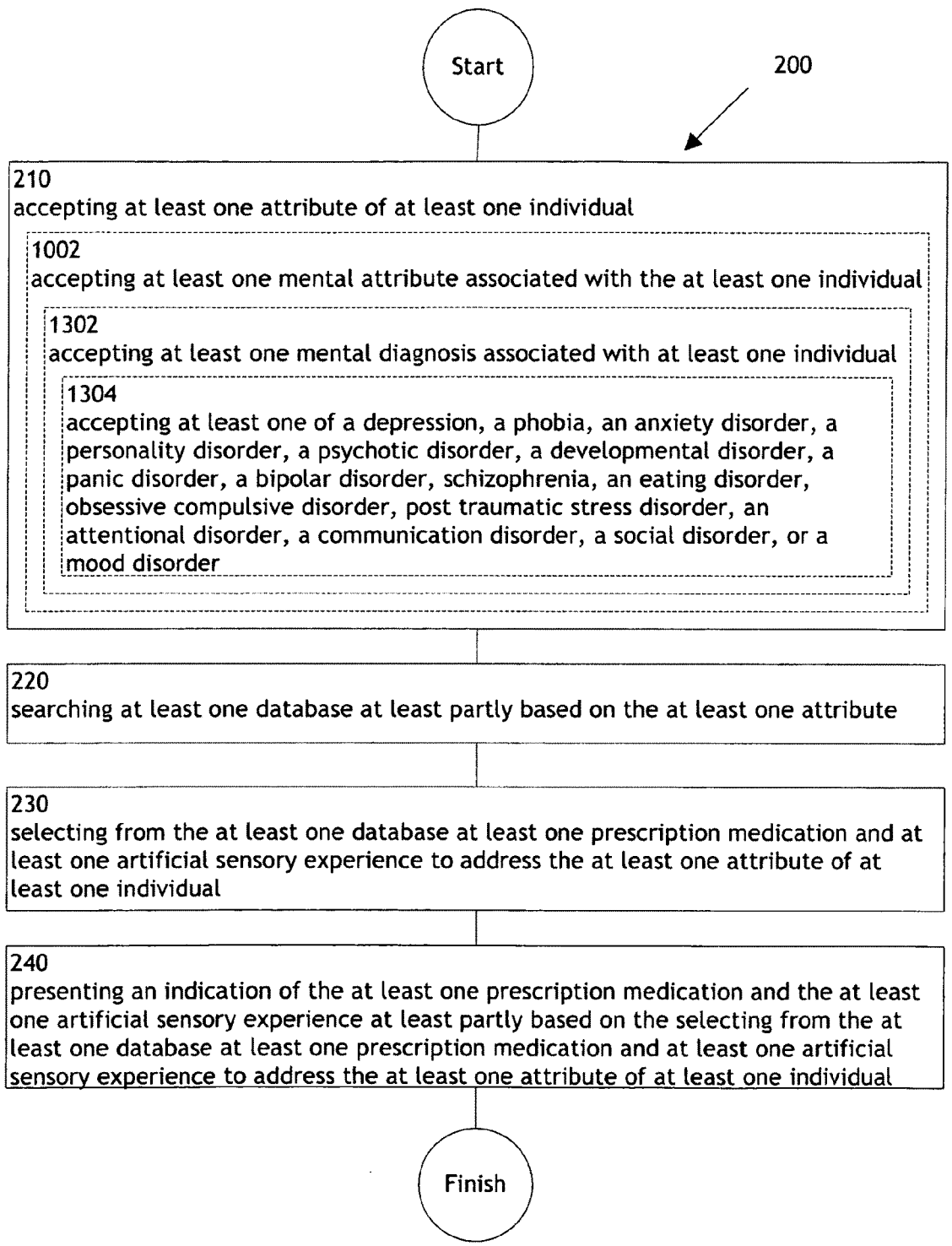
FIG. 13 illustrates an alternative embodiment of the operational flow of FIG. 2.

FIG. 13 illustrates alternative embodiments of the example operational flow 200 of FIG. 2. FIG. 13 illustrates example embodiments where operation 210 may include at least one additional operation. Additional operations may include an operation 1302, and/or an operation 1304. Further, operation 1302 illustrates accepting at least one mental diagnosis associated with at least one individual. For example, as shown in FIG. 1, acceptor module 102 may accept at least one mental diagnosis associated with at least one individual. In a specific instance, acceptor module 102 accepts from memory device 112 a mental diagnosis including a phobia associated with an anonymous individual or an individual named Roy Black. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, acceptor module 102 may include a computer processor.

Operation 1304 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIG. 1, acceptor module 102 may accept at least one of a depression, a phobia, an anxiety disorder, a personality disorder, a psychotic disorder, a developmental disorder, a panic disorder, or a mood disorder. In one example, acceptor module 102 accepts from database entry 114 a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or butimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, acceptor module 102 may include a computer processor.

Figure 14:
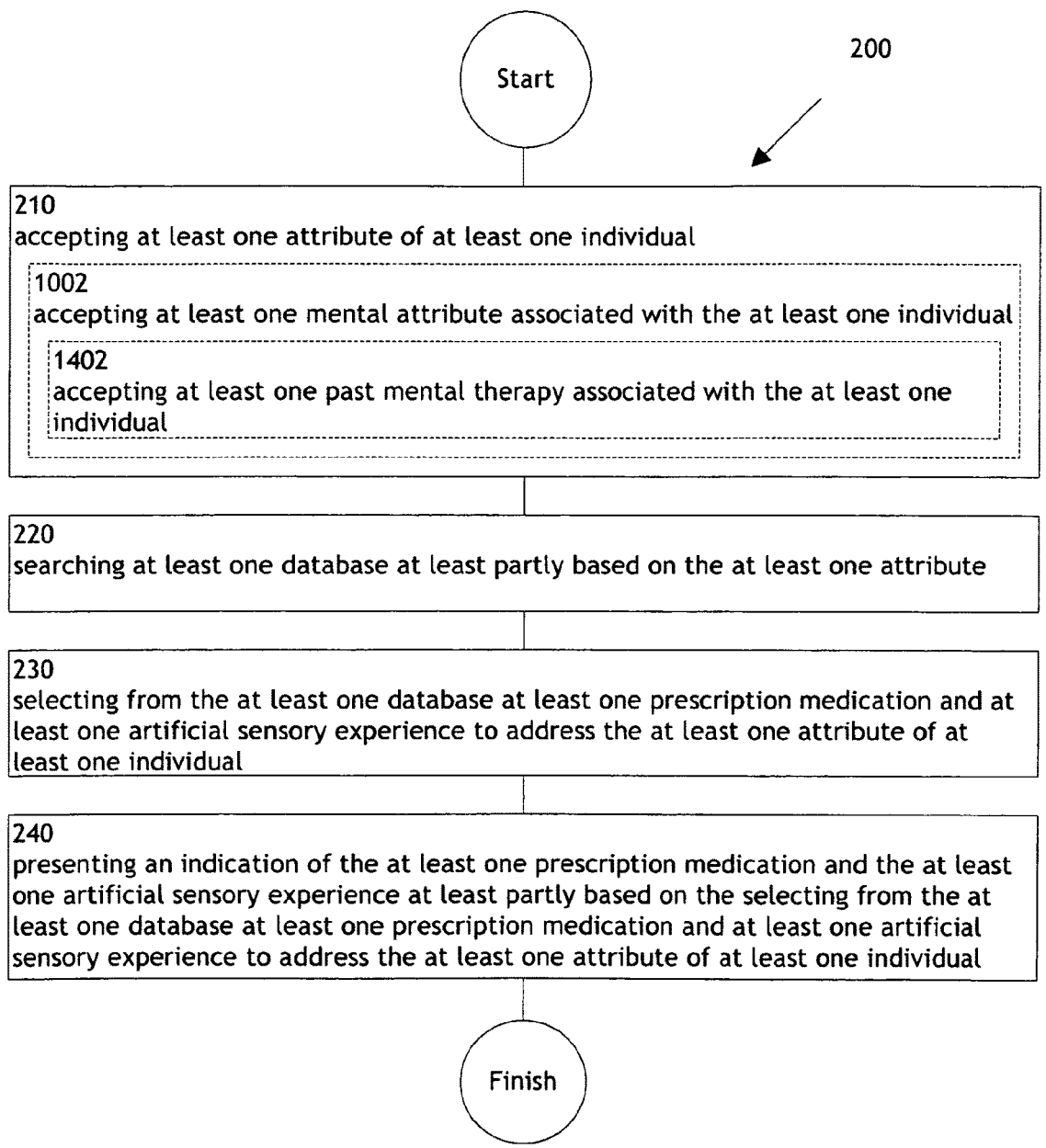
FIG. 14 illustrates an alternative embodiment of the operational flow of FIG. 2.

FIG. 14 illustrates alternative embodiments of the example operational flow 200 of FIG. 2. FIG. 14 illustrates example embodiments where operation 210 may include at least one additional operation. Additional operations may include an operation 1402. Further, operation 1402 illustrates accepting at least one past mental therapy associated with the at least one individual. For example, as shown in FIG. 1, acceptor module 102 may accept at least one past mental therapy associated with the at least one individual. In one instance, acceptor module 102 can accept from database entry 114 a past mental therapy associated with an individual named James Williams or an anonymous individual. A past mental therapy may include a list and/or a record of at least one mental therapy, such as an anti-depressant medication, administered to at least one individual. In some instances, acceptor module 102 may include a computer processor.

Figure 15:
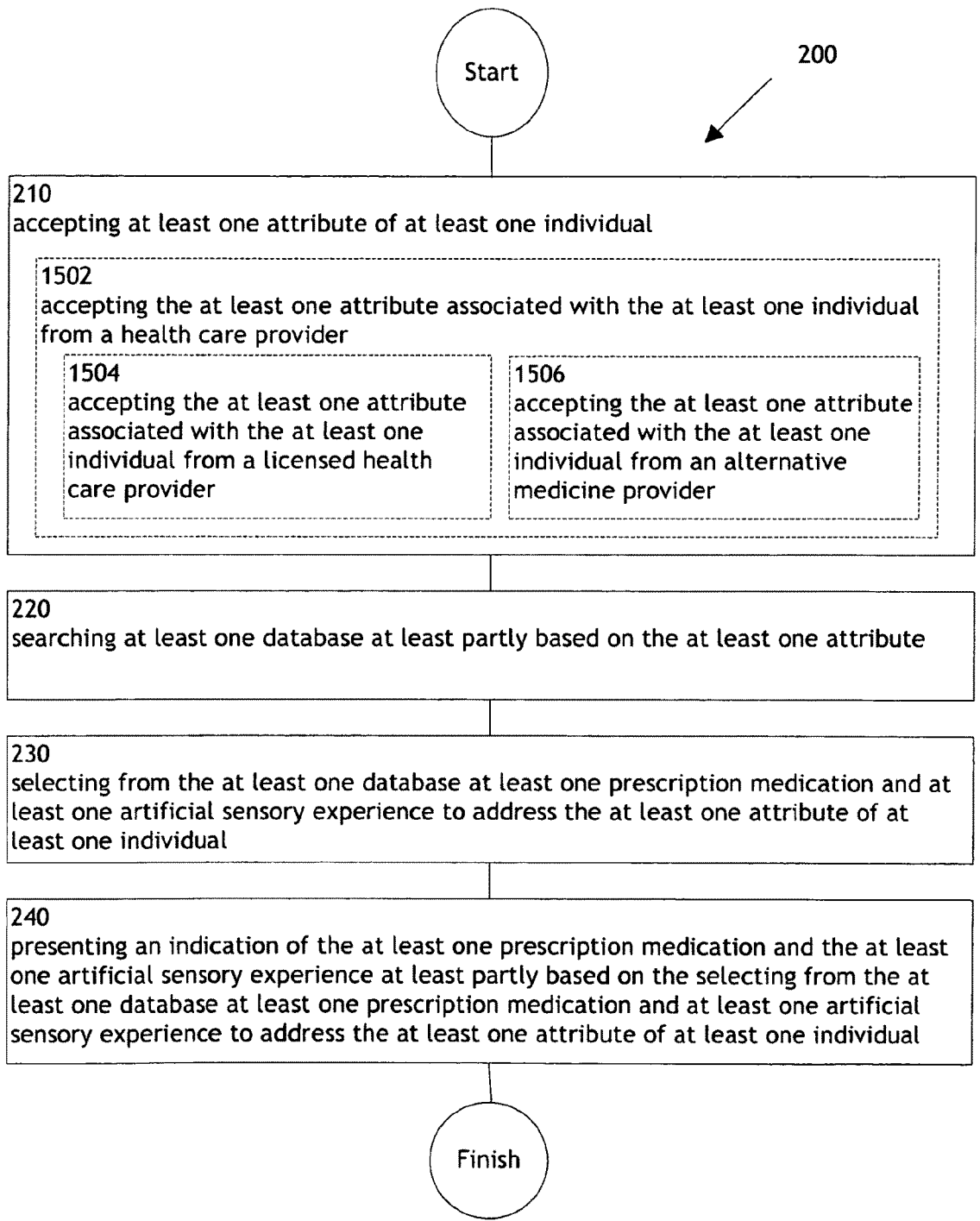
FIG. 15 illustrates an alternative embodiment of the operational flow of FIG. 2.

FIG. 15 illustrates alternative embodiments of the example operational flow 200 of FIG. 2. FIG. 15 illustrates example embodiments where operation 210 may include at least one additional operation. Additional operations may include an operation 1502, an operation 1504, and/or an operation 1506.

Operation 1502 illustrates accepting the at least one attribute associated with the at least one individual from a health care provider. For example, as shown in FIG. 1, acceptor module 102 may accept the at least one attribute associated with the at least one individual from a health care provider. In one example, acceptor module 102 can accept from user interface 116 and/or user 118 an attribute 120 including a medication history associated with a group of fifty individuals from a health care provider 136. A health care provider may include a hospital, a doctor, a nurse, a medical clinic, a dentist, and/or any provider of preventive, diagnostic, therapeutic, rehabilitative, maintenance, or palliative care and/or counseling. A healthcare provider may include a seller and/or dispenser of prescription drugs or medical devices. In some instances, acceptor module 102 may include a computer processor.

Operation 1504 illustrates accepting the at least one attribute associated with the at least one individual from a licensed health care provider. For example, as shown in FIG. 1, acceptor module 102 may accept the at least one attribute associated with the at least one individual from a licensed health care provider. In one instance, acceptor module 102 accepts from memory device 112 an attribute 120 including a symptom indication a phobia associated with an individual named Robert Clark from a licensed health care provider 136. A licensed health care provider may include a person licensed by a governing authority, such as a state, to provide medical and/or health care. Some examples of a licensed health care provider may include a licensed medical doctor or physician, a licensed physician's assistant, a physical therapist, an occupational therapist, and/or a licensed nurse practitioner. In some instances, acceptor module 102 may include a computer processor.

Operation 1506 illustrates accepting the at least one attribute associated with the at least one individual from an alternative medicine provider. For example, as shown in FIG. 1, acceptor module 102 may accept the at least one attribute associated with the at least one individual from an alternative medicine provider. In one instance, acceptor module 102 can accept from network storage 110 an attribute 120 associated with an individual named Connie Martin from an alternative medicine provider. An alternative medicine provider may include a provider of folk medicine, herbal medicine, diet fads, homeopathy, faith healing, new age healing, chiropractic, acupuncture, aromatherapy, naturopathy, massage, reflexology, hypnotism, and/or music therapy. In some instances, acceptor module 102 may include a computer processor.

Figure 16:
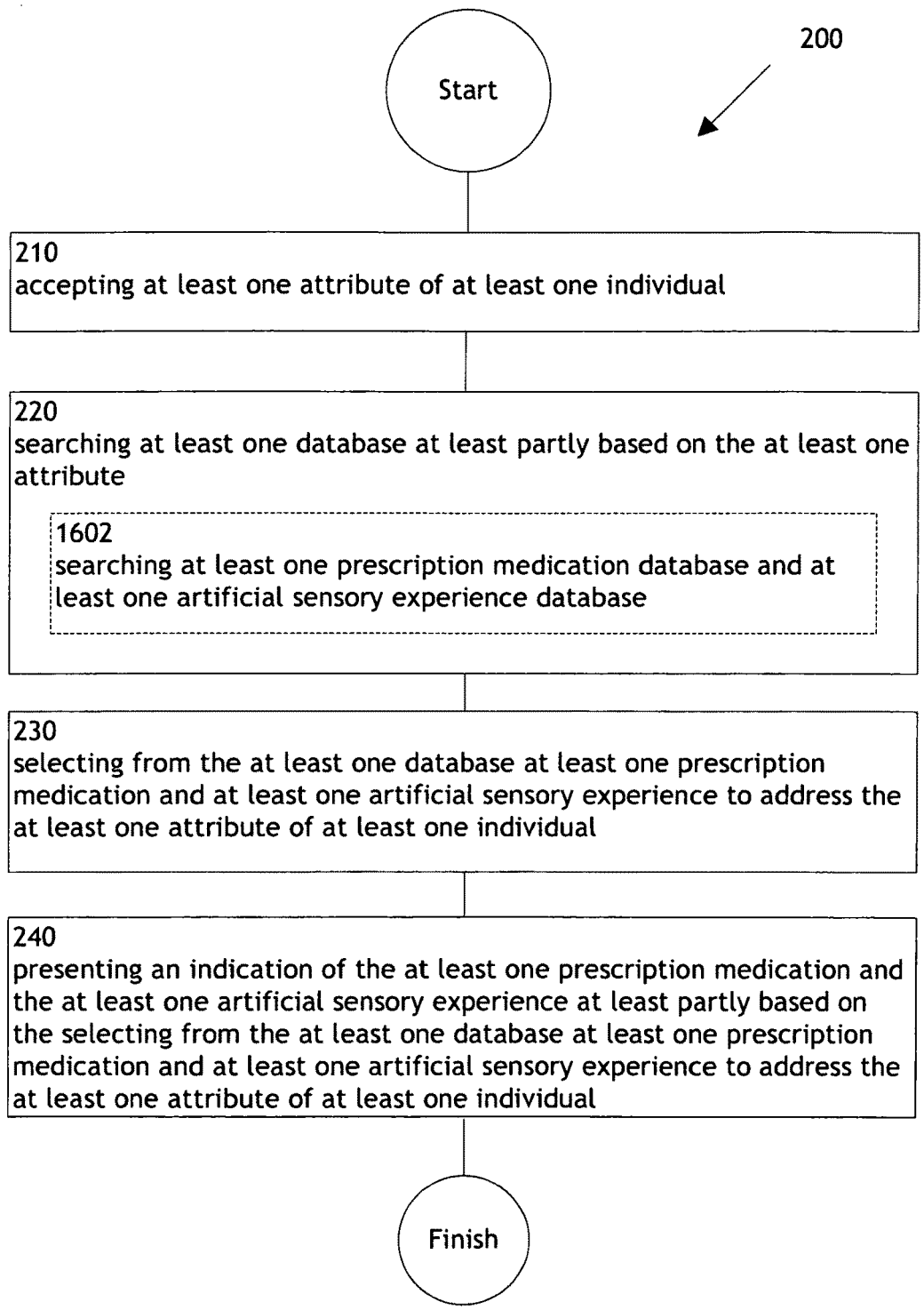
FIG. 16 illustrates an alternative embodiment of the operational flow of FIG. 2.

FIG. 16 illustrates alternative embodiments of the example operational flow 200 of FIG. 2. FIG. 16 illustrates example embodiments where operation 220 may include at least one additional operation. Additional operations may include an operation 1602.

Operation 1602 illustrates searching at least one prescription medication database and at least one artificial sensory experience database. For example, as shown in FIG. 1, querier module 104 may search at least one prescription medication database and at least one artificial sensory experience database. In one example, querier module 104 searches a medication database 124 and an artificial sensory experience database 126. A database may include a collection of data organized for convenient access. The database may include information digitally stored in a memory device 112, as at least a portion of at least one database entry 114, and/or in network storage 110. In some instances, the database may include information stored non-digitally such as at least a portion of a book, a paper file, and/or a non-computerized index and/or catalog. Non-computerized information may be received by acceptor module 102 by scanning or by manually entering the information into a digital format. A prescription database and/or medication database may include any database associated with at least one prescription medication and may be available to health care professionals and/or the public. An artificial sensory experience database may include any database associated with at least one artificial sensory experience and may include a database accessible by the public and/or a health care provider. In some instances, acceptor module 102 and/or querier module 104 may include one or more computer processors.

Figure 17:
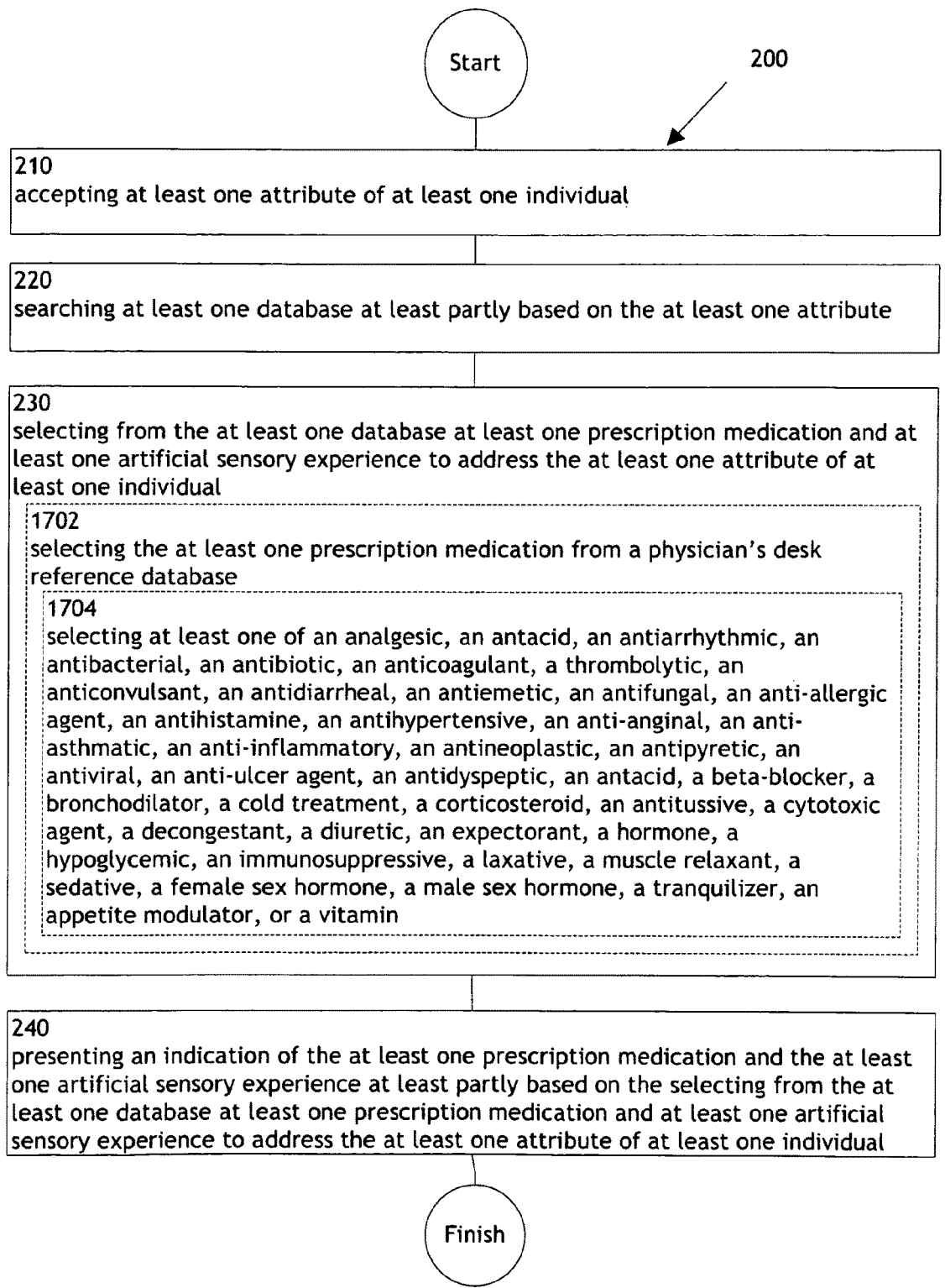
FIG. 17 illustrates an alternative embodiment of the operational flow of FIG. 2.

FIG. 17 illustrates alternative embodiments of the example operational flow 200 of FIG. 2. FIG. 17 illustrates example embodiments where operation 230 may include at least one additional operation. Additional operations may include an operation 1702, and/or an operation 1704.

Operation 1702 illustrates selecting the at least one prescription medication from a physician's desk reference database. For example, as shown in FIG. 1, selector module 106 may select the at least one prescription medication from a physician's desk reference database. In one example, selector module 106 selects the at least one prescription medication from a physician's desk reference database 122, such as a PDR psychiatry database. In some instances, selector module 106 may include a computer processor.

Operation 1704 illustrates selecting at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, an antitussive, a cytotoxic agent, a decongestant, a diuretic, an expectorant, a hormone, a hypoglycemic, an immunosuppressive, a laxative, a muscle relaxant, a sedative, a female sex hormone, a mate sex hormone, a tranquilizer, an appetite modulator, or a vitamin. For example, as shown in FIG. 1, selector module 106 may select at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, a cough suppressant, an antitussive, a cytotoxic agent, a decongestant, a diuretic, an expectorant, a hormone, a hypoglycemic, an immunosuppressive, a laxative, a muscle relaxant, a sedative, a female sex hormone, a male sex hormone, a tranquilizer, an appetite modulator, or a vitamin. An analgesic may include a drug and/or other medication suitable for relieving pain. Additionally, an analgesic may be effective for relieving different degrees of pain. Some examples of an analgesic may include narcotics such as morphine or oxycodone, non-narcotics, an NSAID such as aspirin or naproxen or ibuprofen, and/or acetaminophen. An antacid may include a substance for neutralizing stomach acid, such as a proton pump inhibitor. Some examples of an antacid may include imeprazole and/or a pharmaceutical composition containing aluminum hydroxide, magnesium hydroxide, aluminum carbonate, calcium carbonate, sodium bicarbonate, hydrotalcite, bismuth subsalicylate, magaldrate, and/or simethicone.

An antiarrhythmic may include a drug for controlling a heartbeat irregularity. Some examples of an antiarrhythmic may include a beta blocker such as propanolol, and/or lidocaine, verapamil, and/or quinidine. An antibacterial may include a drug used to treat an infection. Some examples of an antibacterial may include amoxicillin and/or ciprofloxacin. An antibiotic may include a drug made from naturally occurring and/or synthetic substances for combating a bacterial infection. Some examples of an antibiotic may include penicillin, streptomycin, and/or sulfonamide-based drugs. An anticoagulant may include an agent for preventing blood clots. An example of an anticoagulant may include a vitamin K antagonist, such as warfarin, and/or aspirin. A thrombolytic may help dissolve and disperse a blood clot and may be prescribed for patients with recent arterial or venous thrombosis. A thrombolytic may be derived from *Streptomyces* spp. and/or recombinant DNA technology and may include streptokinase, urokinase, and/or a tissue plasminogen activator (TPA) such as alteplase.

An anticonvulsant may include a pharmaceutical administered for the prevention of seizures. Some examples of an anticonvulsant may include a barbiturate, a carbamate, a fatty acid derivative, and/or a sulfonamide. An antidiarrheal may include a drug utilized for the relief of diarrhea. Some examples of an antidiarrheal may include an antispasmodic such as diphenoxylate and loperamide, a bismuth compound, a bulking agent, and/or an absorbent. An antiemetic may include a drug used to treat nausea and vomiting. Some examples of an antiemetic may include a 5-HT3 receptor antagonist, a dopamine antagonist, and/or a histamine. An antifungal may include a drug used to treat fungal infections, the most common of which affect the hair, skin, nails, and/or mucous membranes. Some examples of antifungals may include polyene antifungals, imidazole and triazole antifungals, and/or allylamines. An anti-allergenic agent may include an agent characterized by preventing and/or reducing the effect of an allergen. Some examples of an anti-allergenic may include an antihistamine, cortisone, hydrocortisone, and/or epinephrine. An antihistamine may include an agent used for counteracting the effects of histamine. Some examples of an antihistamine may include a H1-receptor antagonist and/or a H2-receptor antagonist. An antihypertensive may include drugs utilized for lowering blood pressure. Some examples of an antihypertensive may include a diuretic, an adrenergic receptor antagonist, and/or an ACE inhibitor. An anti-anginal may include an agent used for preventing and/or reducing angina and/or chest pain. Some examples of an anti-anginal may include aspirin, ranolazine, and/or ivabradine. An anti-asthmatic may include an agent for preventing and/or reducing asthma and/or its effects. Some examples of an anti-asthmatic may include albuterol, an inhaled steroid, for example budesonide or fluticasone, and/or ipratropium bromide.

An anti-inflammatory may include an agent utilized to reduce inflammation and/or to treat redness, heat, swelling, and/or increased blood flow associated for example, that seen with an infection or injury, or in many chronic diseases such as rheumatoid arthritis and gout. Some anti-inflammatories may include steroids, and/or NSAIDs such as naproxen, ibuprofen, and/or aspirin. An antineoplastic may include drugs used to treat cancer and to inhibit and/or prevent the development of tumors. Some antineoplastics may include alkylating agents, antimetabolites, enzymes, enzyme inhibitors, immune modulators, and taxoids. An antipyretic may include a drug used to reduce a fever. Some examples of an antipyretic may include aspirin and/or acetaminophen. An antiviral may include a drug used to treat viral infections and/or to provide temporary protection against viral infections such as influenza. Some examples of an antiviral may include an interferon, acyclovir, ribavirin, and/or oseltamivir. An anti-ulcer agent may include an agent used for preventing and/or lessening the effect of an ulcer, including stomach ulcers, mouth ulcers, or other types of ulcers. Some examples of an anti-ulcer agent may include a bismuth compound, a prostaglandin analogue, and/or cimetidine. An antidyspeptic may include an agent used for treating and/or preventing dyspepsia. Some examples of an antidyspeptic may include simethicone and/or a proton pump inhibitor, such as esomeprazole. An antacid may include a substance, often a base, which may counteract stomach acidity. Some examples of an antacid may include magnesium hydroxide, aluminum hydroxide, calcium carbonate, and/or bismuth subsalicylate. A beta-blocker may include a beta-adrenergic blocking agent utilized for reducing the oxygen needs of the heart by reducing the heartbeat rate. Some examples of a beta-blocker may include propranolol, esmolol, bisoprolol, and/or timolol. A bronchodilator may include an agent utilized for opening the bronchial tubes within the lungs when the tubes have become narrowed, for example, by muscle spasm and may be used for treating asthma. Some examples of a bronchodilator may include albuterol and/or ipratropium bromide. A cold treatment may include an agent utilized for treating aches, pains, and/or fever accompanying a cold. Some cold treatments may include aspirin, acetaminophen, a decongestant, an antihistamine, and/or caffeine.

A corticosteroid may include a hormonal preparation used as an anti-inflammatory for arthritis or asthma and/or treating some malignancies or compensating for a deficiency of natural hormones. Some examples of a corticosteroid may include cortisol and/or aldosterone. A cough suppressant may include an agent used to soothe irritation caused by coughing and/or to prevent coughing. Some examples of a cough suppressant may include codeine, an antihistamine, and/or dextromethorphan. An antitussive may include a cough suppressant. A cytotoxic agent may include a drug used for killing and/or damaging cells. Some examples of a cytotoxic agent may include actinomycin-D, azathioprine, bleomycin, melphalan, busulphan, doxorubicin, etoposide, an antineoplastic agent, and/or an apoptotic agent. A decongestant may include an agent for reducing the swelling of the mucous membranes lining the nose and/or throat. Some examples of a decongestant may include pseudoephedrine and phenylephrine. A diuretic may include an agent for increasing the quantity of urine produced by the kidneys and passed out of the body. Some examples of a diuretic may include hydrochlorothiazide, spironolactone, mannitol, and/or glucose. An expectorant may include an agent for stimulating the flow of saliva, loosening and thinning mucus in airways, and/or promoting a more productive cough as to eliminate phlegm from the respiratory tract. An example of an expectorant may include guaifenesin. A hormone may include molecules produced naturally by the endocrine glands. Some examples of a hormone may include steroid hormones, amine-derived hormones, peptide hormones, and/or lipid and phospholipid-derived hormones. A hypoglycemic may include an agent for lowering the level of glucose in the blood. Some examples of a hypoglycemic may include a sulfonylurea, a meglitinide, a biguanide, a thiazolidinedione, and/or a alpha-glucosidase inhibitor. An immunosuppressive may include an agent for preventing or reducing the body's normal reaction to invasion by disease and/or foreign tissues. Some examples of an immunosuppressive may include a drug such as a corticosteroid, cyclosporine, rapamycin, which acts on immunophilins, and/or an antibody.

A laxative may include an agent for increasing the frequency and ease of bowel movements. Some examples of a laxative may include methylcellulose, docusate, mineral oil, and/or magnesium hydroxide. A muscle relaxant may include an agent utilized for relieving muscle spasms. Some examples of a muscle relaxant may include neuromuscular blocking drugs, carisoprodol, cyclobenzaprine, metaxalone, a benzodiazepine and/or a tranquilizer. A sedative may include a substance which depresses the central nervous system and may result in calmness, relaxation, reduction of anxiety, sleepiness, and/or slowed breathing. Some examples of a sedative may include zolpidem, and/or eszopiclone. A female sex hormone may include a hormone responsible for the development of female secondary sexual characteristics. Some examples of a female sex hormone may include estrogen and progesterone. A male sex hormone may include a hormone responsible for the development of secondary male sexual characteristics. One example of a male sex hormone may include testosterone. Sex hormone-related agents may include agents metabolically related to sex hormones. Examples of sex hormone-related agents may include sterols, androgens (testosterone), progestogens estrogens (estradiols, estrone), follicle-stimulating hormone, luteinizing hormone, inhibin B, anti-Mullerian hormone thyroid-related hormones. A tranquilizer may include any drug having a calming and/or sedative effect. Some examples of a tranquilizer may include an antidepressant, a barbiturate, and/or a benzodiazepine. An appetite modulator may include an agent used for regulating and/or adjusting appetite. Some examples of an appetite modulator may include recombinant PYY 3-36 and/or sibutramine. A vitamin may include chemicals essential in relatively small quantities for good health. Some examples of a vitamin may include Vitamin A, Vitamin C, Vitamin D, and/or Vitamin K.

In one instance, selector module 106 can select an analgesic and an antipsychotic for subsequent presentation, perhaps in response to accepting a pain symptom and a hallucination symptom as the at least one attribute. In some instances, selector module 106 may include a computer processor.

Figure 18:
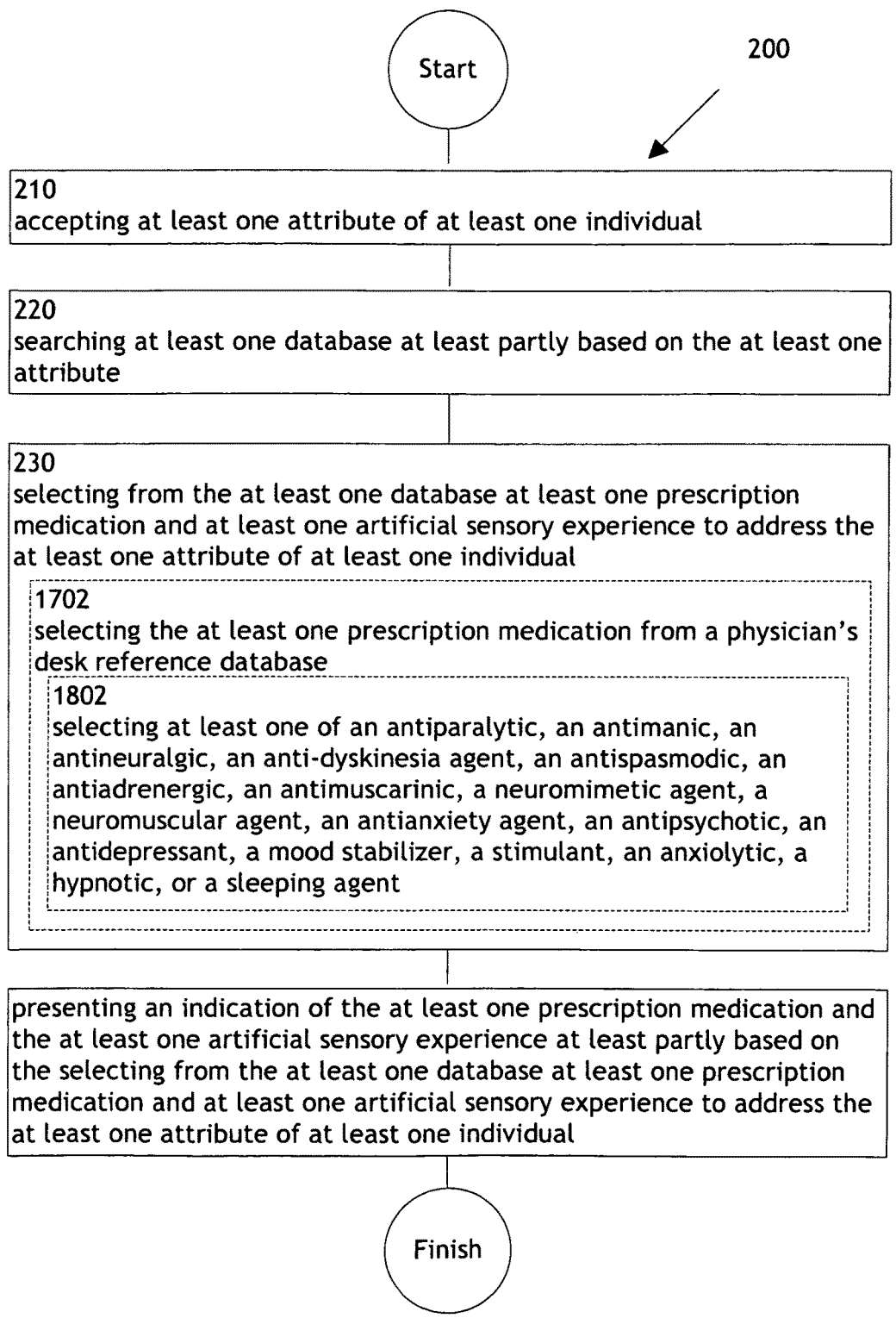
FIG. 18 illustrates an alternative embodiment of the operational flow of FIG. 2.

FIG. 18 illustrates alternative embodiments of the example operational flow 200 of FIG. 2. FIG. 18 illustrates example embodiments where operation 230 may include at least one additional operation. Additional operations may include an operation 1802. Further, operation 1802 illustrates selecting at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety agent, an antipsychotic, an antidepressant, a mood stabilizer, a stimulant, an anxiolytic, a hypnotic, or a sleeping agent. For example, as shown in FIG. 1, selector module 106 may select at least one of an antiparalytic, an antimanic, an antineuralgic, an anti-dyskinesia agent, an antispasmodic, an antiadrenergic, an antimuscarinic, a neuromimetic agent, a neuromuscular agent, an anti-anxiety drug, an antipsychotic, an antidepressant, a mood stabilizer, a stimulant, an anxiolytic, a hypnotic, and/or a sleeping agent such as a long-acting barbiturate. In one example, selector module 106 selects an antianxiety drug and a sleeping agent. An antiparalytic may include an agent used for preventing the loss of and/or recovering muscle function. One example of an antiparalytic may include methylprednisolone. An antimanic may include an agent used for treating and/or suppressing mania. Some examples may include lamotrigine and/or carbamazepine. An antineuralgic may include an agent for relieving paroxysmal nerve pain. One example of an antineuralgic may include carbamazepine. An anti-dyskinesia agent may include an agent used for reducing and/or preventing dyskinesia, including involuntary muscle movement. One example of an anti-dyskinesia agent may include methylenedioxymethamphetamine. An antispasmodic may include a drug or an herb that suppresses smooth muscle contraction. Some examples of an antispasmodic may include dicyclomine and/or hyoscyamine. An antiadrenergic may include a medication for inhibiting the functioning of the sympathetic nervous system. Some examples of an antiadrenergic may include clonidine and/or mecamylamine. An antimuscarinic may include an agent for reducing the activity of the muscarinic acetylcholine receptor. Some examples of an antimuscarinic may include atropine and/or hyoscine. A neuromimetic agent may include an agent that mimics the response of an effector organ to nerve impulses. A neuromuscular agent may block neuromuscular transmission at the neuromuscular junction and cause paralysis of the affected skeletal muscles. Some examples of a neuromuscular agent may include atracurium and/or vecuronium. An antianxiety drug may include a drug for suppressing anxiety and relaxing the muscles. An antianxiety drug may include a sedative, a tranquilizer, an anxiolytic, such as a benzodiazepine, alprazolam and/or diazepam, an antidepressant, a short-acting barbiturate, and/or an herbal treatment, such as chamomile, kava extract, Kratom, and/or valerian. An antipsychotic may include a group of drugs commonly used to treat psychosis and may include phenothiazines, thioxanthenes, butyrophenones, risperidone, amisulpride, and/or other suitable drugs. An antidepressant may include a psychiatric medication or other substance, such as a nutrient or herb, used for alleviating depression or dysthymia. Some examples of an antidepressant may include a selective serotonin reuptake inhibitor, such as Prozac and/or Zoloft, and/or a serotonin-norepinephrine reuptake inhibitor, such as Cymbalta. A mood stabilizer may include a psychiatric medication used to treat mood disorders characterized by intense and sustained mood shifts. Some examples of a mood stabilizer may include lithium carbonate and/or lamotrigine. A stimulant may include substances that may temporarily increase alertness and awareness, such as caffeine, ephedrine, and/or nicotine. An anxiolytic may include a substance used for the treatment of anxiety, such as a benzodiazepine and/or a barbiturate. A hypnotic may include substances that induce sleep, such as a barbiturate and/or an antihistamine (diphenhydramine). A sleeping agent may include any number of medications for helping a person sleep and/or stay asleep and may include benzodiazepines, antidepressants, metatonin, and/or antihistamines as well as other suitable substances. In some instances, selector module 106 may include a computer processor.

Figure 19:
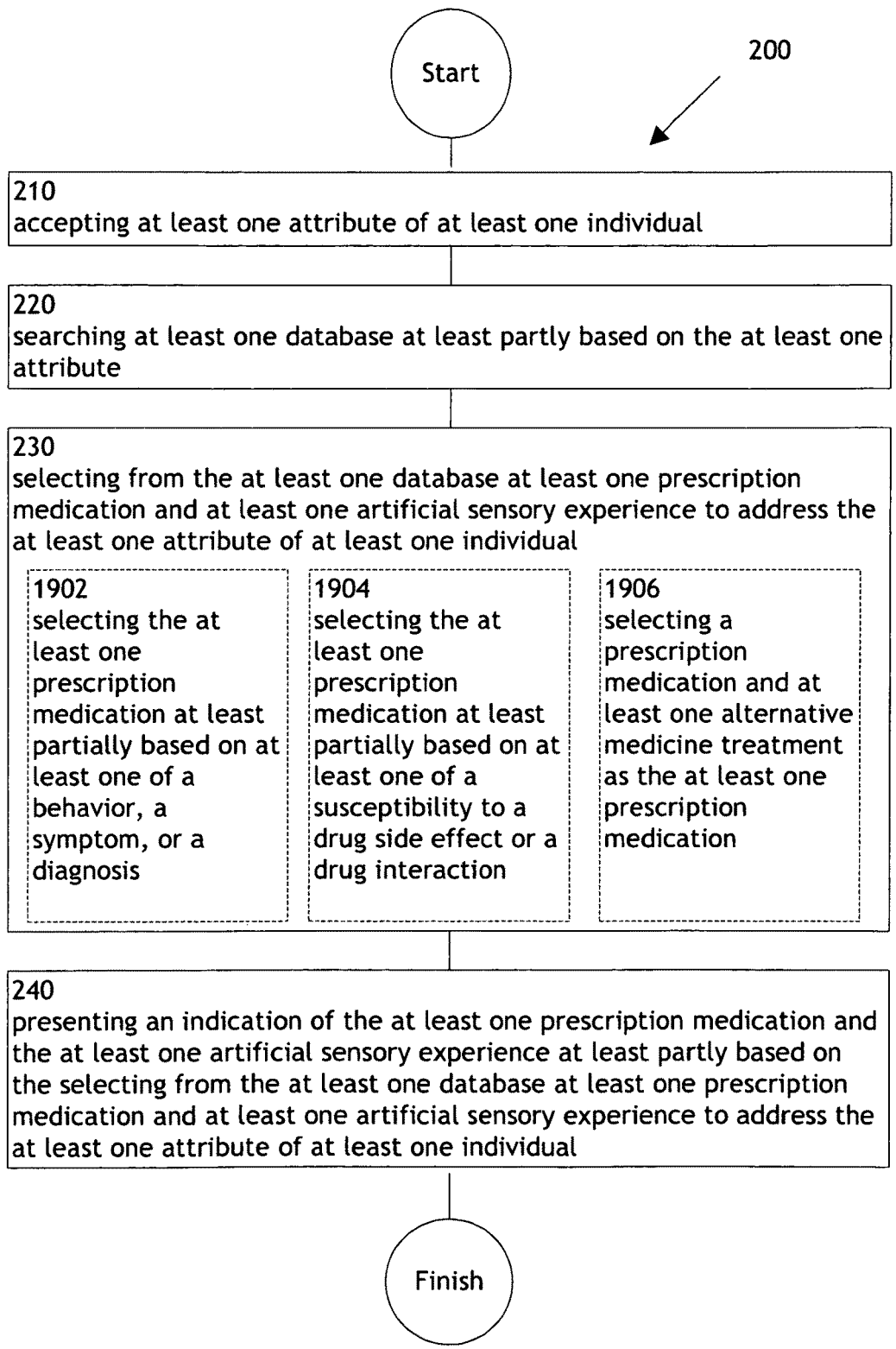
FIG. 19 illustrates an alternative embodiment of the operational flow of FIG. 2.

FIG. 19 illustrates alternative embodiments of the example operational flow 200 of FIG. 2. FIG. 19 illustrates example embodiments where operation 230 may include at least one additional operation. Additional operations may include an operation 1902, an operation 1904, and/or an operation 1906.

Operation 1902 illustrates selecting the at least one prescription medication at least partially based on at least one of a behavior, a symptom, or a diagnosis. For example, as shown in FIG. 1, selector module 106 may select the at least one prescription medication at least partially based on at least one of a behavior, a symptom, or a diagnosis. In one instance, selector module 106 can select a prescription medication based on a diagnosis. A behavior may include the manner a person behaves toward other people and/or a certain circumstance. A symptom may include a subjective indicator of a health problem reported by an individual, or a sign of a health problem noticed by another, perhaps a doctor. A symptom may be evidence of a disease, a disability, an impairment, and/or a condition. A diagnosis may include an identification of a disease, a disability, an impairment, and/or a condition. In some instances, selector module 106 may include a computer processor.

Operation 1904 illustrates selecting the at least one prescription medication at least partially based on at least one of a susceptibility to a drug side effect or a drug interaction. For example, as shown in FIG. 1, selector module 106 may select the at least one prescription medication at least partially based on at least one of a susceptibility to a drug side effect or a drug interaction. In one instance, selector module 106 can select a prescription medication based on a susceptibility to a drug side effect including an allergy. A susceptibility to a drug side effect may include a probability a certain person may be vulnerable to a side effect associated with a specific drug and/or medication. A susceptibility to a drug side effect may include predisposition to a particular drug side effect or class of drug side effects, such as upset stomach associated with aspirin formulations. A drug reaction may include a possible response a person may exhibit resulting from at least one drug and/or medication administered to the person. A drug reaction may include an allergy and/or a drug and/or medication interaction with a separate drug and/or medication. In some instances, selector module 106 may include a computer processor.

Operation 1906 illustrates selecting a prescription medication and at least one alternative medicine treatment as the at least one prescription medication. For example, as shown in FIG. 1, selector module 106 may select a prescription medication and at least one alternative medicine treatment as the at least one prescription medication. In one instance, selector module 106 can select a prescription medication and at least one alternative medicine treatment as the at least one prescription medication. A prescription medication may include a medication, drug, and/or treatment available only with written instructions from a doctor, dentist, and/or other licensed professional. An alternative medicine treatment may include medical and/or nutraceutical treatments and/or practices utilized instead of standard medical treatments. Some examples of alternative medicine treatments may include chiropractic, herbal medicine, acupuncture, homeopathy, naturopathy, and/or spiritual devotions. In some instances, selector module 106 may include a computer processor.

Figure 20:
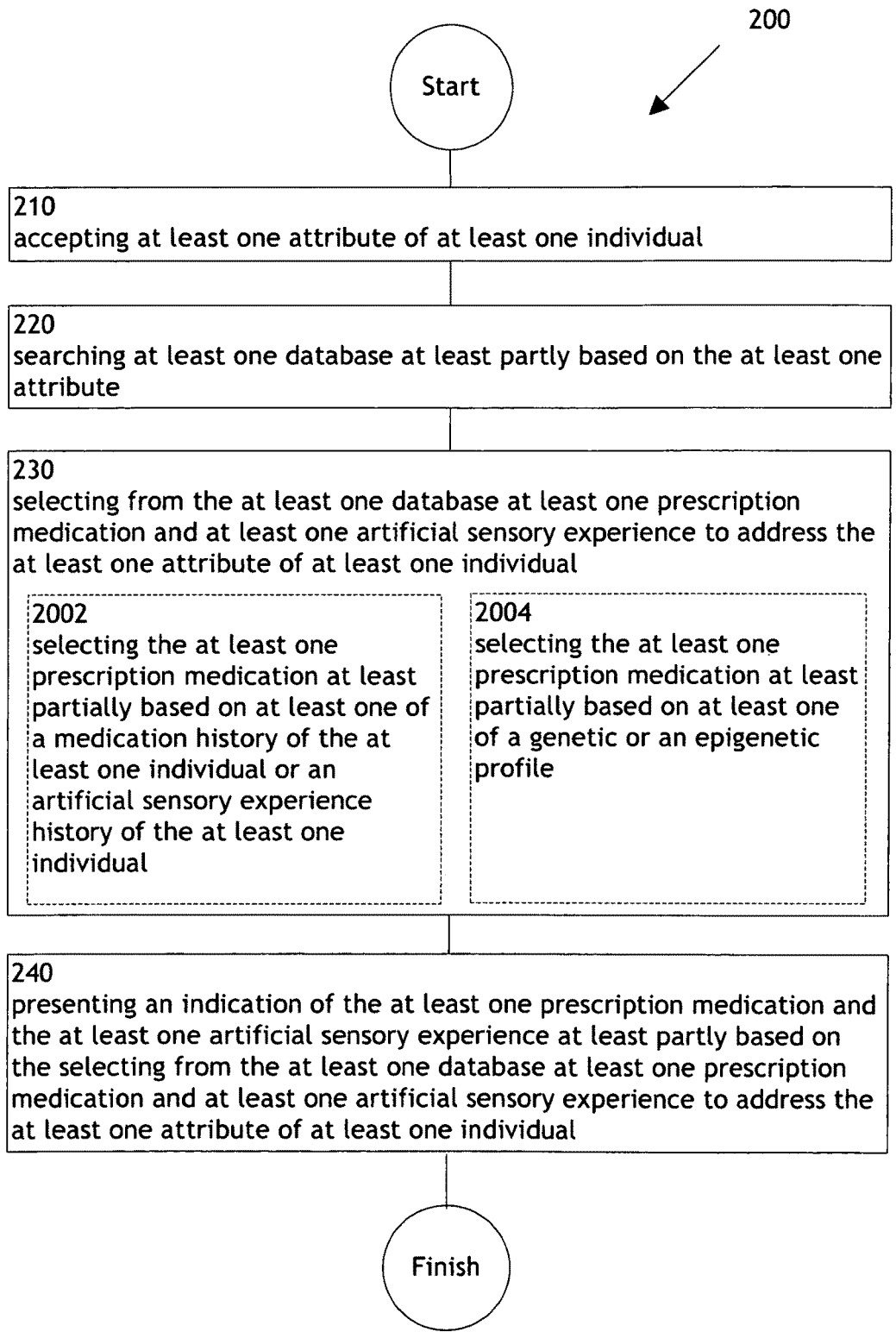
FIG. 20 illustrates an alternative embodiment of the operational flow of FIG. 2.

FIG. 20 illustrates alternative embodiments of the example operational flow 200 of FIG. 2. FIG. 20 illustrates example embodiments where operation 230 may include at least one additional operation. Additional operations may include an operation 2002, and/or an operation 2004.

Operation 2002 illustrates selecting the at least one prescription medication at least partially based on at least one of a medication history of the at least one individual or an artificial sensory experience history of the at least one individual. For example, as shown in FIG. 1, selector module 106 may select the at least one prescription medication at least partially based on at least one of a medication history of the at least one individual or an artificial sensory experience history of the at least one individual. In one example, selector module 106 can select a prescription medication based on a medication history of an individual named Jennifer Harris or an anonymous individual. A medication history may include any record of administered medications and/or drugs that may exist for an individual. An artificial sensory experience history may include any record of an artificial sensory experience associated with an individual. In some instances, selector module 106 may include a computer processor.

Operation 2004 illustrates selecting the at least one prescription medication at least partially based on at least one of a genetic or an epigenetic profile. For example, as shown in FIG. 1, selector module 106 may select the at least one prescription medication at least partially based on at least one of a genetic or an epigenetic profile. In one instance, selector module 106 can select a prescription medication based on a genetic profile. A genetic profile may include hereditary information encoded in the genetic sequence of an individual. An epigenetic profile may include information regarding chromatin and/or DNA modifications that are stable over rounds of cell division but do not involve changes in the underlying DNA sequence of the organism, such as histone acetylation and/or DNA methylation. Other epigenetic information may be found in higher-order chromatin structure. In some instances, selector module 106 may include a computer processor.

Figure 21:
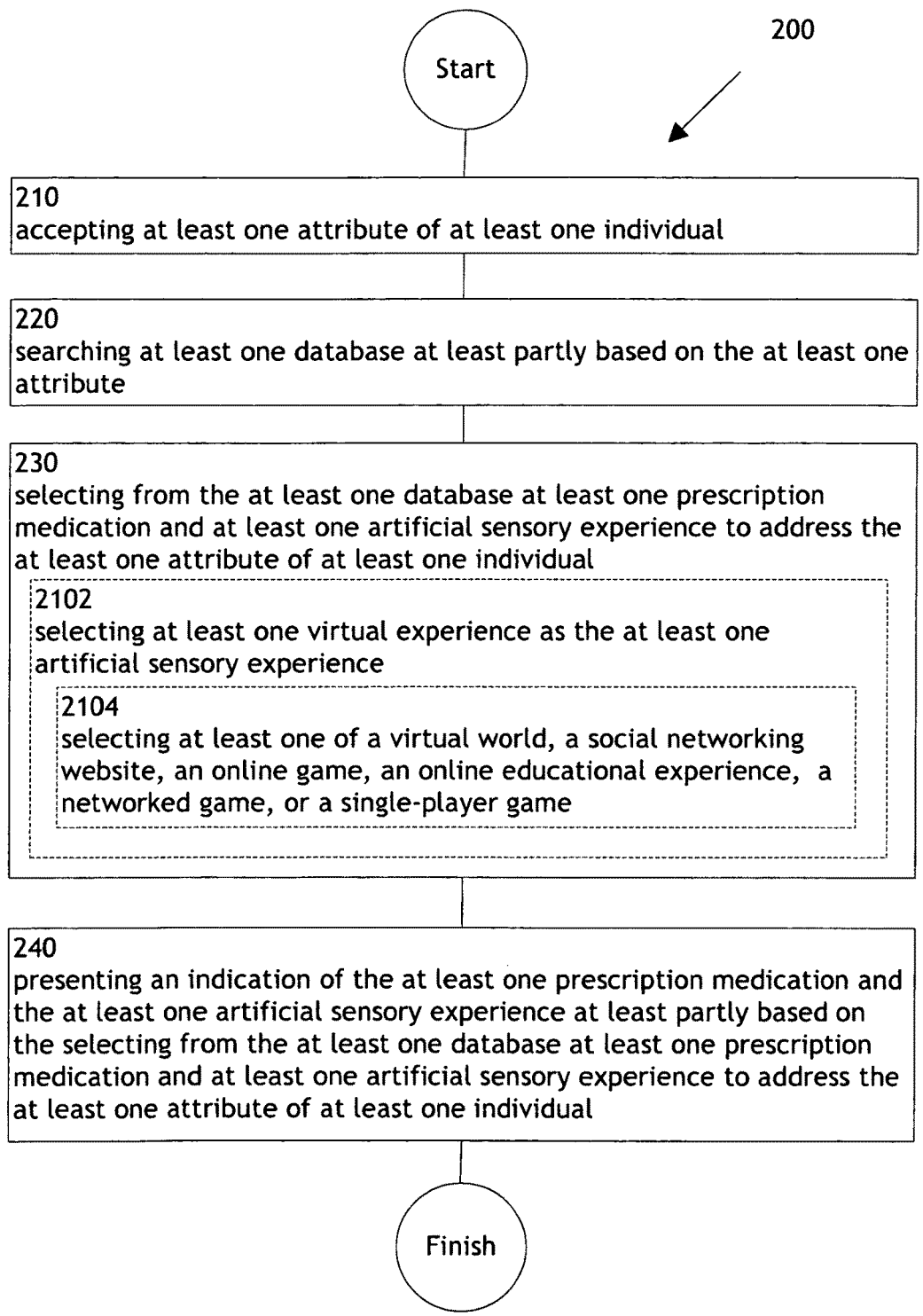
FIG. 21 illustrates an alternative embodiment of the operational flow of FIG. 2.

FIG. 21 illustrates alternative embodiments of the example operational flow 200 of FIG. 2. FIG. 21 illustrates example embodiments where operation 230 may include at least one additional operation. Additional operations may include an operation 2102, and/or an operation 2104.

Operation 2102 illustrates selecting at least one virtual experience as the at least one artificial sensory experience. For example, as shown in FIG. 1, selector module 106 may select at least one virtual experience as the at least one artificial sensory experience. In one example, selector module 106 can select a virtual experience as the artificial sensory experience. A virtual experience may include an experience with a computer-simulated environment. Such a virtual experience may be interactive or non-interactive. Some examples of a virtual experience may include an experience with a virtual world, a simulated reality, a computer game, and/or a virtual tour, and may involve input devices such as a keyboard, a mouse, an accelerometer-containing input device, and/or a wired glove. A virtual experience may also involve a visual and/or auditory monitoring device such as a video monitor, goggles, loudspeakers, or the like. Examples of a virtual experience include second life, snow world, or the like. In some instances, selector module 106 may include a computer processor.

Operation 2104 illustrates selecting at least one of a virtual world, a social networking website, an online game, an online educational experience, a networked game, or a single-player game. For example, as shown in FIG. 1, selector module 106 may select at least one of a virtual world, a social networking website, an online game, an online educational experience, a networked game, or a single-player game. In one instance, selector module 106 can select a virtual world. A virtual world may include a computer-based simulated environment intended for its users to inhabit and interact via avatars, such as second life. A social networking website may include a website for observing and/or interacting with one or more personal and/or professional relationships between individuals. Some examples of a social networking website may include MySpace, GeoCities, Facebook, and/or Linkedin. In one instance, selector module 106 may select Facebook as the social networking website and may include directions to Facebook to implement a color scheme including bright colors, such as yellow and light blue, for preventing the onset of depression in a depression prone viewer. An online game may include a game played over a network, such as hardwired terminals, a wireless network, a modem network, a video console, and/or the internet. Some online games may include virtual worlds and/or virtual communities. Examples of online games may include World of Warcraft (WoW), Final Fantasy XI, Lineage II, Guild Wars, and/or RuneScape. An online educational experience may include a tutorial, a lesson, and/or an online class. Some examples of an online educational experience may include a HTML tutorial, an online piano lesson, and/or an online degree program from the University of Phoenix. A networked game may include any game played by more than one player and may be played on a computer. An example of a networked game may include World of Warcraft (WoW). A single-player game may include any game that can be played by one player and that may or may not be played on a computer. Examples of a single-player game includes solitaire, puzzle games such as Tetris, Call of Duty, and Guitar Hero. In some instances, selector module 106 may include a computer processor.

Figure 22:
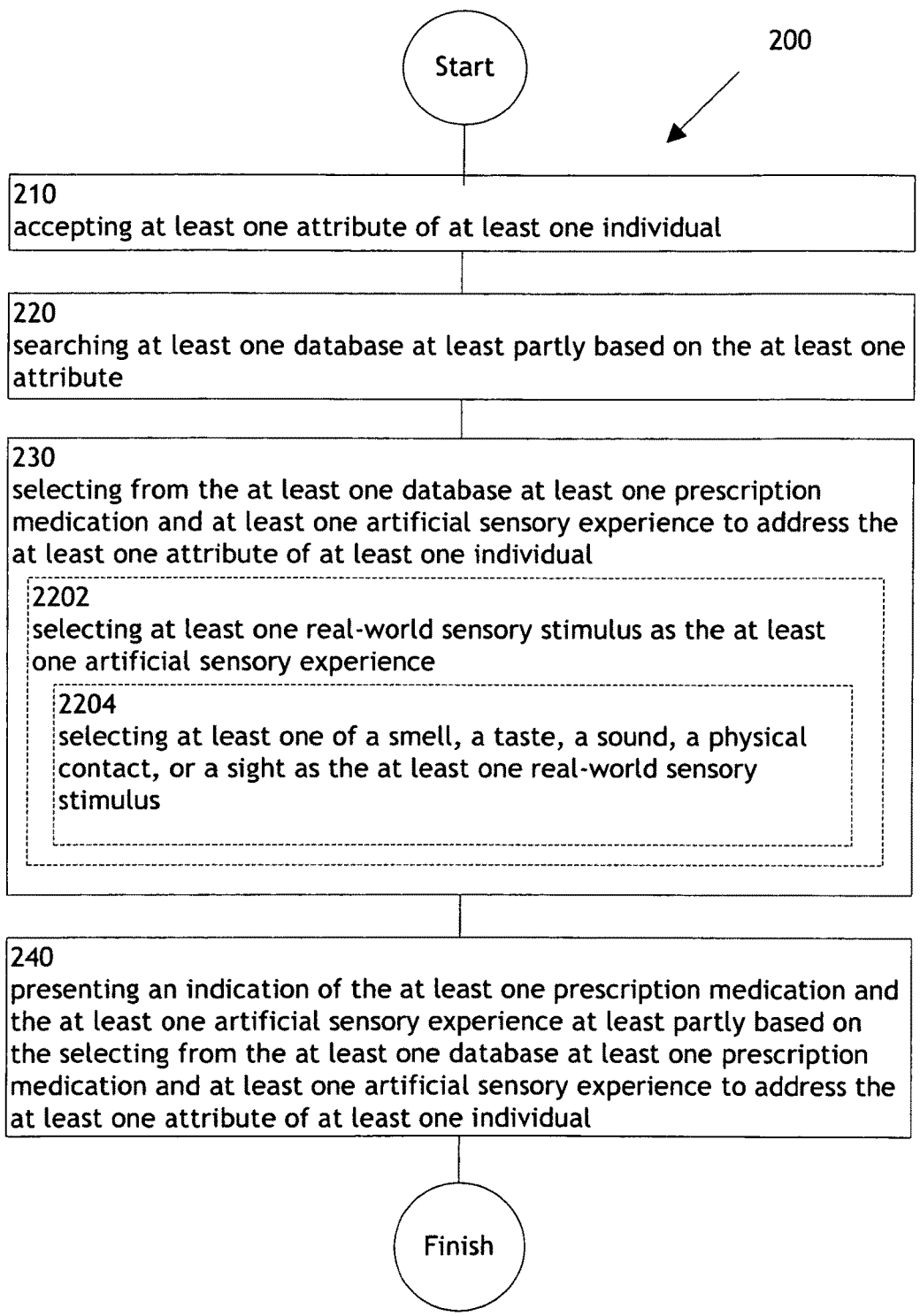
FIG. 22 illustrates an alternative embodiment of the operational flow of FIG. 2.

FIG. 22 illustrates alternative embodiments of the example operational flow 200 of FIG. 2. FIG. 22 illustrates example embodiments where operation 230 may include at least one additional operation. Additional operations may include an operation 2202, and/or an operation 2204.

Operation 2202 illustrates selecting at least one real-world sensory stimulus as the at least one artificial sensory experience. For example, as shown in FIG. 1, selector module 106 may select at least one real-world sensory stimulus as the at least one artificial sensory experience. In one instance, selector module 106 can select a real-world sensory stimulus including an aroma as an artificial sensory experience. Some examples of a real-world sensory stimulus may include aromas and/or smells, sounds, sights, touch, pressure, temperature and/or heat, and/or vibration. In some instances, selector module 106 may include a computer processor. Further, operation 2204 illustrates selecting at least one of a smell, a taste, a sound, a physical contact, or a sight as the at least one real-world sensory stimulus. For example, as shown in FIG. 1, selector module 106 may select at least one of a smell, a taste, a sound, a physical contact, or a sight as the at least one real-world sensory stimulus. In one example, selector module 106 selects a smell and a taste as a real-world sensory stimulus. A smell may include any property detected by the nose and/or olfactory system. A taste may include any flavor and/or property detected by the tongue and/or taste buds. A sound may include any sound wave that may be detected by the eardrum. A physical contact may include anything related to touch, feel, and/or detection by the skin and/or body, and/or physical activity including exercise. In one instance, selector module 106 may select a physical contact including physical exercise associated with participating in playing a tennis game on a Nintendo Wii video game console, for example. A sight may include any image, and/or light detected by the eyes. In some instances, selector module 106 may include a computer processor.

Figure 23:
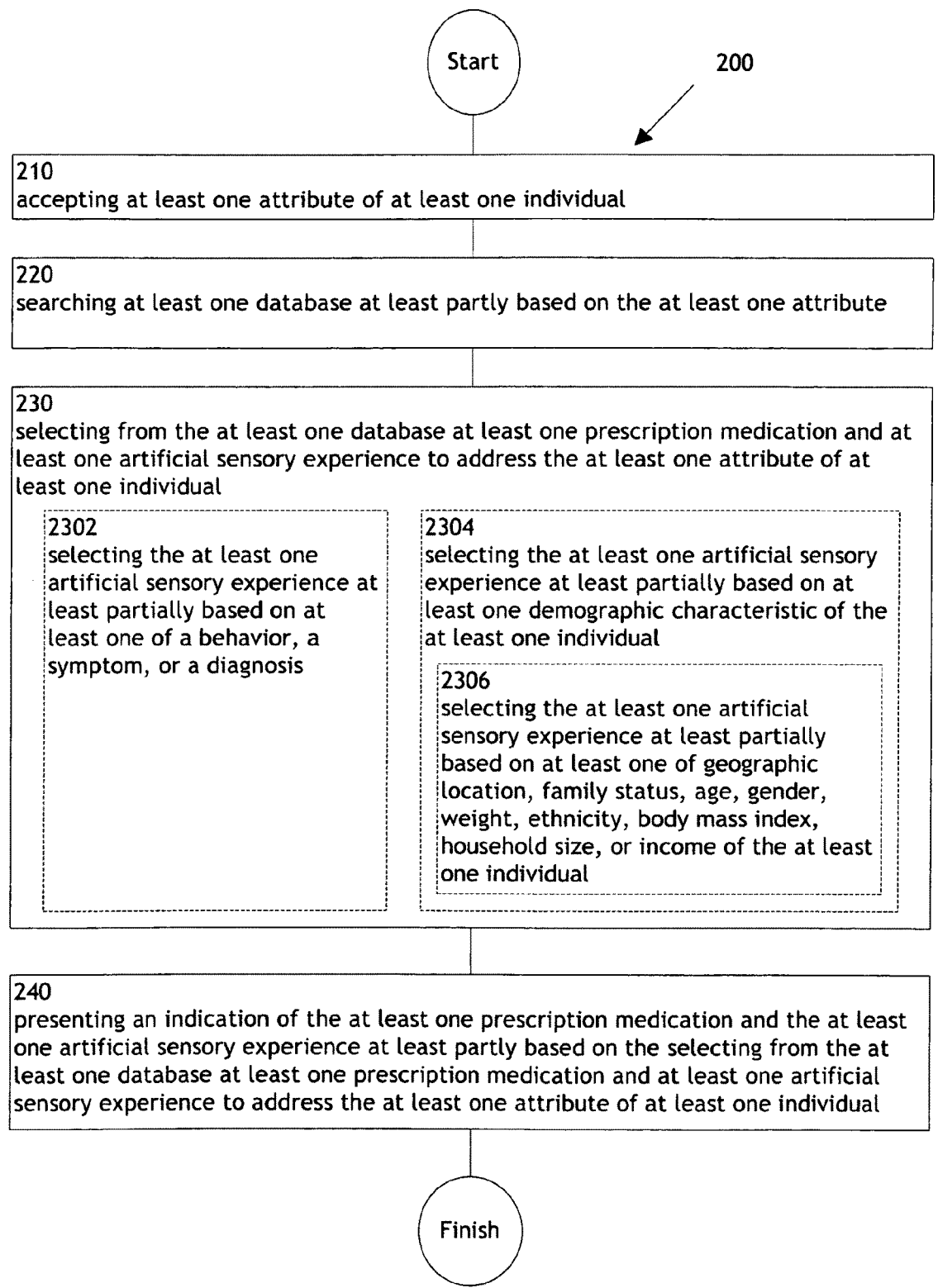
FIG. 23 illustrates an alternative embodiment of the operational flow of FIG. 2.

FIG. 23 illustrates alternative embodiments of the example operational flow 200 of FIG. 2. FIG. 23 illustrates example embodiments where operation 230 may include at least one additional operation. Additional operations may include an operation 2302, an operation 2304, and/or an operation 2306.

Operation 2302 illustrates selecting the at least one artificial sensory experience at least partially based on at least one of a behavior, a symptom, or a diagnosis. For example, as shown in FIG. 1, selector module 106 may select the at least one artificial sensory experience at least partially based on at least one of a behavior, a symptom, or a diagnosis. In one example, selector module 106 can select an artificial sensory experience based on behavior entered by a user 118 via a user interface 116. A behavior may include the manner in which a person and/or thing acts and/or reacts. A symptom may include a manifestation, sign, and/or an indication of the presence of a disease and/or some other disorder and/or abnormality. A diagnosis may include identifying a disease and/or condition by its signs and/or symptoms. For example, selector module 106 and/or system 100 may select an immersive virtual reality experience as the at least one artificial sensory experience at least partially based on a pain symptom and/or a third-degree burn diagnosis. In some instances, selector module 106 may include a computer processor.

Operation 2304 illustrates selecting the at least one artificial sensory experience at least partially based on at least one demographic characteristic of the at least one individual. For example, as shown in FIG. 1, selector module 106 may select the at least one artificial sensory experience at least partially based on at least one demographic characteristic of the at least one individual. In one example, selector module 106 can select an artificial sensory experience based on a demographic characteristic the at least one individual. A demographic characteristic may include a socioeconomic, age, gender, and/or other similar factor defining a certain population. For example, selector module 106 and/or system 100 may select a virtual reality experience such as a Sesame Street or Disney-themed experience as the at least one artificial sensory experience at least partially based on an indication that the individual is aged 6-10 years old. In some instances, selector module 106 may include a computer processor.

Further, operation 2306 illustrates selecting the at least one artificial sensory experience at least partially based on at least one of geographic location, family status, age, gender, weight, ethnicity, body mass index, household size, or income of the at least one individual. For example, as shown in FIG. 1, selector module 106 may select the at least one artificial sensory experience at least partially based on at least one of geographic location, family status, age, gender, weight, ethnicity, body mass index, household size, or income of the at least one individual. In one example, selector module 106 can select the artificial sensory experience based on an age and a weight associated with the at least one individual. A geographic location may include a location where an individual currently resides, has resided in the past, and/or has visited. A family status may include marital status, status and/or presence of children, and/or the status and/or health of extended family. In some instances, selector module 106 may include a computer processor.

Figure 24:
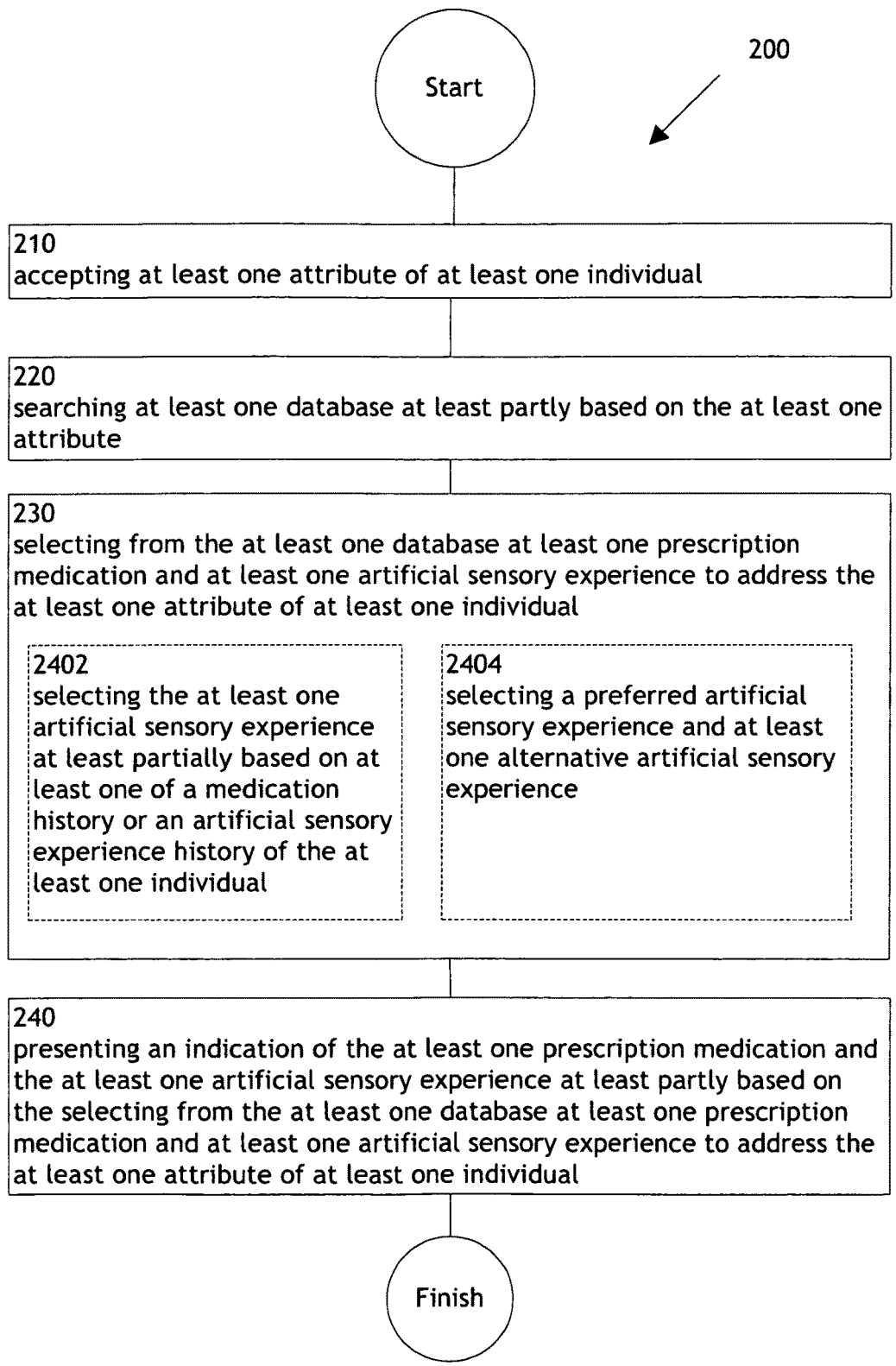
FIG. 24 illustrates an alternative embodiment of the operational flow of FIG. 2.

FIG. 24 illustrates alternative embodiments of the example operational flow 200 of FIG. 2. FIG. 24 illustrates example embodiments where operation 230 may include at least one additional operation. Additional operations may include an operation 2402, and/or an operation 2404.

Operation 2402 illustrates selecting the at least one artificial sensory experience at least partially based on at least one of a medication history or an artificial sensory experience history of the at least one individual. For example, as shown in FIG. 1, selector module 106 may select the at least one artificial sensory experience at least partially based on at least one of a medication history or an artificial sensory experience history of the at least one individual. In one instance, selector module 106 can select an artificial sensory experience based on an artificial sensory experience history of the at least one individual. An artificial sensory experience history may include any record of at least one administered artificial sensory experience history. For example, system 100 and/or selector module 106 may select a modified facebook webpage having a cheerful color scheme at least partly based on a facebook usage history for an individual with signs of depression. In some instances, selector module 106 may include a computer processor.

Operation 2404 illustrates selecting a preferred artificial sensory experience and at least one alternative artificial sensory experience. For example, as shown in FIG. 1, selector module 106 may select a preferred artificial sensory experience and at least one alternative artificial sensory experience. In one example, selector module 106 can select a preferred artificial sensory experience and at least one alternative artificial sensory experience. A preferred artificial sensory experience may include a more desirable artificial sensory experience due to a lack of and/or a reduced level of side effects, reduced impact upon the individual, and/or increased compatibility with another medications and/or treatment. An alternative artificial sensory experience may include any artificial sensory experience in addition to the preferred artificial sensory experience and may be less desirable than the preferred artificial sensory experience due to side effects and/or increased impact upon the individual. In some instances, selector module 106 may include a computer processor.

Figure 25:
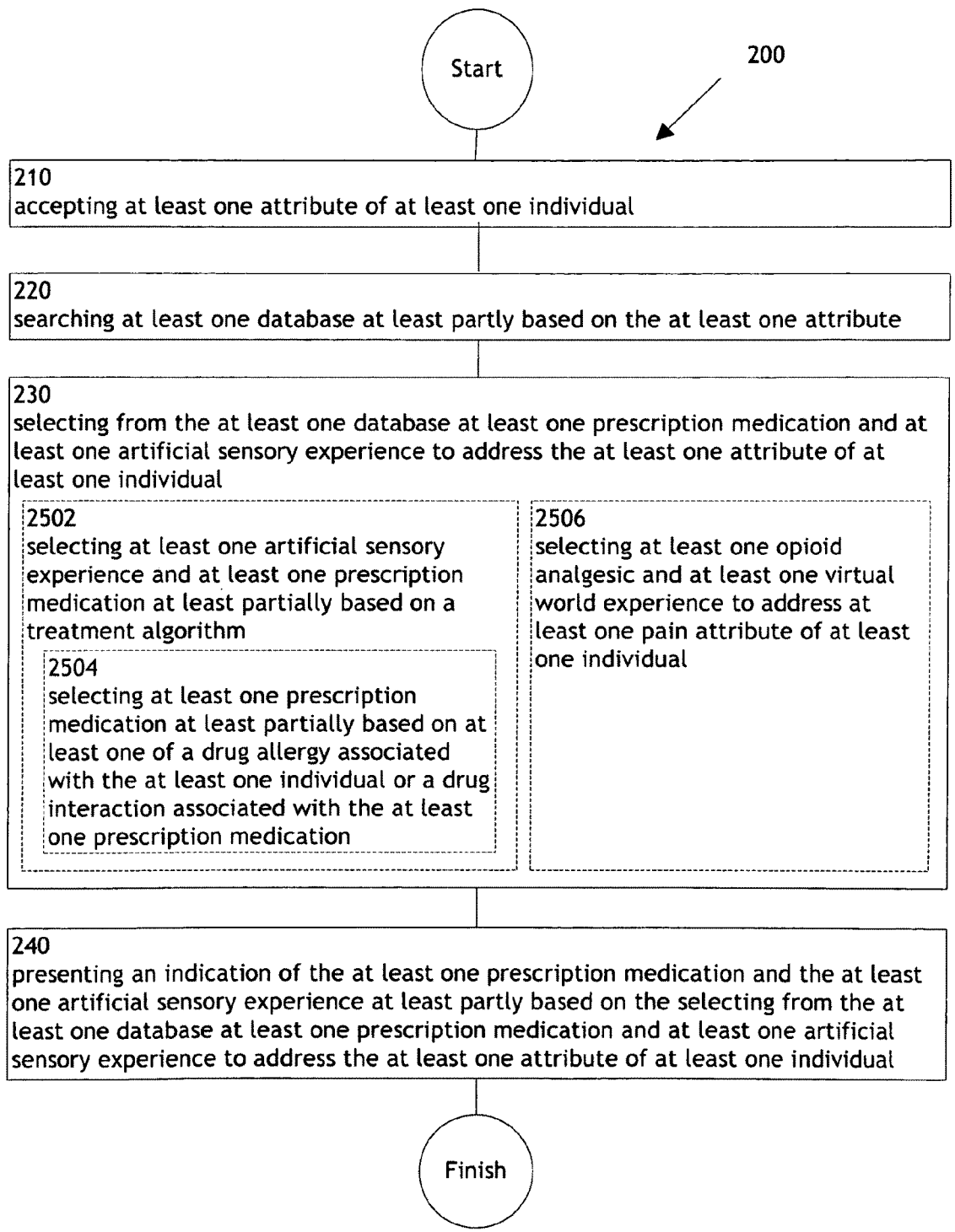
FIG. 25 illustrates an alternative embodiment of the operational flow of FIG. 2.

FIG. 25 illustrates alternative embodiments of the example operational flow 200 of FIG. 2. FIG. 25 illustrates example embodiments where operation 230 may include at least one additional operation. Additional operations may include an operation 2502, an operation 2504, and/or an operation 2506.

Operation 2502 illustrates selecting at least one artificial sensory experience and at least one prescription medication at least partially based on a treatment algorithm. For example, as shown in FIG. 1, selector module 106 may select at least one artificial sensory experience and at least one prescription medication at least partially based on a treatment algorithm. In one instance, selector module 106 can select an artificial sensory experience and a prescription medication based on a computer software treatment algorithm. A treatment algorithm may include any computation, formula, statistical survey, and/or look-up table for determining and/or selecting a suitable artificial sensory experience and prescription medication combination. Some examples may include a computer software algorithm, a calculator, a flowchart, and/or a decision tree. For example, system 100 and/or selector module 106 may, based on an accepted pain symptom of an individual, access a lookup chart that matches the pain symptom with a pain medication, such as naproxen, and a virtual experience, such as World of Warcraft. Such a combination therapy may be particularly effective in ameliorating the pain symptom in the individual. In some instances, selector module 106 may include a computer processor.

Further, operation 2504 illustrates selecting at least one prescription medication at least partially based on at least one of a drug allergy associated with the at least one individual or a drug interaction associated with the at least one prescription medication. For example, as shown in FIG. 1, selector module 106 may select at least one prescription medication at least partially based on at least one of a drug allergy associated with the at least one individual or a drug interaction associated with the at least one prescription medication. In one example, selector module 106 can select a prescription medication based on a drug allergy associated with the at least one individual. A drug allergy may include any allergy to a drug and/or drug intolerance. Some examples of a drug allergy may include penicillin allergies, codeine allergies, and/or allergies to a dye in a drug. A drug interaction may include an undesirable and/or unwanted reaction between two or more drugs and/or medications. For example, the system 100 and/or selector module 106 can select a prescription medication other than those that might cause a side effect in an individual, perhaps because of a known predisposition to the side effect (e.g., an allergy) or because of a known drug-drug interaction relevant to the individual based on the individual's medication regimen. In this way, risk of side effects can be lessened. In some instances, selector module 106 may include a computer processor.

Operation 2506 illustrates selecting at least one opioid analgesic and at least one virtual world experience to address at least one pain attribute of at least one individual. For example, as shown in FIG. 1, selector module 106 may select from a prescription medication database at least one opioid analgesic and at least one virtual world experience to address at least one pain attribute of at least one individual. In one example, selector module 106 can select an opioid analgesic including morphine and a virtual world experience including an online game to address a pain attribute of at least one individual named Mary Andersen. In some instances, selector module 106 may include a computer processor.

Figure 26:
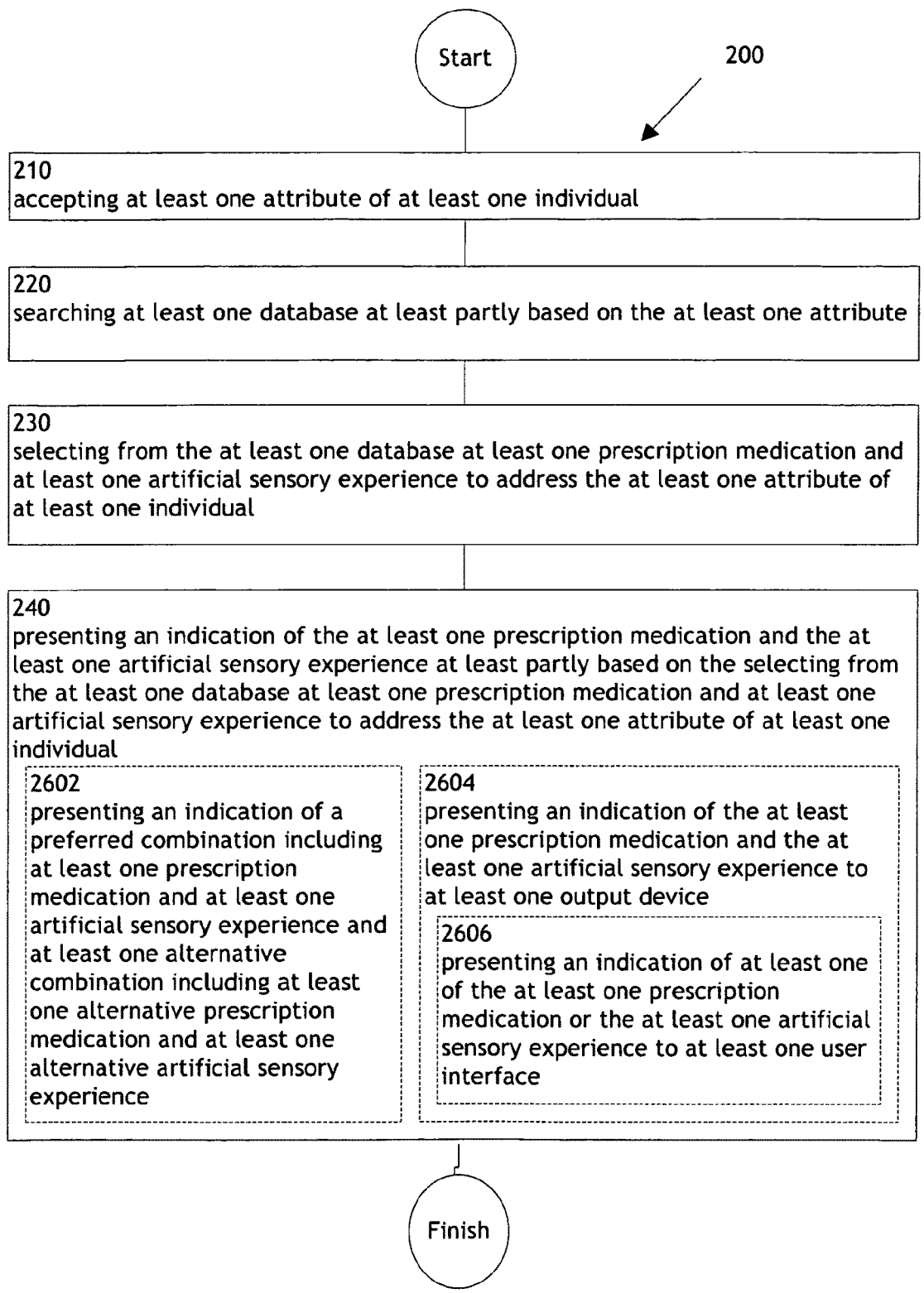
FIG. 26 illustrates an alternative embodiment of the operational flow of FIG. 2.

FIG. 26 illustrates alternative embodiments of the example operational flow 200 of FIG. 2. FIG. 26 illustrates example embodiments where operation 240 may include at least one additional operation. Additional operations may include an operation 2602, an operation 2604, and/or an operation 2606.

Operation 2602 illustrates presenting an indication of a preferred combination including at least one prescription medication and at least one artificial sensory experience and at least one alternative combination including at least one alternative prescription medication and at least one alternative artificial sensory experience. For example, as shown in FIG. 1, presenter module 108 may present an indication of a preferred combination including at least one prescription medication and at least one artificial sensory experience and at least one alternative combination including at least one alternative prescription medication and at least one alternative artificial sensory experience. In one instance, presenter module 108 can present an indication of a preferred combination to an individual 134 including a prescription medication and an artificial sensory experience along with an alternative combination including an alternative prescription medication and an alternative artificial sensory experience. Individual 134 may include a single individual, multiple individuals, and/or an entity. A preferred combination may include a more desirable combination due to a lack of and/or a reduced number of and/or level of side effects, reduced impact upon the administered individual, and/or increased compatibility with another medications and/or treatment. An alternative combination may include any combination in addition to the preferred combination and may be ostensibly less desirable than the preferred artificial sensory experience because of a potential side effect and/or impact upon the administered individual. Presentation of alternative combinations may provide benefits to the individual in terms of accessibility, affordability, and/or personal preference of medication and/or artificial sensory experience. In some instances, presenter module 108 may include a computer processor.

Operation 2604 illustrates presenting an indication of the at least one prescription medication and the at least one artificial sensory experience to at least one output device. For example, as shown in FIG. 1, presenter module 108 may present an indication of the at least one prescription medication and the at least one artificial sensory experience to at least one output device. In one example, presenter module 108 can present an indication of a prescription medication and an artificial sensory experience to an output device 130 including a printer at a health clinic. An output device may include any hardware device configured for receiving computer output. Some examples of an output device may include a printer, a monitor, a mobile phone, a speaker, and/or a visual display unit. The output device may be used by individual 134. In some instances, presenter module 108 may include a computer processor.

Further, operation 2606 illustrates presenting an indication of at least one of the at least one prescription medication or the at least one artificial sensory experience to at least one user interface. For example, as shown in FIG. 1, presenter module 108 may present an indication of at least one of the at least one prescription medication or the at least one artificial sensory experience to at least one user interface. In one instance, presenter module 108 can present an indication of a prescription medication and an artificial sensory experience to a user interface. A user interface may include means by which an individual may interact with a system. Some examples of a user interface may include a touchscreen, a graphical user interface, a tactile interface, and/or a live user interface. In some instances, presenter module 108 may include a computer processor.

Figure 27:
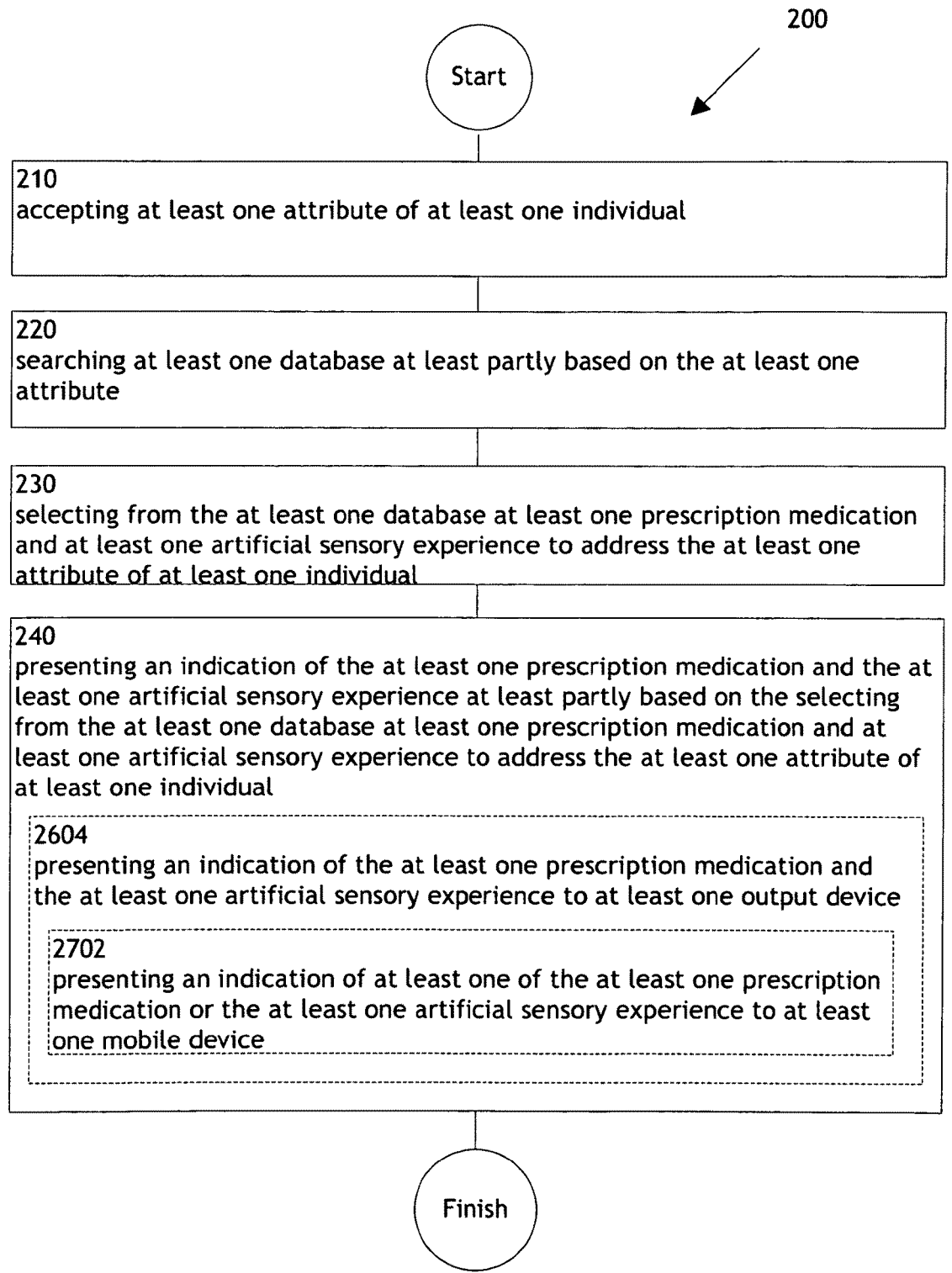
FIG. 27 illustrates an alternative embodiment of the operational flow of FIG. 2.

FIG. 27 illustrates alternative embodiments of the example operational flow 200 of FIG. 2. FIG. 27 illustrates example embodiments where operation 240 may include at least one additional operation. Additional operations may include an operation 2702. Further, operation 2702 illustrates presenting an indication of at least one of the at least one prescription medication or the at least one artificial sensory experience to at least one mobile device. For example, as shown in FIG. 1, presenter module 108 may present an indication of at least one of the at least one prescription medication or the at least one artificial sensory experience to at least one mobile device. In one instance, presenter module 108 can present an indication of a prescription medication to a mobile device 132. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, presenter module 108 may include a computer processor.

Figure 28:
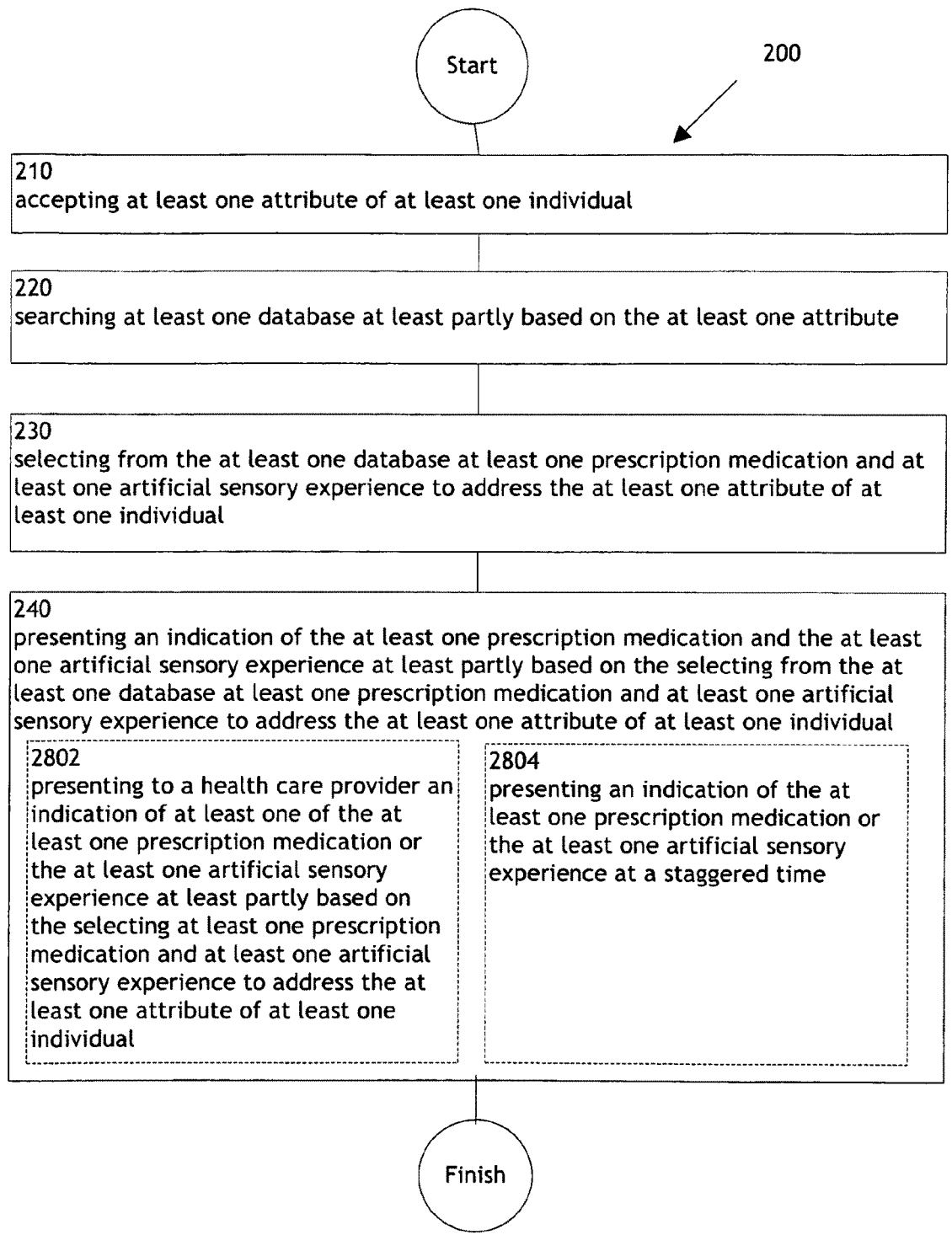
FIG. 28 illustrates an alternative embodiment of the operational flow of FIG. 2.

FIG. 28 illustrates alternative embodiments of the example operational flow 200 of FIG. 2. FIG. 28 illustrates example embodiments where operation 240 may include at least one additional operation. Additional operations may include an operation 2802, and/or an operation 2804.

Operation 2802 illustrates presenting to a health care provider an indication of at least one of the at least one prescription medication or the at least one artificial sensory experience at least partly based on the selecting at least one prescription medication and at least one artificial sensory experience to address the at least one attribute of at least one individual. For example, as shown in FIG. 1, presenter module 108 may present to a health care provider an indication of at least one of the at least one prescription medication or the at least one artificial sensory experience at least partly based on the selecting at least one prescription medication and at least one artificial sensory experience to address an attribute of an individual. In one example, presenter module 108 can present to a health care provider 128 an indication of a prescription medication based on the selecting at least one prescription medication and at least one artificial sensory experience to address the at least one attribute 120 of at least one individual. A health care provider may include a pharmacy, a pharmaceutical company, a medical device company, a research institution, a computer software and/or computer hardware company, a website, a nurse and/or a physician. In some instances, presenter module 108 may include a computer processor.

Operation 2804 illustrates presenting an indication of the at least one prescription medication or the at least one artificial sensory experience at a staggered time. For example, as shown in FIG. 1, presenter module 108 may present an indication of at least one of the at least one prescription medication or the at least one artificial sensory experience at a staggered time. In one example, presenter module 108 can present an indication of a series of prescription medications and an artificial sensory experience at staggered times. A staggered time may include presenting an indication of the at least one drug and/or artificial sensory experience at overlapping times and/or at different times, including alternating times. For example, at least one drug and an artificial sensory experience may be administered at an initial time and the same or a different drug may be administered when the first-administered at least one drug is at its peak effect. In another example, at least one drug and an artificial sensory experience may be administered at an initial time and the same or a different drug may be administered when the first administered at least one drug is at its lowest effect. In another example, an artificial sensory experience may be administered at an initial time and at least one prescription medication at a later time. The at least one artificial sensory experience and/or the at least one prescription medication may be administered at any number of times either concurrently, partially concurrently, or not concurrently. In some instances, presenter module 108 may include a computer processor.

Figure 29:
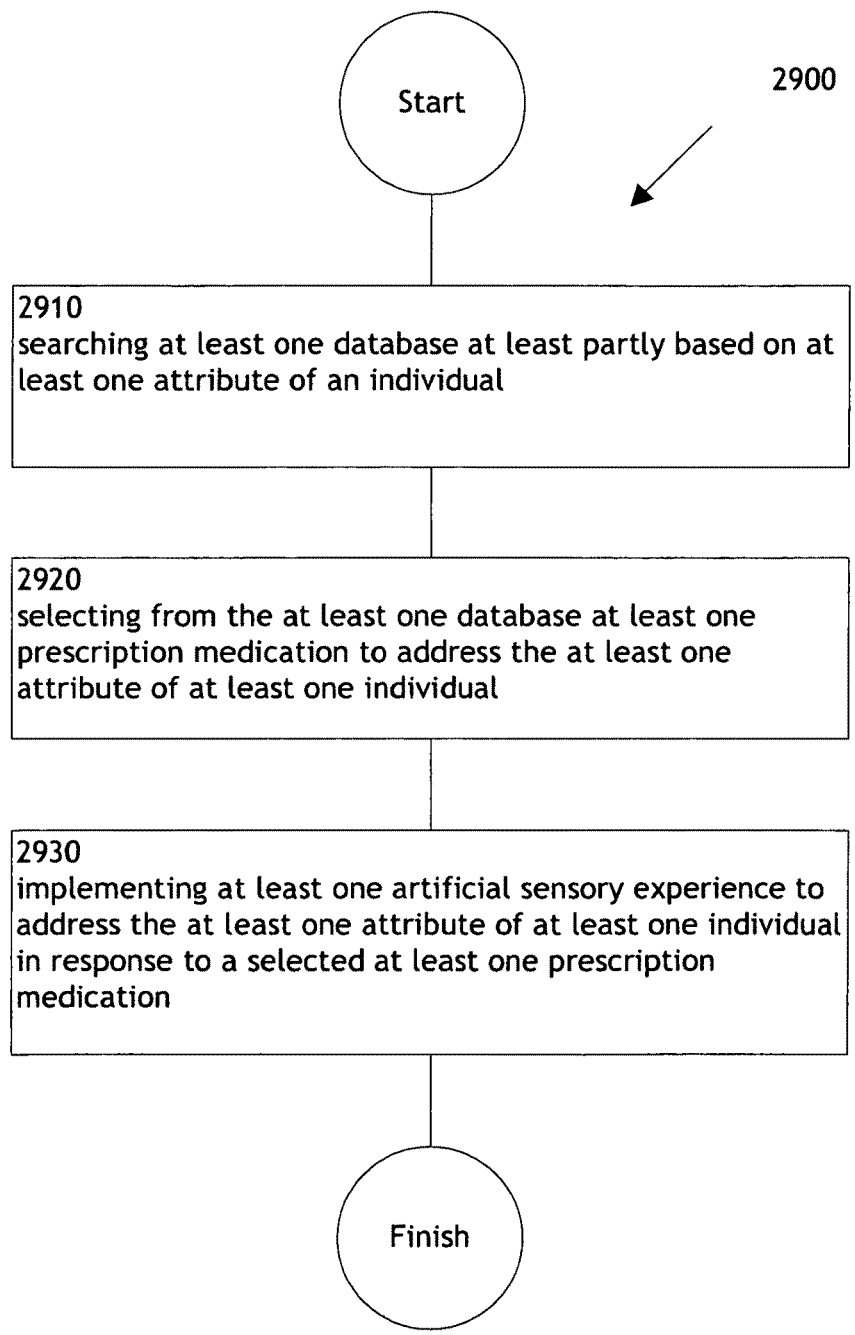
FIG. 29 illustrates an operational flow representing example operations related to selecting a combination of at least one prescription medication and at least one artificial sensory experience.

FIG. 29 illustrates an operational flow 2900 representing example operations related to querying at least one database at least partly based on at least one attribute of an individual, selecting from the at least one database at least one prescription medication to address the at least one attribute of at least one individual, and/or implementing at least one artificial sensory experience to address the at least one attribute of at least one individual in response to a selected at least one prescription medication. In FIG. 29, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 2900 moves to an operation 2910. Operation 2910 depicts querying at least one database at least partly based on at least one attribute of an individual. For example, as shown in FIG. 1, querier module 104 may search at least one database at least partly based on at least one attribute of an individual. In one instance, querier module 104 may search medication database 124 and artificial sensory experience database 126 based on an attribute 120 including an indication of hypertension associated with an individual named John Smith. In some instances, querier module 104 may include a computer processor.

Then, operation 2920 depicts selecting from the at least one database at least one prescription medication to address the at least one attribute of at least one individual. For example, as shown in FIG. 1, selector module 106 may select from the at least one database at least one prescription medication to address the at least one attribute of at least one individual. In one example and continuing with the previous example, selector module 106 may select from medication database 124 and artificial sensory experience database 126 a prescription medicine for addressing the attribute 120 including an indication of hypertension associated with an individual named John Smith. In some instances, selector module 106 may include a computer processor.

Then, operation 2930 depicts implementing at least one artificial sensory experience to address the at least one attribute of at least one individual in response to a selected at least one prescription medication. For example, as shown in FIG. 1, implementer module 138 may implement at least one artificial sensory experience to address the at least one attribute of at least one individual in response to a selected at least one prescription medication. In one instance and continuing with the previous example, implementer module 106 may implement an artificial sensory experience including a virtual world for addressing the attribute 120 including an indication of hypertension associated with an individual named John Smith in response to a selected prescription medication from a medication database 124. In some instances, selector module 106 may include a computer processor.

Figure 30:
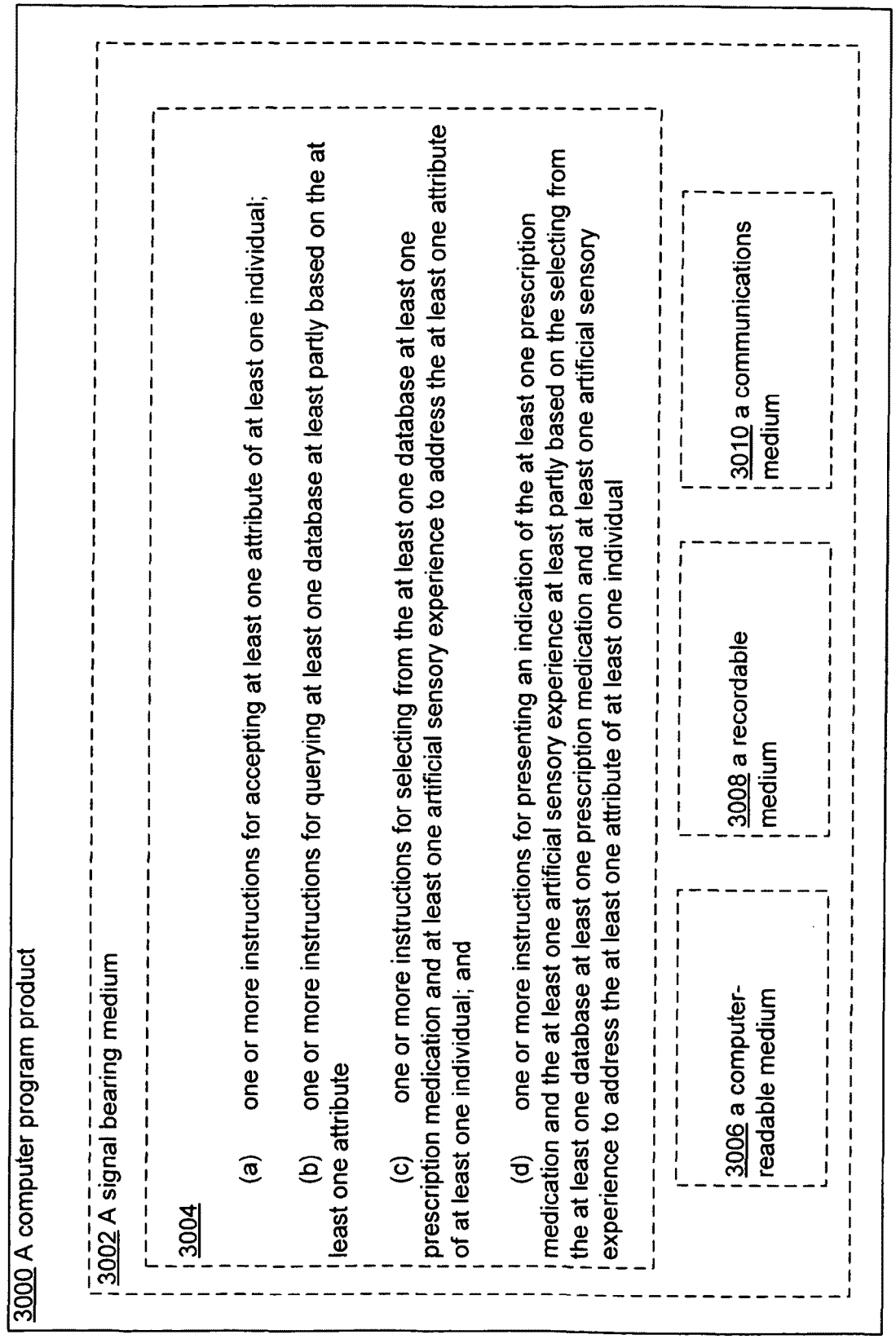
FIG. 30 illustrates a computer program product related to selecting a combination of at least one prescription medication and at least one artificial sensory experience.

FIG. 30 illustrates a partial view of an example computer program product 3000 that includes a computer program 3004 for executing a computer process on a computing device. An embodiment of the example computer program product 3000 is provided using a signal-bearing medium 3002, and may include one or more instructions for accepting at least one attribute of at least one individual; one or more instructions for querying at least one database at least partly based on the at least one attribute; one or more instructions for selecting from the at least one database at least one prescription medication and at least one artificial sensory experience to address the at least one attribute of at least one individual; and one or more instructions for presenting an indication of the at least one prescription medication and the at least one artificial sensory experience at least partly based on the selecting from the at least one database at least one prescription medication and at least one artificial sensory experience to address the at least one attribute of at least one individual. The one or more instructions may be, for example, computer executable and/or logic-implemented instructions. In one implementation, the signal-bearing medium 3002 may include a computer-readable medium 3006. In one implementation, the signal bearing medium 3002 may include a recordable medium 3008. In one implementation, the signal bearing medium 3002 may include a communications medium 3010.

Figure 31:
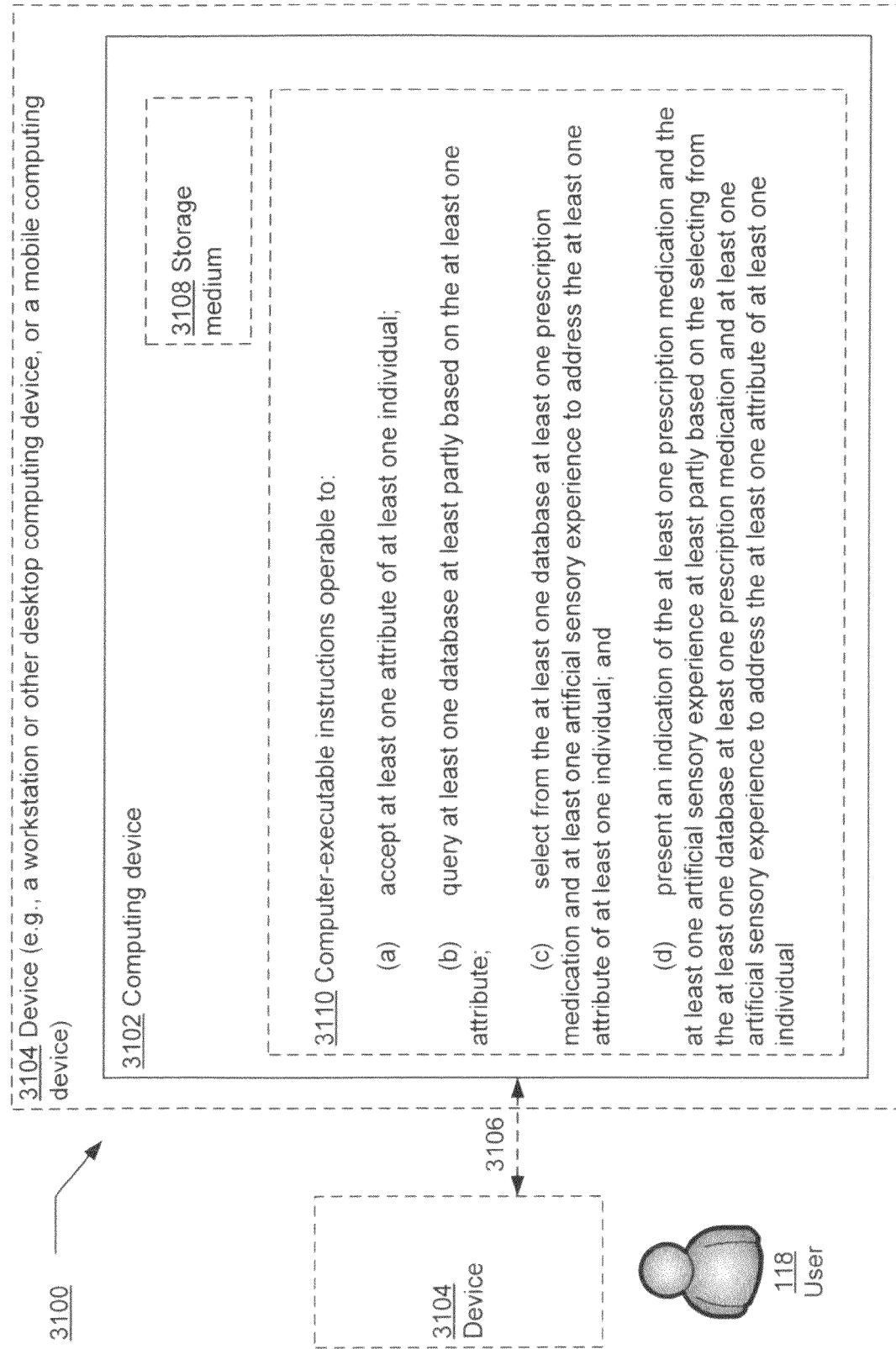
FIG. 31 illustrates a system related to selecting a combination of at least one prescription medication and at least one artificial sensory experience.

FIG. 31 illustrates an example system 3100 in which embodiments may be implemented. The system 3100 includes a computing system environment. The system 3100 also illustrates the user 118 using a device 3104, which is optionally shown as being in communication with a computing device 3102 by way of an optional coupling 3106. The optional coupling 3106 may represent a local, wide-area, or peer-to-peer network, or may represent a bus that is internal to a computing device (e.g., in example embodiments in which the computing device 3102 is contained in whole or in part within the device 3104). A storage medium 3108 may be any computer storage media.

The computing device 3102 includes computer-executable instructions 3110 that when executed on the computing device 3102 cause the computing device 3102 to accept at least one attribute of at least one individual; query at least one database at least partly based on the at least one attribute; select from the at least one database at least one prescription medication and at least one artificial sensory experience to address the at least one attribute of at least one individual; and present an indication of the at least one prescription medication and the at least one artificial sensory experience at least partly based on the selecting from the at least one database at least one prescription medication and at least one artificial sensory experience to address the at least one attribute of at least one individual. As referenced above and as shown in FIG. 31, in some examples, the computing device 3102 may optionally be contained in whole or in part within the device 3104.

In FIG. 31, then, the system 3100 includes at least one computing device (e.g., 3102 and/or 3104). The computer-executable instructions 3110 may be executed on one or more of the at least one computing device. For example, the computing device 3102 may implement the computer-executable instructions 3110 and output a result to (and/or receive data from) the computing device 3104. Since the computing device 3102 may be wholly or partially contained within the computing device 3104, the device 3104 also may be said to execute some or all of the computer-executable instructions 3110, in order to be caused to perform or implement, for example, various ones of the techniques described herein, or other techniques.

The device 3104 may include, for example, a portable computing device, workstation, or desktop computing device. In another example embodiment, the computing device 3102 is operable to communicate with the device 3104 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Figure 32:
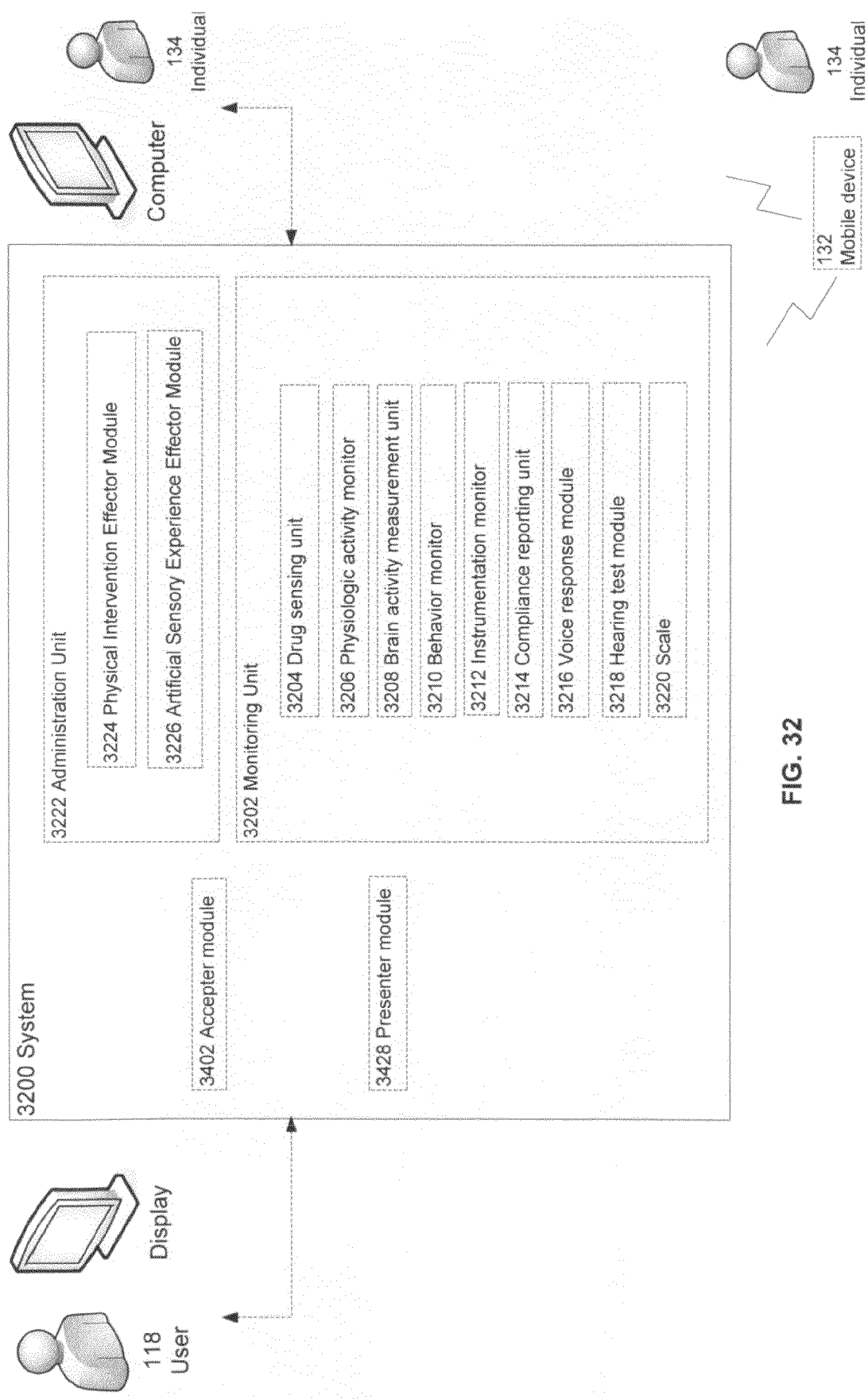
FIG. 32 illustrates an exemplary environment in which one or more technologies may be implemented.

FIG. 32 illustrates system 3200 for accepting an indication of an individual's compliance with an artificial sensory experience and/or presenting an indication of a bioactive agent at least partly based on the indication of the individual's compliance with the artificial sensory experience. The system 3200 may include accepter module 3402, presenter module 3428, monitoring unit 3202, and/or administration unit 3222. Administration unit 3222 may include physical intervention effector module 3224 and/or artificial sensory experience effector module 3226. Monitoring unit 3202 may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Additionally, system 3200 may include mobile device 132.

Figure 33:
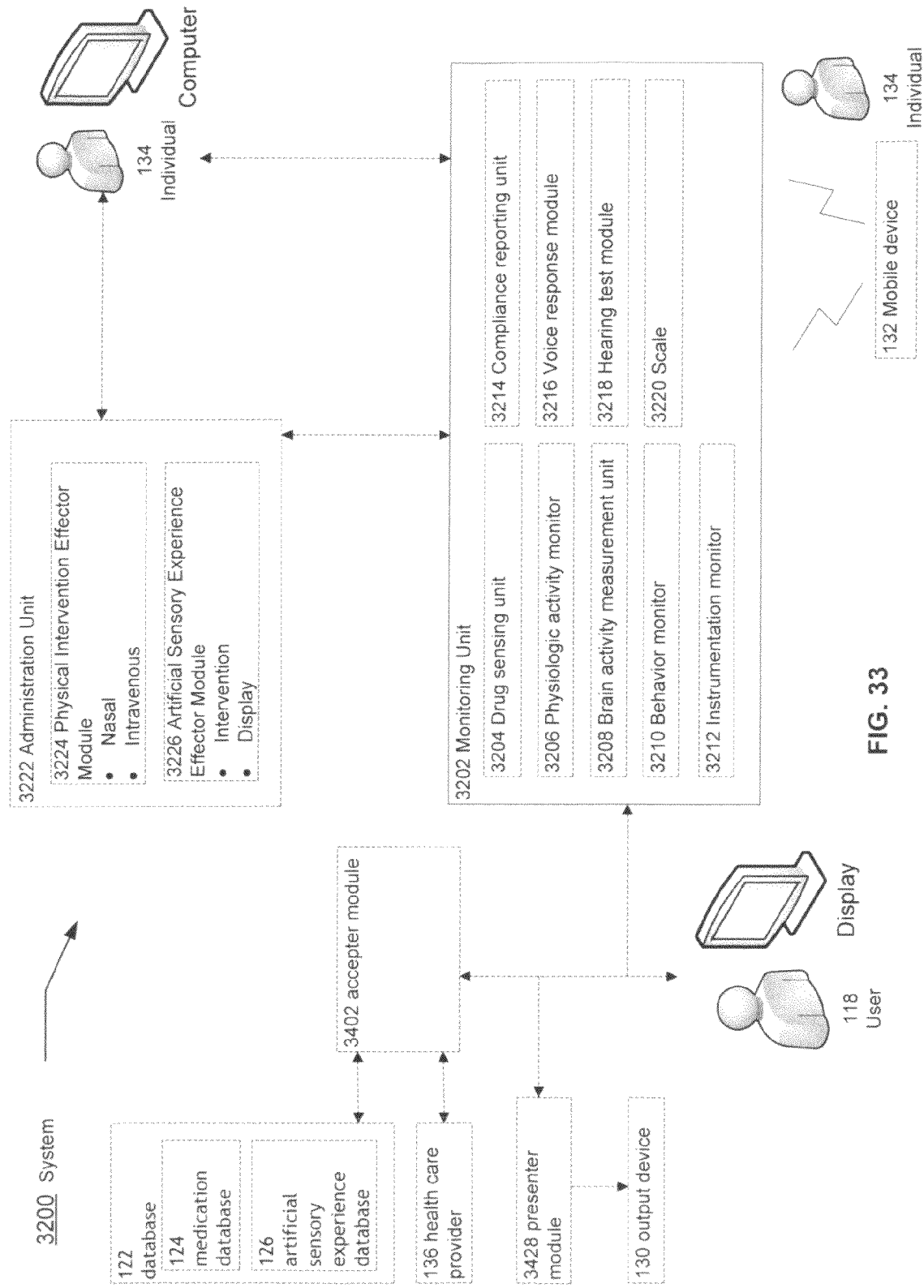
FIG. 33 illustrates an exemplary environment in which one or more technologies may be implemented.

FIG. 33 illustrates system 3200 for accepting an indication of an individual's compliance with an artificial sensory experience and/or presenting an indication of a bioactive agent at least partly based on the indication of the individual's compliance with the artificial sensory experience. The system 3200 may include accepter module 3402, presenter module 3428, monitoring unit 3202, and/or administration unit 3222. Accepter module 3402 may receive and/or transmit information and/or data to and/or from user 118, database 122, presenter module 3428, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 3222 may include physical intervention effector module 3224 and/or artificial sensory experience effector module 3226. Additionally, mobile device 132 may communicate with acceptor module 3402, presenter module 3428, healthcare provider 136, user 118, individual 134, monitoring unit 3202, and/or administration unit 3222.

Figure 34:
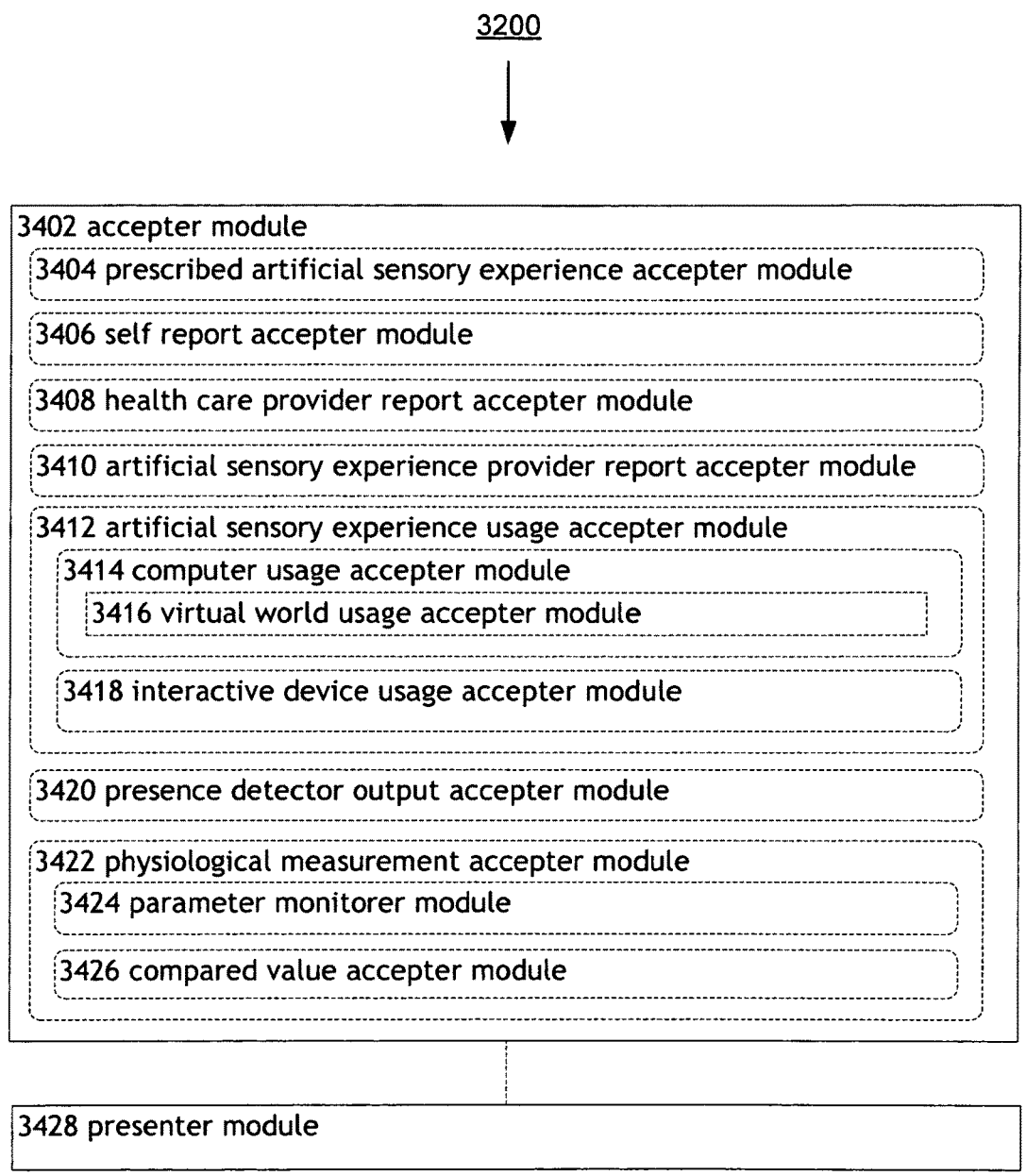
FIG. 34 illustrates an exemplary environment in which one or more technologies may be implemented.

FIG. 34 further illustrates system 3200 including accepter module 3402 and/or presenter module 3428. Accepter module 3402 may include prescribed artificial sensory experience accepter module 3404, self report accepter module 3406, health care provider report accepter module 3408, artificial sensory experience provider report accepter module 3410, artificial sensory experience usage accepter module 3412, presence detector output accepter module 3420, and/or physiological measurement accepter module 3422. Artificial sensory experience usage accepter module 3412 may include computer usage accepter module 3414. Computer usage accepter module 3414 may include virtual world usage accepter module 3416. Physiological measurement accepter module 3422 may include parameter monitorer module 3424 and/or compared value accepter module 3426.

Figure 35:
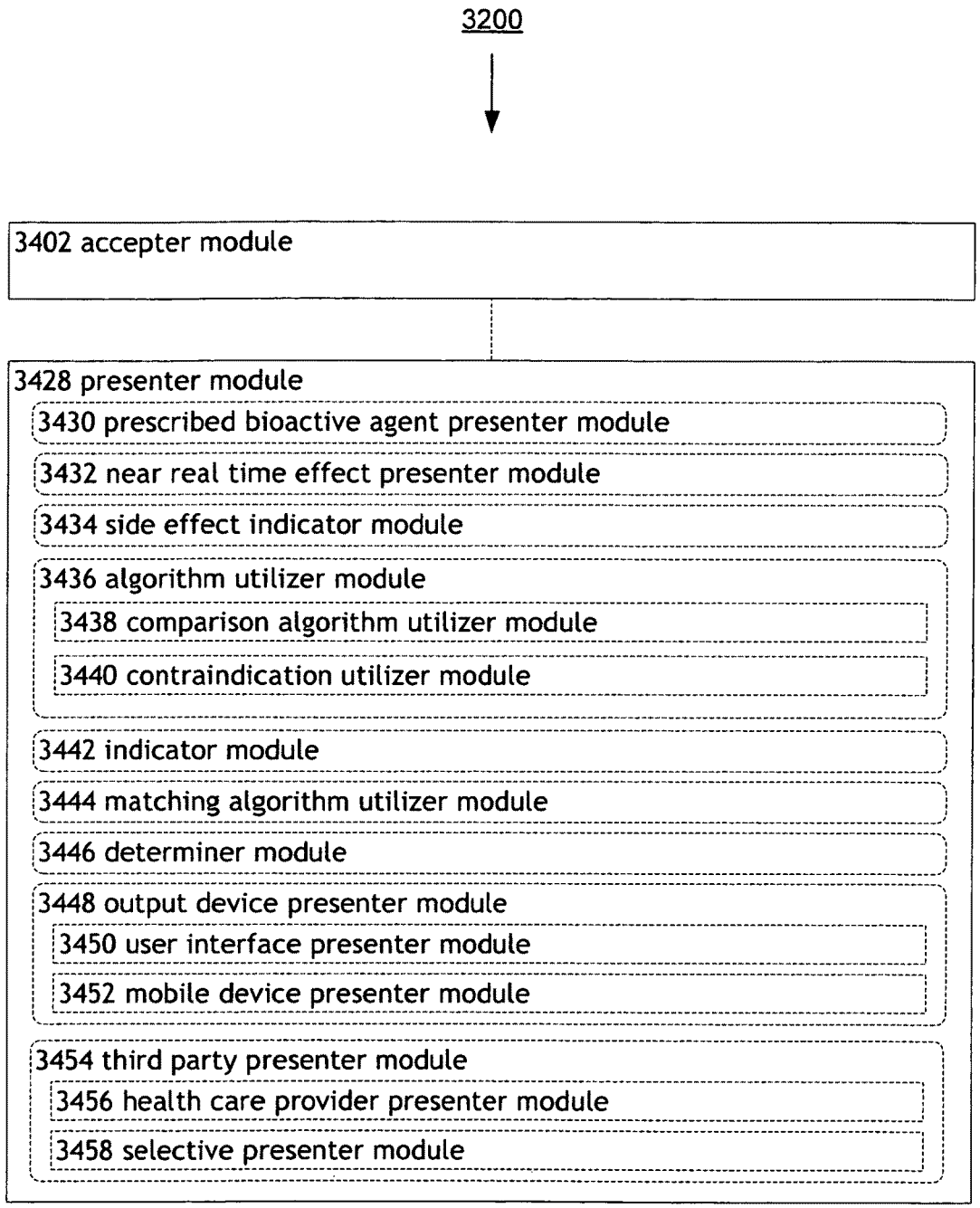
FIG. 35 illustrates an exemplary environment in which one or more technologies may be implemented.

FIG. 35 further illustrates system 3200 including accepter module 3402 and/or presenter module 3428. Presenter module 3428 may further include prescribed bioactive agent presenter module 3430, near real time effect presenter module 3432, side effect indicator module 3434, algorithm utilizer module 3436, indicator module 3442, matching algorithm utilizer module 3444, determiner module 3446, output device presenter module 3448, and/or third party presenter module 3454. Algorithm utilizer module 3436 may include comparison algorithm utilizer module 3438 and/or contraindication utilizer module 3440. Output device presenter module 3448 may include user interface presenter module 3450 and/or mobile device presenter module 3452. Third party presenter module 3454 may include health care provider presenter module 3456 and/or selective presenter module 3458.

System 3200 generally represents instrumentality for accepting an indication of an individual's compliance with an artificial sensory experience and/or presenting an indication of a bioactive agent at least partly based on the indication of the individual's compliance with the artificial sensory experience. The operations of accepting an indication of an individual's compliance with an artificial sensory experience and/or presenting an indication of a bioactive agent at least partly based on the indication of the individual's compliance with the artificial sensory experience may be accomplished electronically, such as with a set of interconnected electrical components, an integrated circuit, and/or a computer processor.

Figure 36:
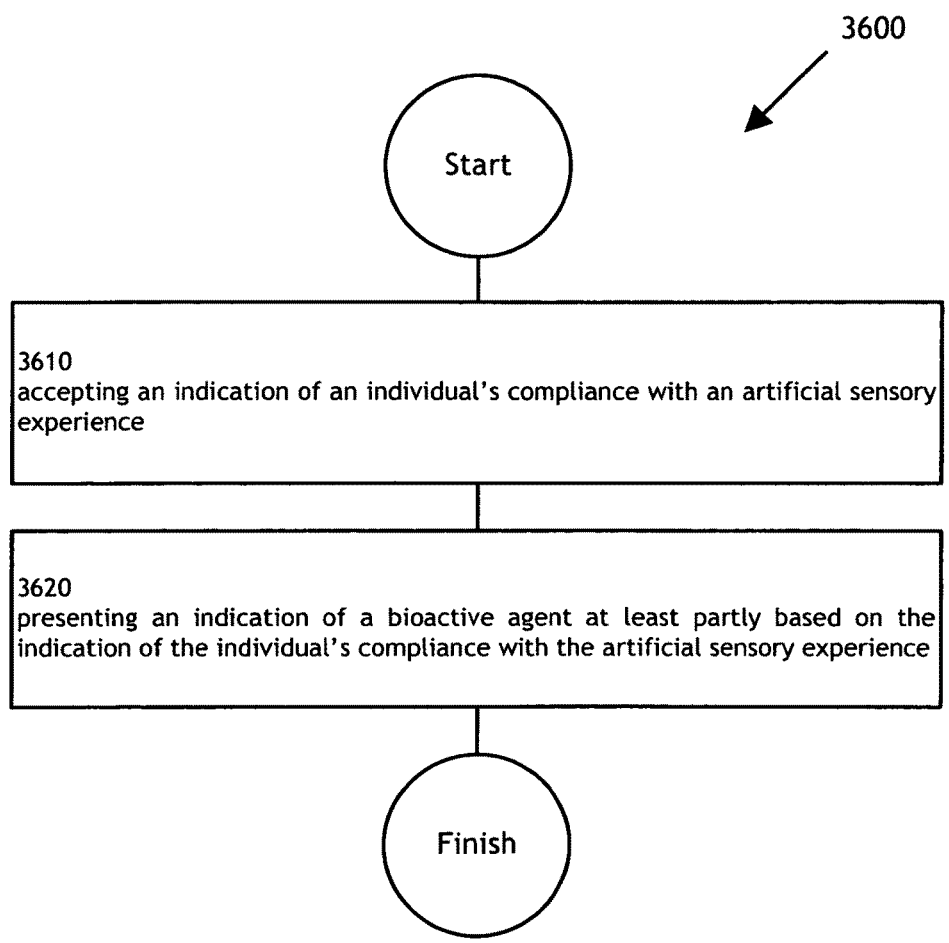
FIG. 36 illustrates an operational flow representing example operations related to presenting a combination treatment.

FIG. 36 illustrates an operational flow 3600 representing example operations related to accepting an indication of an individual's compliance with an artificial sensory experience and/or presenting an indication of a bioactive agent at least partly based on the indication of the individual's compliance with the artificial sensory experience. In FIG. 36 and in following figures that include various examples of operational flows, discussion and explanation may be provided with respect to the above-described examples of FIGS. 32 through 35, and/or with respect to other examples and contexts. However, it should be understood that the operational flows may be executed in a number of other environments and contexts, and/or in modified versions of FIGS. 32 through 35. Also, although the various operational flows are presented in the sequence(s) illustrated, it should be understood that the various operations may be performed in other orders than those which are illustrated, or may be performed concurrently.

After a start operation, operational flow 3600 moves to an operation 3610. Operation 3610 depicts accepting an indication of an individual's compliance with an artificial sensory experience. For example, as shown in FIGS. 32 through 35, accepter module 3402 may accept an indication of an individual's compliance with an artificial sensory experience. In one embodiment, accepter module 3402 may accept a computer usage tog for a virtual world account for an individual. In this embodiment, the virtual world may be a prescribed artificial sensory experience for the individual where a computer tog may indicate an individual's usage of the virtual world and further indicate compliance with the prescription artificial sensory experience. In some instances, accepter module 3402 may include a computer processor.

Then, operation 3620 depicts presenting an indication of a bioactive agent at least partly based on the indication of the individual's compliance with the artificial sensory experience. For example, as shown in FIGS. 32 through 35, presenter module 3428 may present an indication of a bioactive agent based on the indication of the individual's compliance with the artificial sensory experience, such as a prescribed artificial sensory experience. In one example, presenter module 3428 may present an indication of an antianxiety medication, such as Xanax, based on an indication of an RFID tag configured to indicate compliance with a physician's prescription for a virtual world. In some instances, presenter module 3428 may include a computer processor.

Figure 37:
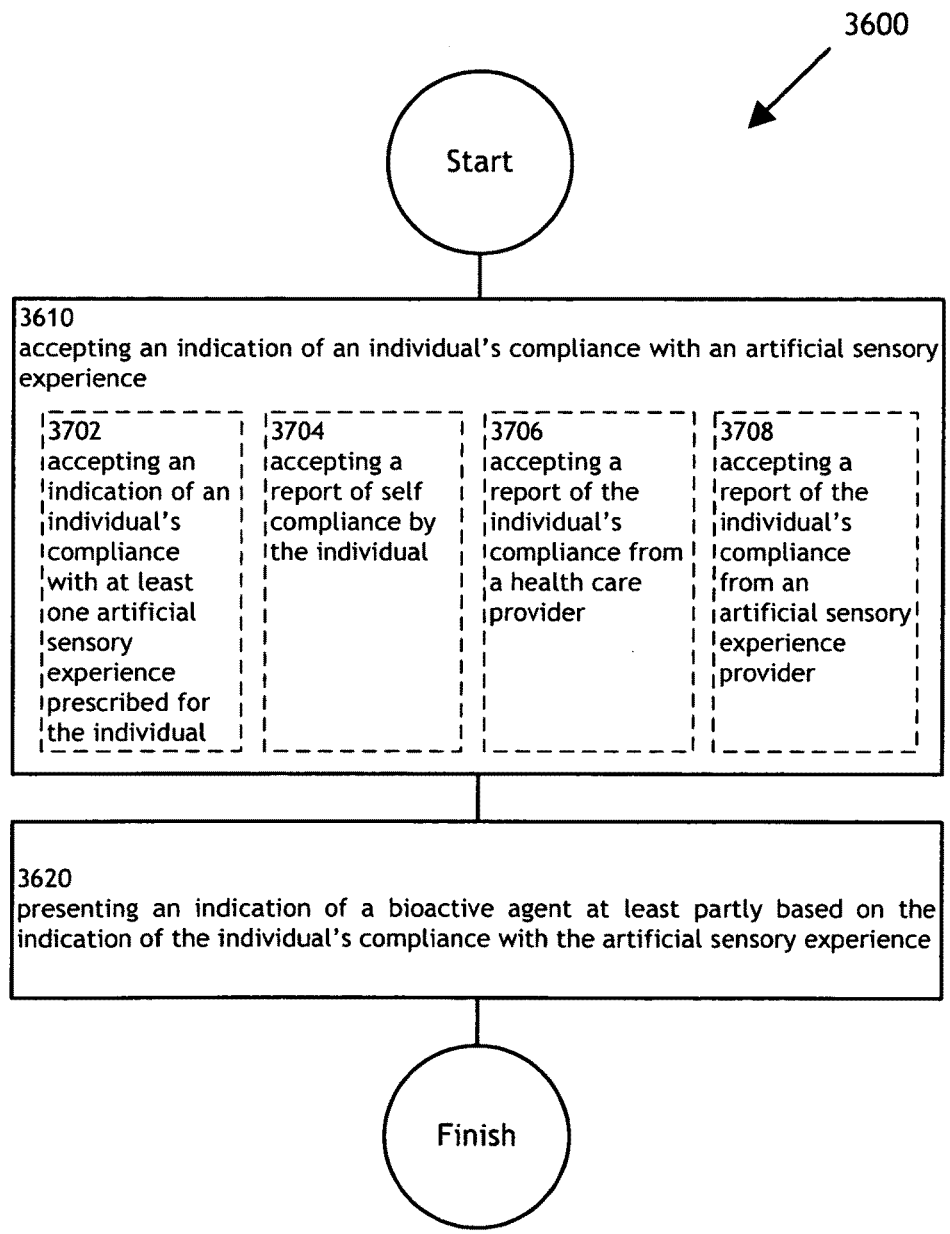
FIG. 37 illustrates an alternative embodiment of the operational flow of FIG. 36.

FIG. 37 illustrates alternative embodiments of the example operational flow 3600 of FIG. 36. FIG. 37 illustrates example embodiments where operation 3610 may include at least one additional operation. Additional operations may include an operation 3702, operation 3704, operation 3706, and/or operation 3708.

Operation 3702 illustrates accepting an indication of an individual's compliance with at least one artificial sensory experience prescribed for the individual. For example, as shown in FIGS. 32 through 35, prescribed artificial sensory experience accepter module 3404 may accept an indication of an individual's compliance with at least one artificial sensory experience prescribed for the individual. In one embodiment, prescription artificial sensory experience accepter module 3404 may accept an indication of an individual's compliance with a virtual world prescribed for the individual. A prescribed artificial sensory experience may include a prescription from a health care provider, such as a physician, a psychiatrist, and/or a nurse practitioner. In some instances, prescription artificial sensory experience accepter module 3404 may include a computer processor.

Operation 3704 illustrates accepting a report of self compliance by the individual. For example, as shown in FIGS. 32 through 35, self report accepter module 3406 may accept a self compliance report from an individual. In one embodiment, self report accepter module 3406 may accept a report from individual of compliance with a prescribed virtual experience, such as a virtual world. In this embodiment, the individual may report compliance, for example, by inputting an indication of compliance into a program. Other examples of self compliance reporting may include entering an indication of compliance on a website, and/or using a telephone prompt system to enter an indication of compliance at a remote location. One additional example of self reporting may be found in Cafer, U.S. Patent Publication No. 2008/0243544, which is incorporated herein by reference. In some instances, self report accepter module 3406 may include a computer processor.

Operation 3706 illustrates accepting a report of the individual's compliance from a health care provider. For example, as shown in FIGS. 32 through 35, health care provider report accepter module 3408 may accept a report of the individual's compliance from a health care provider. In one embodiment, health care provider report accepter module 3408 may accept a report from an individual's psychiatrist of the individual's compliance with a prescription for an online tutorial. In this embodiment, the health care provider may report compliance, for example, by inputting an indication of compliance into a program. Other examples of health care provider reporting of an individual's compliance may include entering an indication of compliance on a website, and/or using a telephone prompt system to enter an indication of compliance at a remote location. In some instances, health care provider report accepter module 3408 may include a computer processor.

Operation 3708 illustrates accepting a report of the individual's compliance from an artificial sensory experience provider. For example, as shown in FIGS. 32 through 35, artificial sensory experience provider report accepter module 3410 may accept a report of the individual's compliance from an artificial sensory experience provider. In one embodiment, artificial sensory experience provider report accepter module 3410 may accept a report of an individual's compliance from a software company, such as Blizzard Entertainment. In this embodiment, the software company may mine compliance data from an individual's activity in an artificial sensory experience, such as World of Warcraft, created by the software company and send the information to artificial sensory experience provider report accepter module 3410. In some instances, artificial sensory experience provider report accepter module 3410 may include a computer processor and/or instrumentation configured to receive data, such as a data modem.

Figure 38:
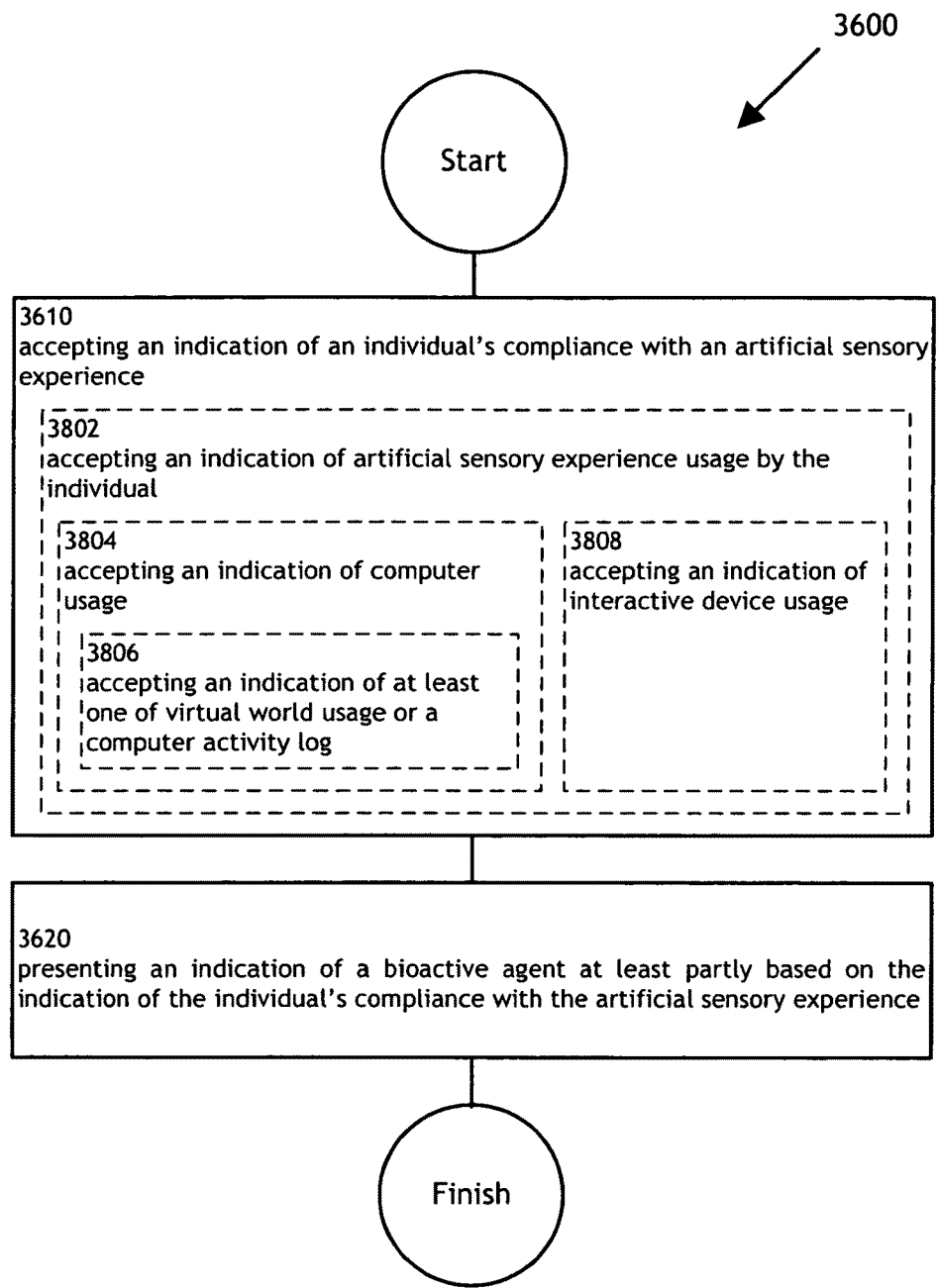
FIG. 38 illustrates an alternative embodiment of the operational flow of FIG. 36.

FIG. 38 illustrates alternative embodiments of the example operational flow 3600 of FIG. 36. FIG. 38 illustrates example embodiments where operation 3610 may include at least one additional operation. Additional operations may include operation 3802, operation 3804, operation 3806, and/or operation 3808.

Operation 3802 illustrates accepting an indication of artificial sensory experience usage by the individual. For example, as shown in FIGS. 32 through 35, artificial sensory experience usage accepter module 3412 may accept an indication of artificial sensory experience usage by the individual. In one embodiment, artificial sensory experience usage accepter module 3412 may accept an indication of usage of a virtual world, such as World of Warcraft, by the individual. One example of artificial sensory experience usage may include an amount of time the individual is engaged in the artificial sensory experience. Another example of measuring artificial sensory experience usage may include accepting a certain score, where each score may be correlated with progress in the artificial sensory by the individual. Further discussion regarding accepting an indication of artificial sensory usage and feedback may be found in Jung et al., U.S. Patent Publication No. 2007/0112624, which is incorporated herein by reference. In some instances, artificial sensory experience usage accepter module 3412 may include a computer processor.

Further, operation 3804 illustrates accepting an indication of computer usage. For example, as shown in FIGS. 32 through 35, computer usage accepter module 3414 may accept an indication of computer usage. In one embodiment, computer usage accepter module 3414 may accept an indication of a computer's usage by accessing a certain individual's account log. In another example, computer usage accepter module 3414 may accept user interaction with a computer generated virtual reality environment, further discussed in Elkind, U.S. Pat. No. 6,149,586, which is incorporated herein by reference. In some instances, computer usage accepter module 3414 may include a computer processor.

Further, operation 3806 illustrates accepting an indication of at least one of virtual world usage or a computer activity log. For example, as shown in FIGS. 32 through 35, virtual world usage accepter module 3416 may accept an indication of at least one of virtual world usage and/or a computer activity log. An indication of virtual world usage may include a report, such as a self report and/or a computer generated report showing, for example, an amount of time spent by an individual complying with an artificial sensory experience prescription. A computer activity log may include any practice where sequential data may be recorded. Some examples of a computer activity log may include a web counter, a server log, and/or using logging related software, such as Multitail and/or Pantheios. In one embodiment, virtual world usage accepter module 3416 may accept a computer activity log from a computer program, such as Pantheios, indicating usage by a specific individual. In some instances, virtual world usage accepter module 3416 may include a computer processor.

Further, operation 3808 illustrates accepting an indication of interactive device usage. For example, as shown in FIGS. 32 through 35, interactive device usage accepter module 3418 may accept an indication of usage of an interactive device. Some examples of an interactive device may include a user interface, an interactive whiteboard, a flight simulator, and/or a wired glove. In one embodiment, interactive device usage accepter module 3418 may accept an indication of usage of a virtual world coupled with a wired glove. Other examples of an interactive device may include a virtual reality exercise machine and a hand-held computer interactive device respectively found in Jarvik, U.S. Pat. No. 5,577,981, and Daniel, U.S. Pat. No. 7,161,579, each of which is incorporated herein by reference. In some instances, interactive device usage accepter module 3418 may include a computer processor.

Figure 39:
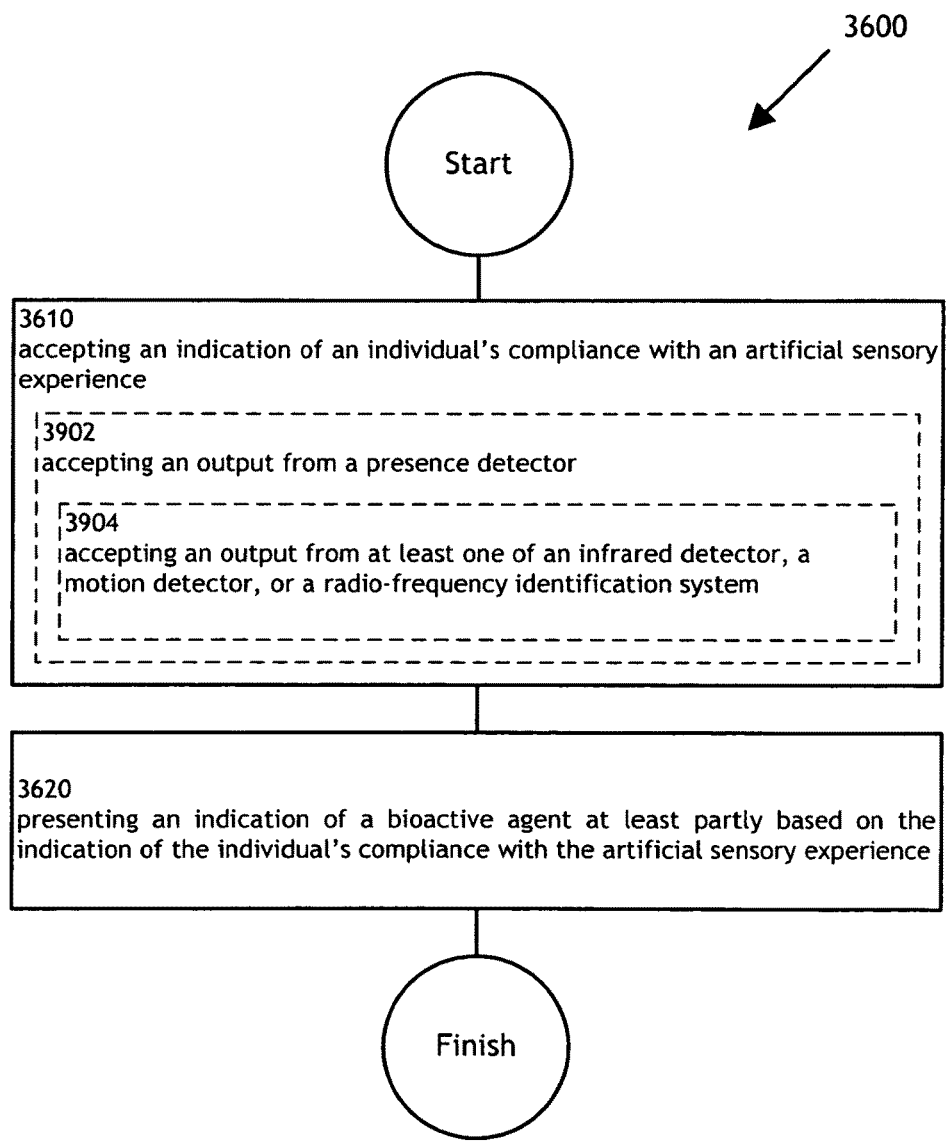
FIG. 39 illustrates an alternative embodiment of the operational flow of FIG. 36.

FIG. 39 illustrates alternative embodiments of the example operational flow 3600 of FIG. 36. FIG. 39 illustrates example embodiments where operation 3610 may include at least one additional operation. Additional operations may include operation 3902, and/or operation 3904.

Operation 3902 illustrates accepting an output from a presence detector. For example, as shown in FIGS. 32 through 35, presence detector output accepter module 3420 may accept an output from a presence detector. In one embodiment, presence detector output accepter module 3420 may accept an output from a motion detector. Accepting an output may include, for example, accepting a signal, such as an electrical and/or optical signal. A presence detector may include a device configured for detection of an individual, for example using sound, heat, and/or motion. Some examples of a presence detector may include a safety laser scanner, available from OMRON Corporation, Kyoto, Japan, and/or a speech presence detector, such as discussed in Taylor et al., U.S. Pat. No. 5,822,726, which is incorporated herein by reference. Another example of a presence detector may include a camera coupled to a motion sensor, such as the VIR-101 infrared motion detector w/camera available from Security Labs®, Noblesville, Ind. Other example of a presence detector may include a pressure sensor and/or a microphone. In some instances, presence detector output accepter module 3420 may include a computer processor.

Further, operation 3904 illustrates accepting an output from at least one of an infrared detector, a motion detector, or a radio-frequency identification system. For example, as shown in FIGS. 32 through 35, presence detector output accepter module 3420 may accept an output from a radio-frequency identification (RFID) tag. A radio frequency identification system may include a system utilizing radio frequency signals to identify an object or a person, such as in the case of using an RFID tag. A RFID tag may include on object which may be applied to or included in an object, where the RFID tag utilizes radio waves for the purpose of identification. A RFID tag may include an integrated circuit for storing and/or processing information along with an antenna for receiving and transmitting a signal. In one embodiment, presence detector output accepter module 3420 may accept an output from a RFID tag on an individual's person, where the RFID tag may have a limited range for signal transmission/reception. In this embodiment, proximity of the RFID tag to presence detector output accepter module 3420 combined with the limited signal transmission/reception range may indicate a likelihood that an individual may be engaged in an artificial sensory experience, such as logging on to a virtual world. In another embodiment, presence detector output accepter module 3420 may accept an output from an infrared detector that is placed proximate to a computer where an individual engages in a prescribed artificial sensory experience. In this embodiment, the infrared detector may detect the individual, for example by infrared light radiating from the individual, while engaging in the prescribed artificial sensory experience. Additionally, presence detector output accepter module 3420 may be coupled to, for example, a logging and/or recording device for recording the amount of time and/or whether the individual complied with a prescription for an artificial sensory experience. In some instances, presence detector output accepter module 3420 may include a computer processor and/or instrumentation, such as a passive infrared sensor. One example of a passive infrared sensor may be found in Owers, U.S. Pat. No. 4,734,585, which is incorporated herein by reference.

Figure 40:
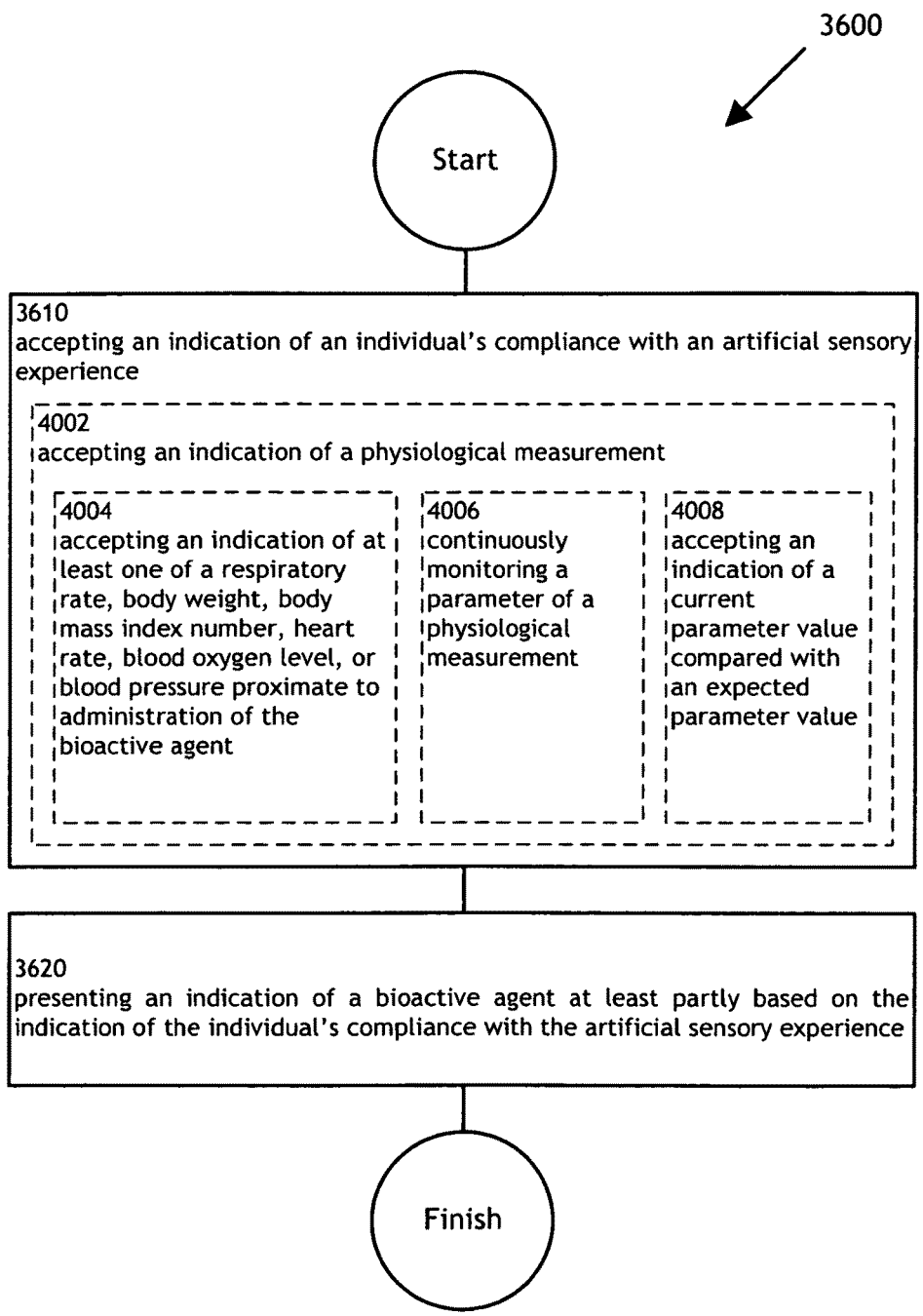
FIG. 40 illustrates an alternative embodiment of the operational flow of FIG. 36.

FIG. 40 illustrates alternative embodiments of the example operational flow 3600 of FIG. 36. FIG. 40 illustrates example embodiments where operation 3610 may include at least one additional operation. Additional operations may include operation 4002, operation 4004, operation 4006, and/or operation 4008.

Operation 4002 illustrates accepting an indication of a physiological measurement. For example, as shown in FIGS. 32 through 35, physiological measurement accepter module 3422 may accept an indication of a physiological measurement. In one embodiment, physiological measurement accepter module 3422 may accept an indication of a heart rate from a physiological measurement device, such as the device discussed in Chang, U.S. Patent Publication No. 2007/0123783, which is incorporated herein by reference. A physiological measurement may include a measurement of the mechanical, physical, and/or biochemical functions of the body. Some examples of a physiological measurement may include body weight, blood pressure, heart rate, blood oxygen level, and/or body temperature. In some instances, physiological measurement accepter module 3422 may include a computer processor.

Further, operation 4004 illustrates accepting an indication of at least one of a respiratory rate, body weight, body mass index number, heart rate, blood oxygen level, or blood pressure proximate to administration of the bioactive agent. For example, as shown in FIGS. 32 through 35, physiological measurement accepter module 3422 may accept an indication of at least one of a respiratory rate, body weight, body mass index number, heart rate, blood oxygen level, or blood pressure proximate to administration of the bioactive agent. In one embodiment, physiological measurement accepter module 3422 may accept an indication of a respiratory rate from a physiological measurement device. A respiratory rate may include the number of breaths taken per minute. Accepting an indication of body weight and/or a body mass index number may include accepting information from a scale and/or a computing device. In one embodiment, physiological measurement accepter module 3422 may accept a body weight of an individual experiencing a Wii Fitness game while being administered a weight loss medication by using a scale 3220 coupled with a computer processor. In the same embodiment, scale 3220 and a computer processor may constantly monitor the body mass index of the individual. Further, accepting an indication of a heart rate may include accepting a measurement of work done by the heart, such as a measurement of beats per unit time and/or a pulse. Accepting an indication of a blood oxygen level may include accepting a measurement from a pulse oximeter and/or a measurement of oxygen saturation directly through a blood sample. Accepting an indication of blood pressure may include accepting a measurement of blood pressure from, for example, a sphygmomanometer, which may be coupled to a computer processor or other monitoring device. Additionally, physiological measurement accepter module 3422 may accept a physiological measurement before, during, and/or after an artificial sensory experience and/or bioactive agent administration. In some instances, physiological measurement accepter module 3422 may include a computer processor and/or other medical instrumentation, such as that discussed herein.

Further, operation 4006 illustrates continuously monitoring a parameter of a physiological measurement. For example, as shown in FIGS. 32 through 35, parameter monitorer module 3424 may continuously monitor a parameter of a physiological measurement. In one embodiment, parameter monitorer module 3424 may continuously and remotely monitor perspiration data for an individual. Continuous monitoring may include measuring a specified parameter without interruption and/or delay. One example of a system configured for continuously and/or remotely monitoring a medical parameter may be found in Rode et al., U.S. Pat. No. 6,315,719, which is incorporated herein by reference. In some instances, parameter monitorer module 3424 may include a computer processor and/or medical instrumentation, such as that described herein.

Further, operation 4008 illustrates accepting an indication of a current parameter value compared with an expected parameter value. For example, as shown in FIGS. 32 through 35, compared value accepter module 3426 may accept an indication of a current parameter value compared with an expected parameter value. In one embodiment, compared value accepter module 3426 may accept an indication of a current blood pressure measurement compared with an expected blood pressure value. By comparing a current parameter with an expected value, efficacy of an artificial sensory experience and/or a bioactive may be determined. For example, if a current blood pressure measurement is higher than an expected blood pressure value, a health care provider may determine that an artificial sensory experience and/or bioactive agent is not efficacious and may prescribe an alternative artificial sensory experience and/or bioactive agent. In some instances, compared value accepter module 3426 may include a computer processor.

Figure 41:
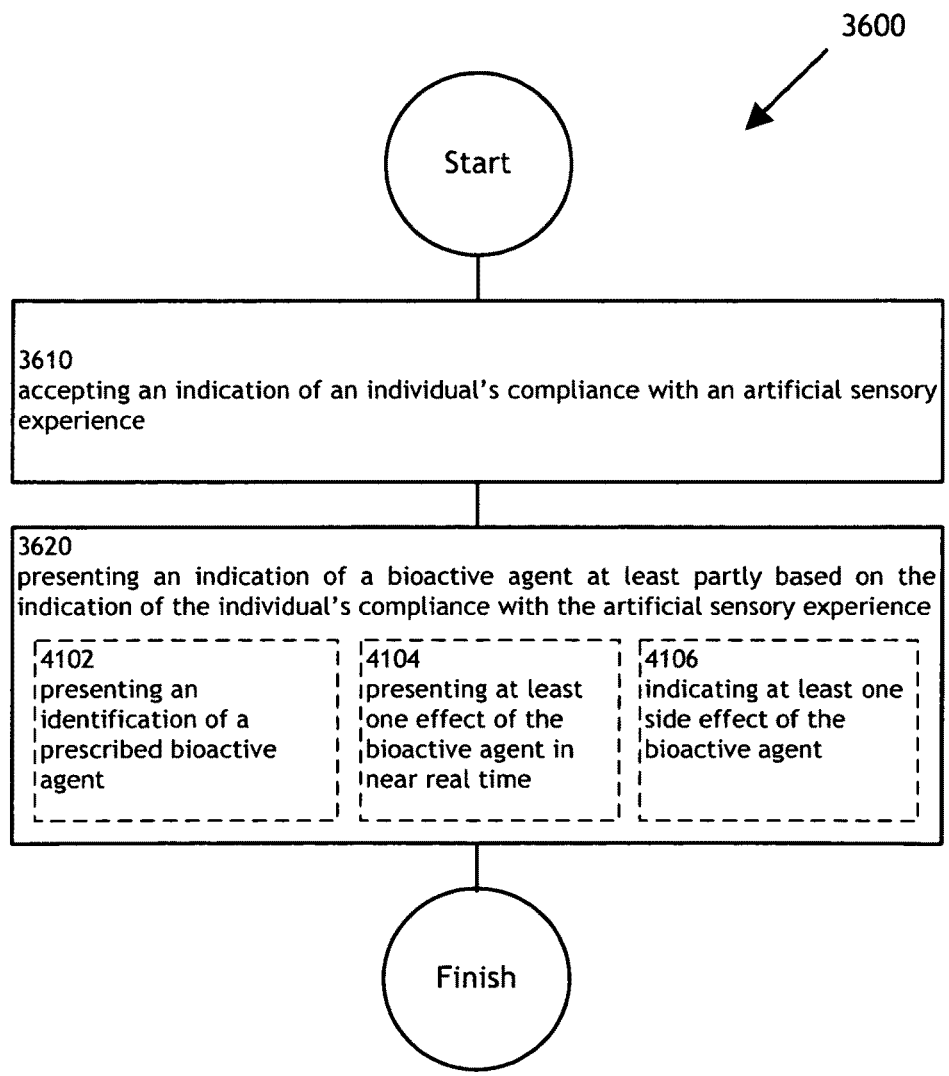
FIG. 41 illustrates an alternative embodiment of the operational flow of FIG. 36.

FIG. 41 illustrates alternative embodiments of the example operational flow 3600 of FIG. 36. FIG. 41 illustrates example embodiments where operation 3620 may include at least one additional operation. Additional operations may include operation 4102, operation 4104, and/or operation 4106.

Operation 4102 illustrates presenting an identification of a prescribed bioactive agent. For example, as shown in FIGS. 32 through 35, prescription bioactive agent presenter module 3430 may present an identification of a prescribed bioactive agent. In one embodiment, prescription bioactive agent presenter module 3430 may present an identification of a prescribed bioactive agent to a pharmacy. Additionally, prescribed bioactive agent presenter module 3430 may present to other entities, such as a hospital, a physician, a nurse, and/or an insurance company. An additional example of presenting bioactive agent information may be found in Mayaud, U.S. Publication No. 2003/01444884, which is incorporated herein by reference. In some instances, prescription bioactive agent presenter module 3430 may include a computer processor.

Operation 4104 illustrates presenting at least one effect of the bioactive agent in near real time. For example, as shown in FIGS. 32 through 35, near real time effect presenter module 3432 may present at least one effect of the bioactive agent in near real time. A near real time event may include the current time of an event plus processing time. In one embodiment, near real time effect presenter module 3432 may present in near real time an effect of an antianxiety medication on an individual's perspiration rate to a supervising physician. A further example of presenting in real time and/or near real time, including real-time medical alerting, may be found in McGovern, U.S. Pat. No. 6,909,359, which is incorporated herein by reference. In some instances, near real time effect presenter module 3432 may include a computer processor.

Operation 4106 illustrates indicating at least one side effect of the bioactive agent. For example, as shown in FIGS. 32 through 35, side effect indicator module 3434 may indicate at least one side effect of the bioactive agent. In one embodiment, side effect indicator module 3434 may indicate a drop in heart rate caused by an anti anxiety medication. Some examples of side effects may include fever, hypertension, and/or headache, as well as other side effects known in medicine. In some instances, side effect indicator module 3434 may include a computer processor.

Figure 42:
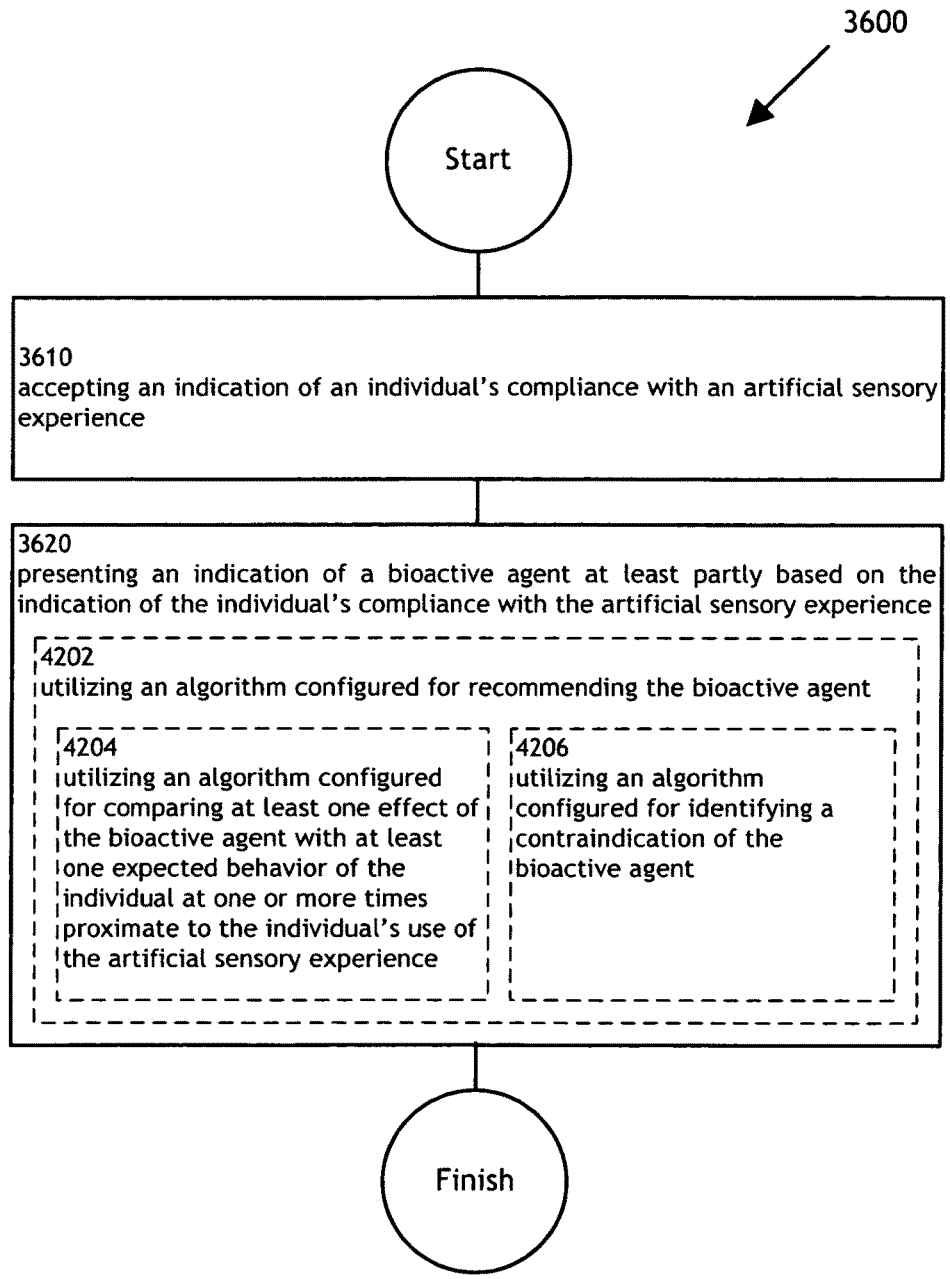
FIG. 42 illustrates an alternative embodiment of the operational flow of FIG. 36.

FIG. 42 illustrates alternative embodiments of the example operational flow 3600 of FIG. 36. FIG. 42 illustrates example embodiments where operation 3620 may include at least one additional operation. Additional operations may include an operation 4202, operation 4204, and/or operation 4206.

Operation 4202 illustrates utilizing an algorithm configured for recommending the bioactive agent. For example, as shown in FIGS. 32 through 35, algorithm utilizer module 3436 may utilize an algorithm configured for recommending the bioactive agent. An algorithm configured for recommending the bioactive agent may include any computation, formula, statistical survey, and/or look-up table for determining and/or selecting a suitable prescription medication combination. Some examples may include a computer software algorithm, a calculator, a flowchart, and/or a decision tree. In one embodiment, algorithm utilizer module 3436 may utilize an algorithm that uses an inputted artificial sensory experience and compares the artificial sensory experience with information in a clinical trial database for determining bioactive agent compatability. In some instances, algorithm utilizer module 3436 may include a computer processor.

Further, operation 4204 illustrates utilizing an algorithm configured for comparing at least one effect of the bioactive agent with at least one expected behavior of the individual at one or more times proximate to the individual's use of the artificial sensory experience. For example, as shown in FIGS. 32 through 35, comparison algorithm utilizer module 3438 may utilize an algorithm configured for comparing at least one effect of the bioactive agent with at least one expected behavior of the individual at one or more times proximate to the individual's use of the artificial sensory experience. In one embodiment, comparison algorithm utilizer module 3438 may utilize a comparison algorithm configured for comparing an antianxiety medication with a heart rate measurement proximate to an artificial sensory experience configured for reducing a phobia, such as a fear of heights. Such a comparison may indicate a need to modify and/or efficacy of a prescribed artificial sensory experience and/or bioactive agent. In some instances, comparison algorithm utilizer module 3438 may include a computer processor.

Further, operation 4206 illustrates utilizing an algorithm configured for identifying a contraindication of the bioactive agent. For example, as shown in FIGS. 32 through 35, contraindication utilizer module 3440 may utilize an algorithm configured for identifying a contraindication of the bioactive agent. A contraindication of a bioactive agent may include giving an indication against the advisability of the bioactive agent. For example, contraindication utilizer module 3440 may utilize an algorithm that considers an individual's personal medical history and may recommend not prescribing a certain medication. Contraindication utilizer module 3440 may identify a contraindication of a bioactive agent for reasons such as an adverse reaction and/or inefficacy. In some instances, contraindication utilizer module 3440 may include a computer processor.

Figure 43:
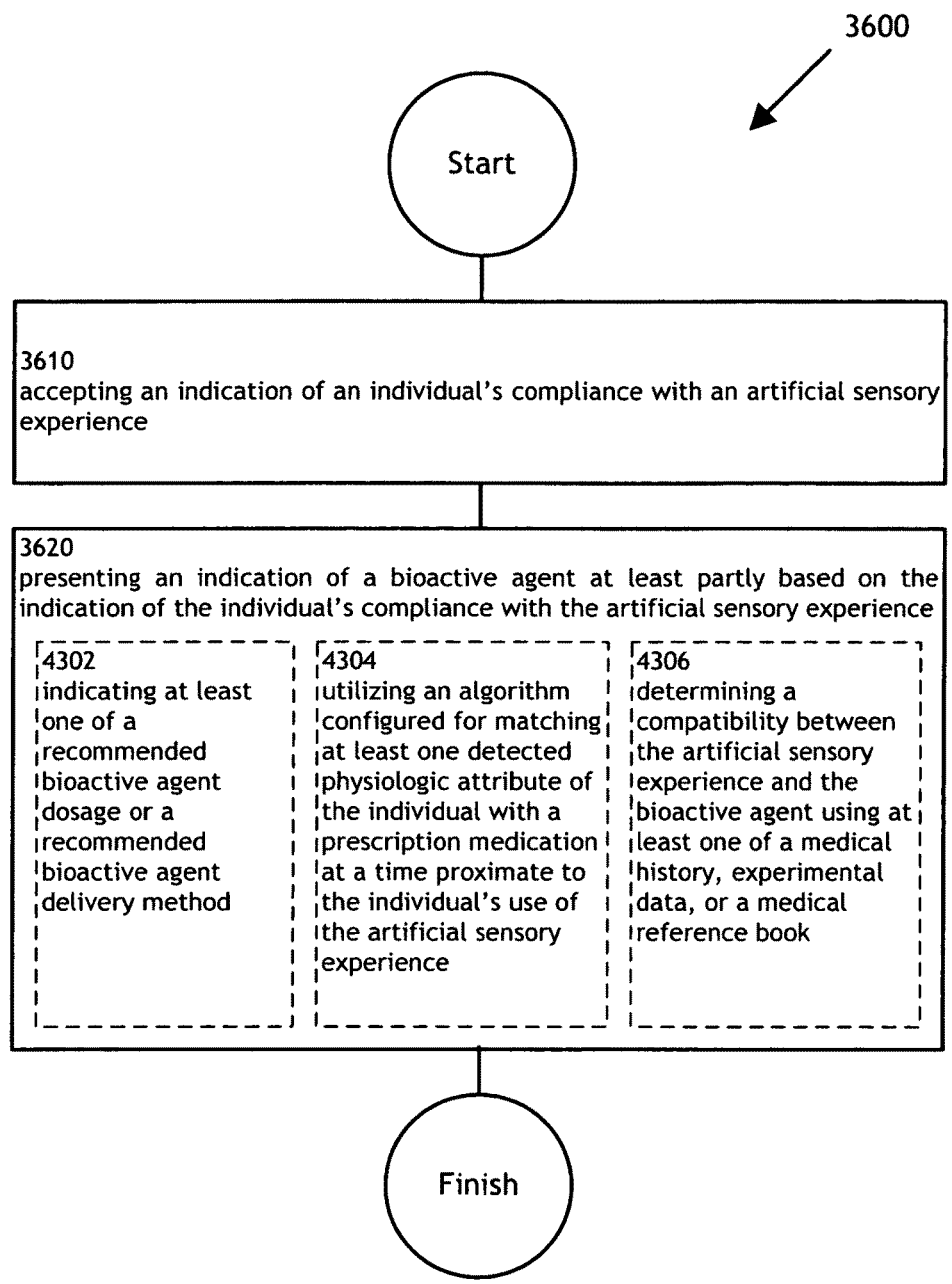
FIG. 43 illustrates an alternative embodiment of the operational flow of FIG. 36.

FIG. 43 illustrates alternative embodiments of the example operational flow 3600 of FIG. 36. FIG. 43 illustrates example embodiments where operation 3620 may include at least one additional operation. Additional operations may include operation 4302, operation 4304, and/or operation 4306.

Operation 4302 illustrates indicating at least one of a recommended bioactive agent dosage or a recommended bioactive agent delivery method. For example, as shown in FIGS. 32 through 35, indicator module 3442 may indicate at least one of a recommended bioactive agent dosage or a recommended bioactive agent delivery method. In one embodiment, indicator module 3442 may indicate a recommended bioactive dosage, such as a dosage reduction for an opioid. Indicator module 3442 may recommend an initial dosage and may also recommend a change in dosage, such as an increased or reduced dosage. One example of reducing a bioactive agent dosage using a controller in an implanted device may be found in Shelton, U.S. Patent Publication No. 2008/0172044, which is incorporated herein by reference. Some examples of bioactive delivery methods may include mucosal administration, parenteral administration (such as intravenous, intramuscular, and/or subcutaneous administration), topical administration such as epicutaneous administration, inhalational administration, transdermal administration, and/or enteral therapy, such as a pill taken orally, or the Like. In one instance, indicator module 3442 may include a computer processor.

Operation 4304 illustrates utilizing an algorithm configured for matching at least one detected physiologic attribute of the individual with a prescription medication at a time proximate to the individual's use of the artificial sensory experience. For example, as shown in FIGS. 32 through 35, matching algorithm utilizer module 3444 may utilize an algorithm configured for matching at least one detected physiologic attribute of the individual with a prescription medication at a time proximate to the individual's use of the artificial sensory experience. In one embodiment, matching algorithm utilizer module 3444 may use an algorithm configured for matching a detected physiologic attribute, such as blood pressure, with an antianxiety medication at a time proximate to an artificial sensory experience, such as a virtual world configured to reduce a fear of flying. The use of such an algorithm may serve to increase efficacy and compatability of an artificial sensory experience and/or a bioactive agent. By matching a physiologic attribute with a prescription medication proximate in time to an artificial sensory experience, a health care provider may more effectively prescribe a medication because the health care provider can determine that the artificial sensory experience may be the cause of the physiologic attribute. In some instances, matching algorithm utilizer module 3444 may include a computer processor.

Operation 4306 illustrates determining a compatibility between the artificial sensory experience and the bioactive agent using at least one of a medical history, experimental data, or a medical reference book. For example, as shown in FIGS. 32 through 35, determiner module 3446 may determine a compatibility between the artificial sensory experience and the bioactive agent using at least one of a medical history, experimental data, or a medical reference book. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. Experimental data may include any data from an experiment, such as a clinical trial. The experiment may be an experiment including an individual and/or a group of people. Some examples of a medical reference book may include a medical dictionary, a medical journal, and/or a book of drug interactions. In one embodiment, determiner module 3446 may determine a compatability of an antianxiety medication and a virtual world designed to overcome a phobia. In this embodiment, determiner module 3446 may use, for example, experimental and empirical data including clinical trial results from a group of people previously having used the same combination antianxiety medication and virtual world designed to overcome a phobia. In another embodiment, determiner module 3446 may determine a compatability using an individual's personal medical history including previous artificial sensory experience and bioactive agent interactions. In some instances, determiner module 3446 may include a computer processor.

Figure 44:
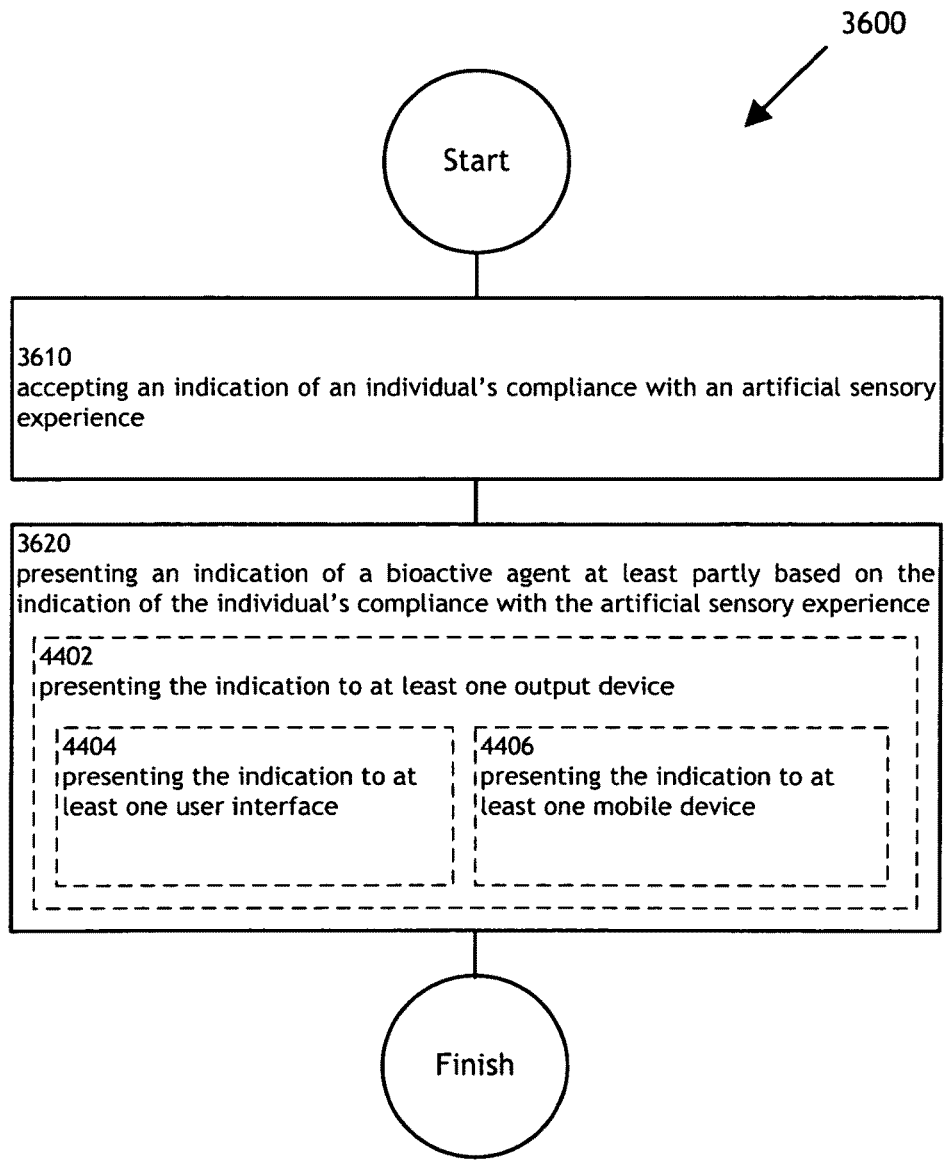
FIG. 44 illustrates an alternative embodiment of the operational flow of FIG. 36.

FIG. 44 illustrates alternative embodiments of the example operational flow 3600 of FIG. 36. FIG. 44 illustrates example embodiments where operation 3620 may include at least one additional operation. Additional operations may include operation 4402, operation 4404, and/or operation 4406.

Operation 4402 illustrates presenting the indication to at least one output device. For example, as shown in FIGS. 32 through 35, output device presenter module 3448 may present to at least one output device. In one example, output device presenter module 3448 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 3448 may include a computer processor.

Further, operation 4404 illustrates presenting the indication to at least one user interface. For example, as shown in FIGS. 32 through 35, user interface presenter module 3450 may present to at least one user interface. In one embodiment, user interface presenter module 3450 may present to a touchscreen device. A user interface may include means by which an individual may interact with a system. Some examples of a user interface may include a touchscreen, a graphical user interface, a tactile interface, and/or a live user interface. In some instances, user interface presenter module 3450 may include a computer processor.

Further, operation 4406 illustrates presenting the indication to at least one mobile device. For example, as shown in FIGS. 32 through 35, mobile device presenter module 3452 may present to at least one mobile device. In one embodiment, mobile device presenter module 3452 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 3452 may include a computer processor.

Figure 45:
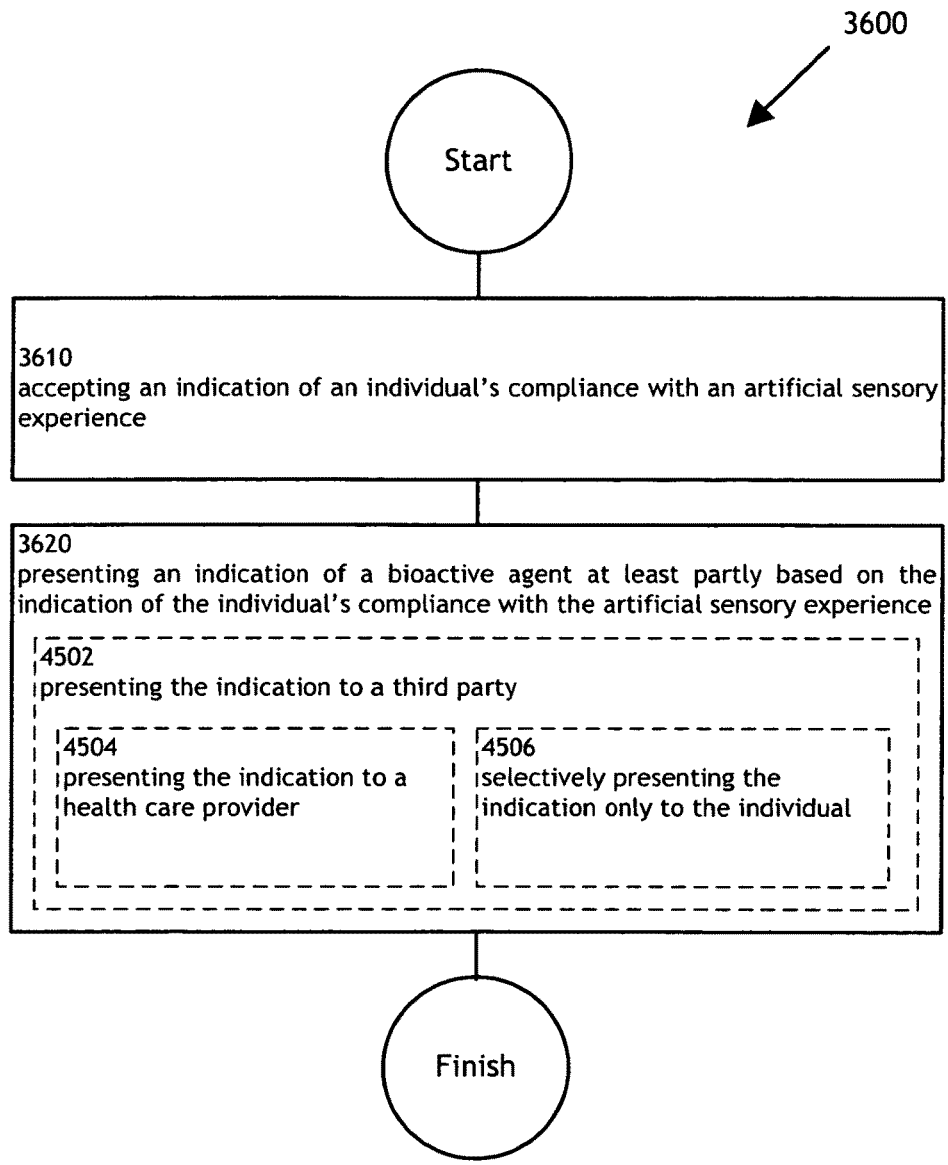
FIG. 45 illustrates an alternative embodiment of the operational flow of FIG. 36.

FIG. 45 illustrates alternative embodiments of the example operational flow 3600 of FIG. 36. FIG. 45 illustrates example embodiments where operation 3620 may include at least one additional operation. Additional operations may include operation 4502, operation 4504, and/or operation 4506.

Operation 4502 illustrates presenting the indication to a third party. For example, as shown in FIGS. 32 through 35, third party presenter module 3454 may present to a third party. For example, third party presenter module 3454 may present to an individual's physician. A third party may include a party that is an independent party, person, and/or entity. Some examples of a third party may include a physician, a medical database, a hospital, a law enforcement agency, and/or a pharmacy. One example of reporting to a third party may include creating displays and reports for aggregating data from therapy results, further discussed in Bair et al., U.S. Pat. No. 6,067,523, which is incorporated herein by reference. In some instances, third party presenter module 3454 may include a computer processor and/or a communications device, such as a monitor and network link.

Further, operation 4504 illustrates presenting the indication to a health care provider. For example, as shown in FIGS. 32 through 35, health care provider presenter module 3456 may present to a health care provider. A health care provider may include a pharmacy, a pharmaceutical company, a medical device company, a research institution, a computer software and/or computer hardware company, a website, a nurse and/or a physician. In one embodiment, health care provider presenter module 3456 may present to a physician a prescribed combination artificial sensory experience and bioactive agent therapy via a secured website. In some instances, health care provider presenter module 3456 may include a computer processor.

Further, operation 4506 illustrates selectively presenting the indication only to the individual. For example, as shown in FIGS. 32 through 35, selective presenter module 3458 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 3458 may present only to individual 134 and may keep results of a certain combination therapy confidential. In one embodiment, an encryption key may be employed to protect selected information. In an additional example, selective presenter module 3458 may report only to a law enforcement agency and/or representative, such as a probation officer, and not to individual 134. In some instances, selective presenter module 3458 may include a computer processor.

Figure 46:
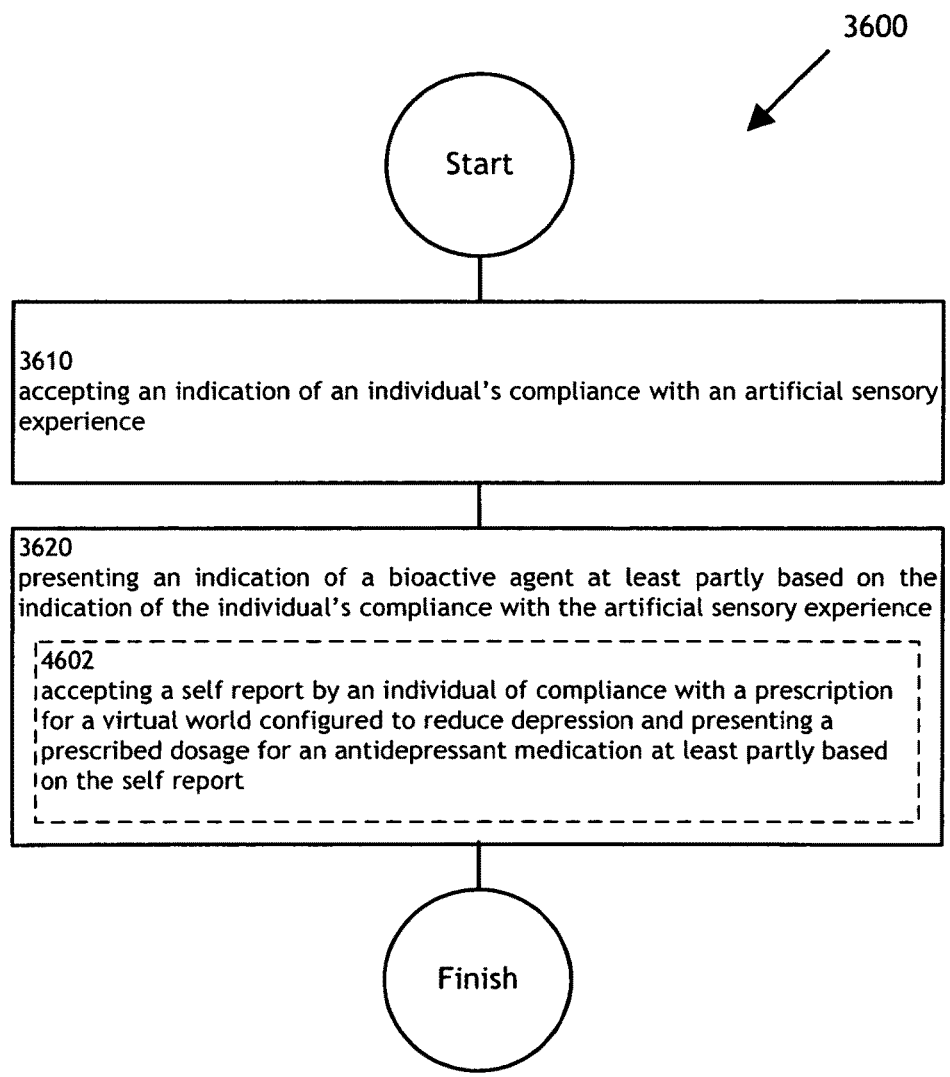
FIG. 46 illustrates an alternative embodiment of the operational flow of FIG. 36.

FIG. 46 illustrates alternative embodiments of the example operational flow 3600 of FIG. 36. FIG. 46 illustrates example embodiments where operation 3620 may include at least one additional operation. Additional operations may include operation 4602.

Operation 4602 illustrates accepting a self report by an individual of compliance with a prescription for a virtual world configured to reduce depression and presenting a prescribed dosage for an antidepressant medication at least partly based on the self report. For example, as shown in FIGS. 32 through 35, accepter module 3402 and presenter module 3428 may respectively accept a self report by an individual of compliance with a prescription for a virtual world configured to reduce depression and present a prescribed dosage for an antidepressant medication at least partly based on the self report. In some instances, accepter module 3402 and/or presenter module 3428 may include a computer processor.

Figure 47:
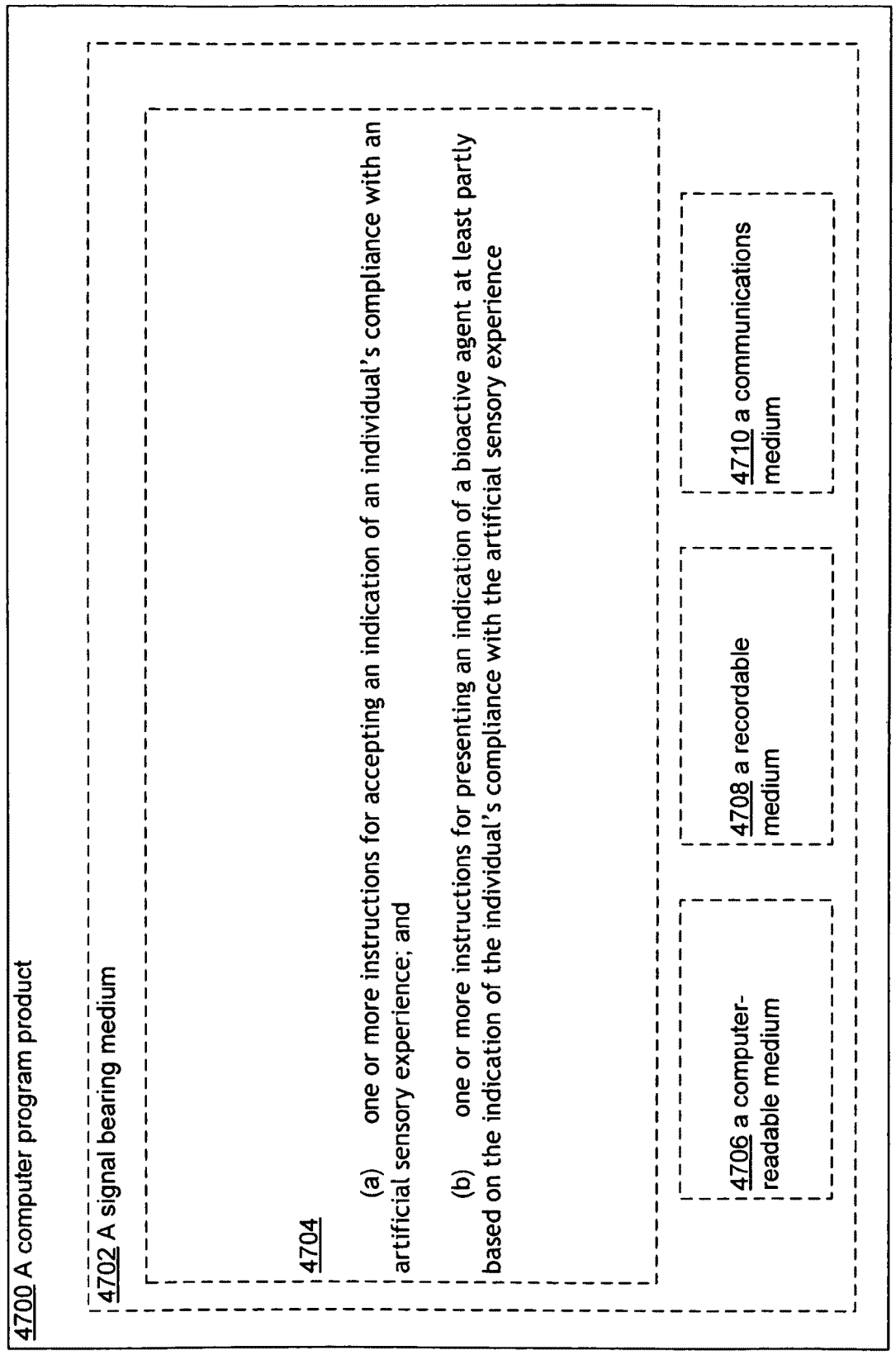
FIG. 47 illustrates a computer program product related to presenting a combination treatment.

FIG. 47 illustrates a partial view of an example computer program product 4700 that includes a computer program 4704 for executing a computer process on a computing device. An embodiment of the example computer program product 4700 is provided using a signal-bearing medium bearing 4702, and may include one or more instructions for accepting an indication of an individual's compliance with an artificial sensory experience and one or more instructions for presenting an indication of a bioactive agent at least partly based on the indication of the individual's compliance with the artificial sensory experience. The one or more instructions may be, for example, computer executable and/or logic-implemented instructions. In one implementation, the signal-bearing medium 4702 may include a computer-readable medium 4706. In one implementation, the signal bearing medium 4702 may include a recordable medium 4708. In one implementation, the signal bearing medium 4702 may include a communications medium 4710.

Figure 48:
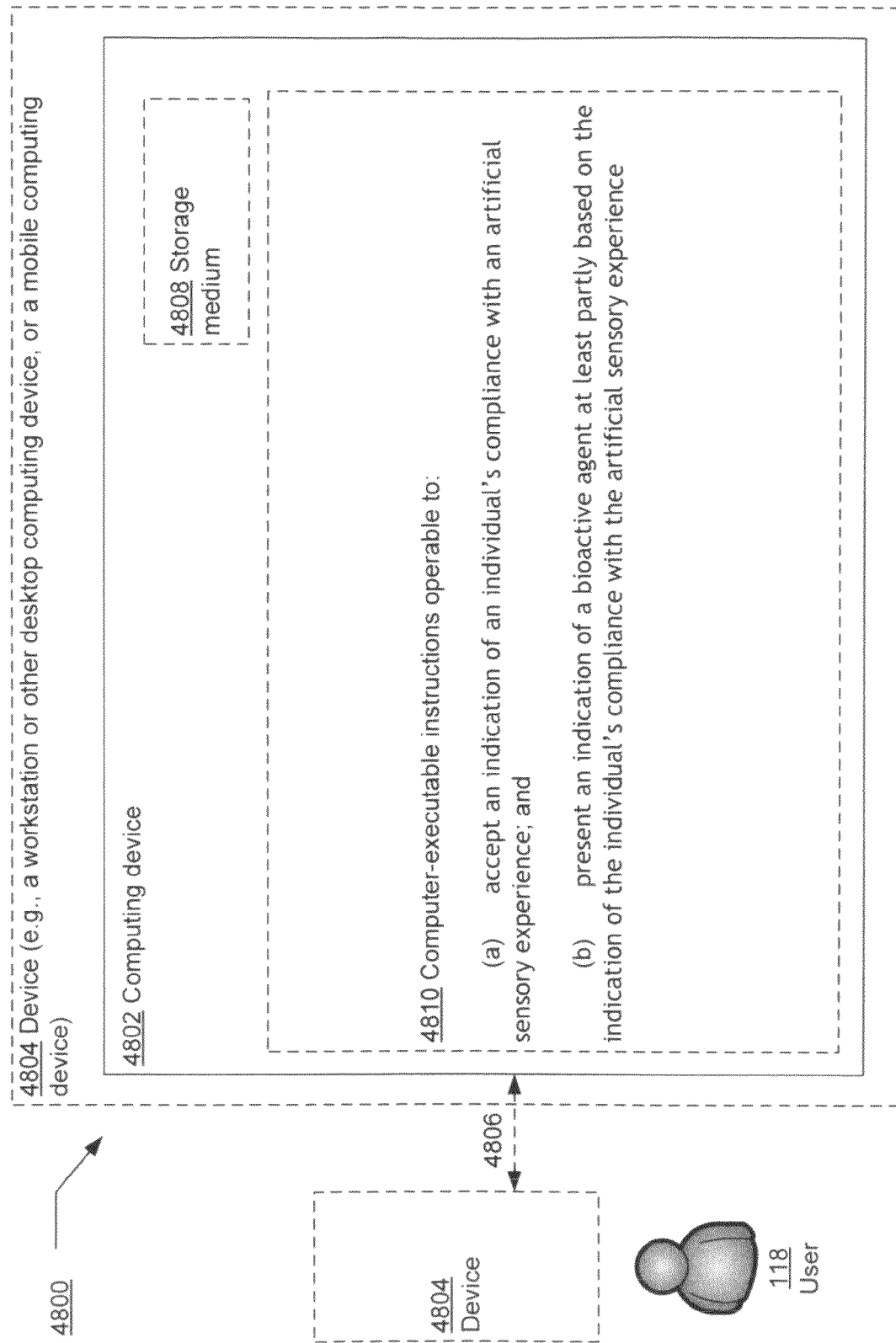
FIG. 48 illustrates a system related to presenting a combination treatment.

FIG. 48 illustrates an example system 4800 in which embodiments may be implemented. The system 4800 includes a computing system environment. The system 4800 also illustrates the user 118 using a device 4804, which is optionally shown as being in communication with a computing device 4802 by way of an optional coupling 4806. The optional coupling 4806 may represent a local, wide-area, or peer-to-peer network, or may represent a bus that is internal to a computing device (e.g., in example embodiments in which the computing device 4802 is contained in whole or in part within the device 4804). A storage medium 4808 may be any computer storage media.

The computing device 4802 includes computer-executable instructions 4810 that when executed on the computing device 4802 cause the computing device 4802 to accept an indication of an individual's compliance with an artificial sensory experience and present an indication of a bioactive agent at least partly based on the indication of the individual's compliance with the artificial sensory experience. As referenced above and as shown in FIG. 48, in some examples, the computing device 4802 may optionally be contained in whole or in part within the device 4804.

In FIG. 48, then, the system 4800 includes at least one computing device (e.g., 4802 and/or 4804). The computer-executable instructions 4810 may be executed on one or more of the at least one computing device. For example, the computing device 4802 may implement the computer-executable instructions 4810 and output a result to (and/or receive data from) the computing device 4804. Since the computing device 4802 may be wholly or partially contained within the computing device 4804, the device 4804 also may be said to execute some or all of the computer-executable instructions

4810, in order to be caused to perform or implement, for example, various ones of the techniques described herein, or other techniques.

The device 4804 may include, for example, a portable computing device, workstation, or desktop computing device. In another example embodiment, the computing device 4802 is operable to communicate with the device 4804 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electromechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art wilt also appreciate that examples of electromechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms Like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   circuitry configured to accept an indication of usage by an individual of an artificial sensory experience; and
   circuitry configured to present an indication of a bioactive agent at least partly based on the indication of usage by the individual of the artificial sensory experience.

2. The system of claim 1, wherein the circuitry configured to accept an indication of usage by an individual of an artificial sensory experience comprises:
   circuitry configured to accept an indication of usage by an individual of a prescribed artificial sensory experience.

3. The system of claim 1, wherein the circuitry configured to accept an indication of usage by an individual of an artificial sensory experience comprises:
   circuitry configured to accept a self-report of usage by an individual of an artificial sensory experience.

4. The system of claim 1, wherein the circuitry configured to accept an indication of usage by an individual of an artificial sensory experience comprises:
   circuitry configured to accept an indication from a health care provider of usage by an individual of an artificial sensory experience.

5. The system of claim 1, wherein the circuitry configured to accept an indication of usage by an individual of an artificial sensory experience comprises:
   circuitry configured to accept a report from an artificial sensory experience provider of usage by an individual of an artificial sensory experience.

6. The system of claim 1, wherein the circuitry configured to accept an indication of usage by an individual of an artificial sensory experience comprises:
   circuitry configured to accept an indication of usage by an individual of a virtual world.

7. The system of claim 1, wherein the circuitry configured to accept an indication of usage by an individual of an artificial sensory experience comprises:
   circuitry configured to accept an indication of interaction by an individual with an artificial sensory experience.

8. The system of claim 1, wherein the circuitry configured to accept an indication of usage by an individual of an artificial sensory experience comprises:
   circuitry configured to accept an indication of presence by an individual with respect to an artificial sensory experience.

9. The system of claim 1, further comprising:
   circuitry configured to accept a physiological measurement.

10. The system of claim 1, further comprising:
    circuitry configured to monitor a parameter.

11. The system of claim 1, wherein the circuitry configured to present an indication of a bioactive agent at least partly based on the indication of usage by the individual of the artificial sensory experience comprises:
    circuitry configured to present an indication of a prescription bioactive agent at least partly based on the indication of usage by the individual of the artificial sensory experience.

12. The system of claim 1, wherein the circuitry configured to present an indication of a bioactive agent at least partly based on the indication of usage by the individual of the artificial sensory experience comprises:
    circuitry configured to present in near real-time an indication of a bioactive agent at least partly based on the indication of usage by the individual of the artificial sensory experience.

13. The system of claim 1, wherein the circuitry configured to present an indication of a bioactive agent at least partly based on the indication of usage by the individual of the artificial sensory experience comprises:
    circuitry configured to present an indication of a bioactive agent and a side effect at least partly based on the indication of usage by the individual of the artificial sensory experience.

14. The system of claim 1, wherein the circuitry configured to present an indication of a bioactive agent at least partly based on the indication of usage by the individual of the artificial sensory experience comprises:
    circuitry configured to present an indication of a bioactive agent at least partly based on an algorithm.

15. The system of claim 1, wherein the circuitry configured to present an indication of a bioactive agent at least partly based on the indication of usage by the individual of the artificial sensory experience module comprises:
    circuitry configured to present an indication of a bioactive agent at least partly based on a comparison.

16. The system of claim 1, wherein the circuitry configured to present an indication of a bioactive agent at least partly based on the indication of usage by the individual of the artificial sensory experience comprises:
    circuitry configured to present an indication of a bioactive agent at least partly based on a matching algorithm.

17. The system of claim 1, further comprising:
    circuitry configured for determining the bioactive agent.

18. The system of claim 1, further comprising:
    an output device.

19. The system of claim 1, further comprising:
    a user interface.

20. The system of claim 1, further comprising:
    a mobile device.

21. The system of claim 1, wherein the circuitry configured to present an indication of a bioactive agent at least partly based on the indication of usage by the individual of the artificial sensory experience comprises:
    circuitry configured to present to a third party an indication of a bioactive agent at least partly based on the indication of usage by the individual of the artificial sensory experience.

22. The system of claim 1, wherein the circuitry configured to present an indication of a bioactive agent at least partly based on the indication of usage by the individual of the artificial sensory experience comprises:
    circuitry configured to present to a health care provider an indication of a bioactive agent at least partly based on the indication of usage by the individual of the artificial sensory experience.

23. The system of claim 1, further comprising:
circuitry configured to compare a physiological parameter value detected during usage by the individual of the artificial sensory experience with an expected physiological parameter value.

24. The system of claim 23, further comprising:
circuitry configured to determine the bioactive agent based at least partly on the physiological parameter value detected during usage by the individual of the artificial sensory experience being other than the expected physiological parameter value.

25. The system of claim 24, wherein the circuitry configured to determine the bioactive agent based at least partly on the physiological parameter value detected during usage by the individual of the artificial sensory experience being other than the expected physiological parameter value comprises:
circuitry configured to determine the bioactive agent (i) based at least partly on the physiological parameter value detected during usage by the individual of the artificial sensory experience being other than the expected physiological parameter value and (ii) based at least partly on a genetic profile of the individual.

26. The system of claim 1, further comprising:
circuitry configured to monitor computer usage history associated with an individual with respect to a social networking application;
circuitry configured to determine that the individual is prone to depression based at least partly on the computer usage history associated with the individual with respect to the social networking application; and
circuitry configured to modify a user interface of the social networking application with respect to the individual based at least partly on a determination that the individual is prone to depression,
wherein the circuitry configured to present an indication of a bioactive agent at least partly based on the indication of usage by the individual of the artificial sensory experience comprises circuitry configured to present an indication of an anti-depressant bioactive agent that is configured to reduce depression.

27. The system of claim 1, further comprising:
circuitry configured to present the artificial sensory experience that includes an fear-inducing virtual world aspect;
circuitry configured to monitor an appearance of the individual in association with presentation of the artificial sensory experience that includes the fear-inducing virtual world aspect;
circuitry configured to determine an anti-anxiety bioactive agent and a dosage of the anti-anxiety bioactive agent based at least partly on the monitored appearance of the individual; and
circuitry configured to modify an aspect of the artificial sensory experience based at least partly on the monitored appearance of the individual.

28. The system of claim 1, further comprising:
circuitry configured to monitor computer usage history associated with an individual with respect to a game application;
circuitry configured to determine that the individual is prone to mania based at least partly on the computer usage history associated with the individual with respect to the game application; and
wherein the circuitry configured to present an indication of a bioactive agent at least partly based on the indication of usage by the individual of the artificial sensory experience comprises circuitry configured to present an indication of an anti-manic bioactive agent that is configured to reduce mania.

29. The system of claim 1, wherein the circuitry configured to accept an indication of usage by an individual of an artificial sensory experience comprises:
circuitry configured to accept a usage score of an individual with respect to an artificial sensory experience.

30. The system of claim 1, wherein the circuitry configured to accept an indication of usage by an individual of an artificial sensory experience comprises:
circuitry configured to accept an indication motion detected using one or more motion sensors.

31. The system of claim 1, wherein the circuitry configured to present an indication of a bioactive agent at least partly based on the indication of usage by the individual of the artificial sensory experience comprises:
circuitry configured to present to a computing device an indication of a bioactive agent at least partly based on the indication of usage by the individual of the artificial sensory experience.

32. The system of claim 1, wherein the circuitry configured to present an indication of a bioactive agent at least partly based on the indication of usage by the individual of the artificial sensory experience comprises:
circuitry configured to present an indication of an anti-depressant agent at least partly based on the indication of usage by the individual of the artificial sensory experience.

33. The system of claim 1, wherein the circuitry configured to present an indication of a bioactive agent at least partly based on the indication of usage by the individual of the artificial sensory experience comprises:
circuitry configured to present an indication of an anti-anxiety agent at least partly based on the indication of usage by the individual of the artificial sensory experience.

34. The system of claim 1, wherein the circuitry configured to present an indication of a bioactive agent at least partly based on the indication of usage by the individual of the artificial sensory experience comprises:
circuitry configured to present an indication of an anti-psychotic agent at least partly based on the indication of usage by the individual of the artificial sensory experience.

* * * * *

UNITED STATES PATENT AND TRADEMARK OFFICE
CERTIFICATE OF CORRECTION

| | |
|---|---|
| PATENT NO. | : 9,026,369 B2 |
| APPLICATION NO. | : 12/290456 |
| DATED | : May 5, 2015 |
| INVENTOR(S) | : Hyde et al. |

Page 1 of 1

It is certified that error appears in the above-identified patent and that said Letters Patent is hereby corrected as shown below:

In the Claims

In Col. 54, Line 33, Claim 15 please delete "artificial sensory experience module comprises:" and replace with -- artificial sensory experience comprises: --

Signed and Sealed this
Tenth Day of November, 2015

Michelle K. Lee
*Director of the United States Patent and Trademark Office*